US010559457B2

(12) United States Patent
Eiler et al.

(10) Patent No.: US 10,559,457 B2
(45) Date of Patent: Feb. 11, 2020

(54) MASS SPECTROMETER, SYSTEM COMPRISING THE SAME, AND METHODS FOR DETERMINING ISOTOPIC ANATOMY OF COMPOUNDS

(71) Applicants: California Institute of Technology, Pasadena, CA (US); Thermo Fisher Scientific (Bremen) GmbH, Bremen (DE)

(72) Inventors: John M. Eiler, Pasadena, CA (US); Johannes Schwieters, Ganderkesee (DE)

(73) Assignees: CALIFORNIA INSTITUTE OF TECHNOLOGY, Pasadena, CA (US); THERMO FISHER SCIENTIFIC (BREMEN) GMBH, Bremen (DE)

( * ) Notice: Subject to any disclaimer, the term of this patent is extended or adjusted under 35 U.S.C. 154(b) by 0 days.

(21) Appl. No.: 16/206,951

(22) Filed: Nov. 30, 2018

(65) Prior Publication Data
US 2019/0103262 A1 Apr. 4, 2019

Related U.S. Application Data

(62) Division of application No. 14/051,392, filed on Oct. 10, 2013, now Pat. No. 10,186,410.
(Continued)

(51) Int. Cl.
*H01J 49/26* (2006.01)
*H01J 49/04* (2006.01)
(Continued)

(52) U.S. Cl.
CPC .......... *H01J 49/26* (2013.01); *H01J 49/0009* (2013.01); *H01J 49/0036* (2013.01); *H01J 49/04* (2013.01); *G01N 2030/8868* (2013.01)

(58) Field of Classification Search
CPC ........ H01J 49/0009; H01J 49/04; H01J 49/26; H01J 49/30; H01J 49/305; H01J 49/32;
(Continued)

(56) References Cited

U.S. PATENT DOCUMENTS 3,849,656 A * 11/1974 Wallington ............... H01J 5/02
250/424
5,194,732 A * 3/1993 Bateman ............... H01J 49/025
250/294
(Continued)

FOREIGN PATENT DOCUMENTS

EP 1 339 089 A1 8/2003
EP 2128791 A2 12/2009
(Continued)

OTHER PUBLICATIONS

Unknown, "Mass Spectrometry: Quadrupole Mass Filter", Advanced Lab, Jan. 2008, 8 pages.
(Continued)

*Primary Examiner* — Wyatt A Stoffa
(74) *Attorney, Agent, or Firm* — Lewis Roca Rothgerber Christie LLP

(57) ABSTRACT

A first mass spectrometer includes a first introduction device configured to select between a reference material and a first portion of an analyte and introduce the selected one of the reference material or the first portion of the analyte to an ion source, the first mass spectrometer being configured to provide third molecular analyte ions to a detector at a first mass resolution of about 30,000 or greater. A system includes the first mass spectrometer and a second mass spectrometer. A method for determining the isotopic composition of an analyte in a sample includes converting a first portion of the analyte to first molecular analyte ions, filtering out second molecular analyte ions, filtering out third molecular analyte ions, detecting two or more of the third
(Continued)

molecular analyte ions at a mass resolution of about 30,000 or greater to determine the isotopic composition of at least a portion of the analyte.

15 Claims, 48 Drawing Sheets

Related U.S. Application Data

(60) Provisional application No. 61/712,022, filed on Oct. 10, 2012, provisional application No. 61/869,461, filed on Aug. 23, 2013.

(51) Int. Cl.
*H01J 49/00* (2006.01)
*G01N 30/88* (2006.01)

(58) Field of Classification Search
CPC ............... H01J 49/0036; H01J 49/025; G01N 2030/8868
See application file for complete search history.

(56) References Cited

U.S. PATENT DOCUMENTS

| | | | |
|---|---|---|---|
| 5,347,125 A | 9/1994 | Holmes et al. | |
| 5,661,298 A * | 8/1997 | Bateman | H01J 49/282 250/281 |
| 5,723,862 A | 3/1998 | Forman | |
| 6,297,501 B1 * | 10/2001 | Merren | H01J 49/30 250/282 |
| 7,653,494 B2 | 1/2010 | Neascu et al. | |
| 7,820,966 B2 * | 10/2010 | Bateman | B01D 59/44 250/281 |
| 7,928,369 B2 * | 4/2011 | Hatscher | H01J 49/0422 250/281 |
| 7,979,258 B2 | 7/2011 | Goldberg et al. | |
| 8,402,814 B2 * | 3/2013 | Hatscher | B01D 59/44 73/23.37 |
| 8,895,915 B2 | 11/2014 | Schwieters et al. | |
| 2002/0102610 A1 | 8/2002 | Townsend et al. | |
| 2004/0046116 A1 * | 3/2004 | Schroeder | H01J 49/0086 250/281 |
| 2004/0083063 A1 * | 4/2004 | McClure | G16C 20/20 702/22 |
| 2005/0086017 A1 | 4/2005 | Wang | |
| 2005/0255606 A1 * | 11/2005 | Ahmed | G06K 9/00503 436/173 |
| 2005/0279933 A1 * | 12/2005 | Appelhans | H01J 49/025 250/296 |
| 2006/0113464 A1 * | 6/2006 | Litherland | B01D 59/44 250/288 |
| 2006/0228301 A1 * | 10/2006 | Boros | G01N 33/5011 424/9.1 |
| 2007/0034810 A1 | 2/2007 | Hoyes | |
| 2009/0283673 A1 * | 11/2009 | Shilov | H01J 49/0036 250/282 |
| 2009/0314057 A1 * | 12/2009 | Hatscher | B01D 59/44 73/23.35 |
| 2010/0108879 A1 | 5/2010 | Bateman et al. | |
| 2011/0086430 A1 * | 4/2011 | Krummen | G01N 30/84 436/161 |
| 2011/0100222 A1 | 5/2011 | Reilly | |
| 2012/0032075 A1 * | 2/2012 | De Chambost | H01J 49/06 250/298 |
| 2012/0083041 A1 * | 4/2012 | Martin | H01J 49/0009 436/141 |
| 2012/0085904 A1 * | 4/2012 | Schwieters | H01J 49/025 250/282 |
| 2012/0211651 A1 * | 8/2012 | Vogel | H01J 49/326 250/296 |
| 2013/0103337 A1 * | 4/2013 | Eiler | G16C 20/20 702/86 |
| 2013/0124108 A1 | 5/2013 | Eiler | |
| 2014/0346335 A1 * | 11/2014 | Gluckstad | G02B 21/32 250/251 |
| 2015/0355227 A1 | 12/2015 | Gluckstad | |
| 2016/0154006 A1 * | 6/2016 | Hermanson | G01N 33/60 506/12 |
| 2017/0030921 A1 * | 2/2017 | Duhr | B01L 3/502761 |
| 2018/0202913 A1 * | 7/2018 | Tanner | G01N 11/00 |

FOREIGN PATENT DOCUMENTS

| | | |
|---|---|---|
| WO | WO 94/07257 | 3/1994 |
| WO | WO 2011/128702 A1 | 10/2011 |
| WO | WO 2013/070304 A1 | 5/2013 |

OTHER PUBLICATIONS

Baldwin, "Protein Identification by Mass Spectrometry", Molecular & Cellular Proteomics 3.1, 2004, The American Society for Biochemistry and Molecular Biology, Inc., pp. 1-9.

De Laeter, John R., and Allen K. Kennedy, "A double focusing mass spectrometer for geochronology," International Journal of Mass Spectrometry, 178.1 (1998): 43-50.

Delta V Plus Operating Manual, Thermo Electron Corporation, 2005.

Gilbert, Alexis et al., "composition of IRMS and NMR spectrometry for the determination of intramolecular 13 C isotope composition: application to ethanol," Talanta 99 (2012): 1035-1039.

Rubakhin, et al., "A mass spectrometry primer for mass spectrometry imaging", Apr. 7, 2011, NIH Public Access Author Manuscript, pp. 1-29 (Also published as Methods Mol. Biol., 2010, vol. 656, pp. 21-24) doi: 10.1007/978-1-60761-764-4_2.

Van Galen, "Mass Spectrometry @ the Organic Chemistry Department (A Guide for novel users)", Organic Chemistry Department, Nijmegen University, Sep. 2005, 47 pages.

International Search Report and Written Opinion of the International Searching Authority for PCT/US2012/061191, dated Mar. 29, 2013, 10 pages.

International Search Report and Written Opinion of the International Searching Authority for PCT/US2012/061192, dated Mar. 28, 2013, 11 pages.

International Search Report and Written Opinion of the International Searching Authority, dated Jan. 16, 2014, issued in PCT/US2013/064409 (11 pages).

* cited by examiner

MASS SPECTROMETER, SYSTEM COMPRISING THE SAME, AND METHODS FOR DETERMINING ISOTOPIC ANATOMY OF COMPOUNDS

CROSS-REFERENCE TO RELATED APPLICATION(S)

This application is a divisional application of, and claims priority to and the benefit of U.S. patent application Ser. No. 14/051,392, filed Oct. 10, 2013, titled MASS SPECTROMETER, SYSTEM COMPRISING THE SAME, AND METHODS FOR DETERMINING ISOTOPIC ANATOMY OF COMPOUNDS which claims priority to and the benefit of U.S. Provisional Application Ser. No. 61/712,022, filed on Oct. 10, 2012, titled SYSTEM OF MASS SPECTROMETERS FOR ISOTOPIC ANALYSIS OF INTACT, HIGH MOLECULAR WEIGHT MOLECULES, and U.S. Provisional Application Ser. No. 61/896,461, filed on Aug. 23, 2013, titled METHODS AND APPARATUS FOR ANALYZING ISOTOPIC COMPOSITION OF MOLECULES, the entire contents of all of which are incorporated herein by reference.

FIELD

The following description generally relates to apparatus, systems and methods for determining the isotopic anatomy of an analyte, such as molecular gases and volatile organic compounds. More particularly, the following description relates to apparatus for measuring intensity ratios of molecular ions, fragment ions and adduct ions, systems including the apparatus, and to methods for determining abundance ratios of isotopologues and position-specific isotopic compositions within a sample or samples.

BACKGROUND

Conventional mass spectrometry primarily focuses on measuring the concentrations of isotopic species including only one rare isotope. These mass spectrometric techniques generally determine the overall concentration of an isotope, irrespective of its location in the molecule (i.e., the atomic site or sites of isotopic substitution) or the proportions of multiple isotopic substitutions within the same molecule. Consequently, conventional mass spectrometry fails to distinguish among different isotopologues of the same molecule and thus disregards a large amount of useful information that can be determined from a complete analysis of all the different isotopologues present in a sample. However, determining the isotopic composition of a molecule including more than one rare isotope can provide useful information, such as the geographic origin of the molecule, temperature of origin of the molecule (or a sample including the molecule) or the identity of a parent molecule from which the molecule was derived.

The shortcomings of conventional mass spectrometry are particularly noteworthy for organic compounds, which may have large numbers of isotopologues. For example, methane ($CH_4$) has 57 distinct isotopic versions including various non-equivalent combinations of $^{12}C$, $^{13}C$, $^{14}C$, hydrogen, deuterium, and tritium. The number of isotopologues of low-symmetry molecular structures grows approximately geometrically with the number of atomic positions, meaning alkanes, lipids, sugars and other complex hydrocarbons containing several or more carbon atoms typically have at least several hundred distinct isotopologues; many such molecules have $10^6$ or more distinct isotopologues. Abundances of only a small subset of these species (typically 2-5) are meaningfully constrained by commonly recognized methods of isotopic analysis.

Although other methods have been developed to expand the set of isotopologues that can be analyzed with useful precision, these methods are applicable to a relatively narrow range of sample types and sizes and to a restricted range of isotopic species in a given analyte target. For example, demonstrated site-specific natural isotope fractionation-nuclear magnetic resonance (SNIF-NMR) techniques can determine, for example, relative deuterium concentration and specific deuterium-site locations in a molecule based on the deuterium NMR signal obtained for the molecule. Comparison of the relative deuterium concentration of the molecule with known global distributions of hydrogen isotope concentrations can provide information regarding the geographic origin of a sample from which the molecule was obtained. SNIF-NMR techniques, however, are not capable of analyzing abundances of molecules containing two or more rare isotopes at their natural abundances and, more generally, require sample sizes that are prohibitively large for many applications and require relatively long, costly analyses. Similarly, established "clumped isotope" mass spectrometric methods can analyze only a few isotopologues of small, simple, highly volatile molecules, principally because of their inability to resolve isobaric interferences and the poor sensitivity of existing gas source multi-collector sector mass spectrometers. Clumped isotope geochemistry and related techniques are described in more detail in "Clumped-isotope' geochemistry—The study of naturally-occurring, multiply-substituted isotopologues," Earth and Planetary Science Letters, Vol. 262, Issues 3-4, pages 309-327, the entire contents of which are herein incorporated by reference.

SUMMARY

Aspects of embodiments of the invention are directed to apparatus, systems and methods for the quantitative analysis of the isotopologues of gaseous compounds and/or volatile organic compounds. According to one embodiment, the gaseous compounds and/or volatile organic compounds are introduced into a gas source isotope ratio mass spectrometer, which converts the compounds into molecular ion, fragment ion and/or adduct ion beams, which are analyzed to determine the isotopic composition of the gaseous compounds and/or volatile organic compounds. Aspects of embodiments are also directed to methods of data processing and standardization for converting measured intensity ratios of isotopic species into abundance ratios of isotopologues, including multiply-substituted isotopologues and position-specific isotopic compositions.

Embodiments of the invention are also directed to various applications of the apparatus, systems and methods, such as applications in earth and environmental science (e.g., thermometry of natural compounds and developing budgets for atmospheric gases), chemistry, forensics (e.g., chemical forensics and explosives fingerprinting), biomedical research, diagnosis and treatment of diseases (e.g., drug and/or drug metabolite tracking), and hydrocarbon (e.g., oil and gas) exploration. For example, embodiments of the invention are directed to identifying the location of oil and gas deposits (e.g., a potential oil-field) based on the relative proportion of isotopologues (e.g., isotopologues of methane) of a sample as determined using the apparatus and methods described herein.

For example, one embodiment of the invention is directed to the determination of relative abundances of the methane isotopologues: $^{12}CH_4$, $^{13}CH_4$, $^{12}CH_3D$ and $^{13}CH_3D$. The apparatus and methods described herein can be used to obtain molecular analyte ion data from a sample of methane. The molecular analyte ion data can then be used to determine the isotopic compositions of the constituent components of the sample and, thus, the relative abundances of the $^{12}CH_4$, $^{13}CH_4$, $^{12}CH_3D$ and $^{13}CH_3D$ isotopologues in the methane sample. The relative proportions of the preceding methane isotopologues are a function of temperature in methane that has achieved thermodynamic equilibrium. Thus, a determination of the relative proportions of the preceding isotopologues in a sample of methane can be used to measure the temperatures of origin and/or storage of this component of natural gas, as an aid to the exploration and development of oil and gas deposits.

Another embodiment is directed to the determination of relative abundances of $^{13}C$-bearing isotopologues of $CH_3+$ and $C_2H_5+$ ion fragments generated by ionization of propane. The foregoing data, combined with characterizations of the empirical constants describing fragmentation and recombination reactions in the ion source, can be used to determine the difference in $^{13}C$ content between the terminal and central carbon positions of propane. This difference is predicted to be a function of temperature in thermodynamically equilibrated propane (and thus can be used to establish the temperature of formation, as for the methane analysis described above). In non-equilibrated gases, this difference may illuminate the chemical kinetic mechanisms of natural gas maturation, and thus also aid in the exploration and development of oil and gas deposits.

Yet another embodiment of the invention is directed to the analysis of relative proportions of $^{13}C$, D and/or $^{18}O$ bearing isotopologues of ion fragments generated by delivering volatile organic compounds, such as derivatized sugars, into the ion source. The foregoing data, combined with characterizations of the empirical constants describing fragmentation and recombination reactions in the ion source, will allow for the characterization of isotopic fingerprints associated with diverse sources of such compounds and thus aid in the forensic studies of diverse organic compounds (functionally, any species that can be derivatized to create a compound that can be delivered to the ion source through a heated gas chromatographic column).

According to embodiments of the invention, a mass spectrometer includes a first ion travel path and a first introduction device configured to select between a reference material and a first portion of an analyte and introduce the selected one of the reference material or the first portion of the analyte to a first ion source. The first ion source has a first entrance slit having a first width. The first ion source is configured to convert the reference material or the first portion of the analyte to first molecular analyte ions and to guide the first molecular analyte ions along the first ion travel path, each of the first molecular analyte ions having a momentum. A first momentum filter is positioned downstream from the first ion source and is configured to receive the first molecular analyte ions, the first momentum filter having a first radius of curvature along the first ion travel path. The momentum filter is configured to filter out second molecular analyte ions from the first molecular analyte ions according to their momenta, each of the second molecular analyte ions having an energy level. A first energy filter is positioned downstream from the first momentum filter and is configured to receive the second molecular analyte ions, the first energy filter having a second radius of curvature along the first ion travel path. The first energy filter is configured to filter out third molecular analyte ions from the second molecular analyte ions according to their energy levels. The mass spectrometer also includes a detector positioned downstream of the first energy filter and configured to receive the third molecular analyte ions. The first width of the first entrance slit and the first and second radii of curvature are selected to provide a mass resolution at the detector of about 30,000 or greater.

The detector can include a single collector, and the single collector can be configured to detect the third molecular analyte ions. In some embodiments, each of the third molecular analyte ions has a mass that differs from the masses of the other third molecular analyte ions by less than 1 atomic mass unit. The first introduction device can be configured to receive the first portion of the analyte as a gas phase analyte. The analyte can be a gas phase analyte and the first introduction device can include a first inlet coupled to a sample reservoir including the gas phase analyte. The reference material can be a gas phase reference material and the first introduction device can include a second inlet coupled to a reference reservoir configured to accommodate the gas phase reference material. The sample reservoir can be configured to accommodate the gas phase analyte at first pressure, the reference reservoir can be configured to accommodate the gas phase reference material at a second pressure, and the first and second pressures can be the same. The first introduction device can be configured to receive the first portion of the analyte entrained in a flow of inert gas.

In some embodiments, the first momentum filter is configured to produce a magnetic field, the first energy filter is configured to produce an electric field, and the mass spectrometer is configured to vary the masses of the third molecular analyte ions detected at the detector by maintaining the strength of the magnetic field of the first momentum filter at a set value and varying the strength of the electric field of the first energy filter. The masses of the third molecular analyte ions detected at the detector can be different from one another by less than one atomic mass unit. The masses of the third molecular analyte ions detected at the detector can be the same when rounded to the nearest whole number. The mass spectrometer can be configured to vary the strength of the electric field of the first energy filter in a set range to vary the masses of the third molecular analyte ions detected at the detector in a range spanning one atomic mass unit. The mass spectrometer can be configured to vary the strength of the electric field of the first energy filter across the set range a plurality of times to produce a plurality of spectra corresponding to the range spanning one atomic mass unit. The mass spectrometer can further include a processor configured to produce a model of each of the spectra, and to average the models to produce a modeled spectrum. In some embodiments, the mass spectrometer further includes a processor configured to average the plurality of spectra to produce an averaged spectrum and to produce a model of the averaged spectrum.

The first momentum filter can be configured to produce a magnetic field. The first energy filter can be configured to produce an electric field. The mass spectrometer can be configured to vary a first set of masses of the third molecular analyte ions detected at the detector by maintaining a first strength of the magnetic field of the momentum filter at a first set value and varying a strength of the electric field of the first energy filter. The mass spectrometer can be configured to vary a second set of masses of the third molecular analyte ions detected at the detector by maintaining a second strength of the magnetic field of the first momentum filter at a second set value and varying a strength of the electric field of the first energy filter.

The mass spectrometer can be configured to vary the first strength of the electric field of the first energy filter in a first set range to vary the first set of masses of the third molecular analyte ions of the third output detected at the detector in a first range spanning one atomic mass unit. The mass spectrometer can be configured to vary the second strength of the electric field of the first energy filter in a second set range to vary the second set of masses of the third molecular analyte ions detected at the detector in a second range spanning one atomic mass unit.

Embodiments of the present invention are also directed to a system for analyzing an analyte, the system including a first mass spectrometer as described above and a second mass spectrometer. The second mass spectrometer includes a second ion travel path and a second ion source having a second entrance slit having a second width. The second ion source is configured to convert a second portion of the analyte to fourth molecular analyte ions and to guide the fourth molecular analyte ions along the second ion travel path, each of the fourth molecular analyte ions having an energy level. A second energy filter is positioned downstream from the second ion source and is configured to receive the fourth molecular analyte ions, the second energy filter having a third radius of curvature along the second ion travel path. The second energy filter is configured to filter out fifth molecular analyte ions from the fourth molecular analyte ions according to their energy levels, each of the fifth molecular analyte ions having a momentum. A second momentum filter is positioned downstream from the second energy filter and is configured to receive the fifth molecular analyte ions, the second momentum filter having a fourth radius of curvature along the second ion travel path. The second momentum filter is configured to filter out sixth molecular analyte ions from the fifth molecular analyte ions according to their momenta. The second mass spectrometer also includes a detector array positioned downstream of the second momentum filter and configured to receive the sixth molecular analyte ions. The second width and the third and fourth radii of curvature are selected to provide a second mass resolution at the detector array of about 20,000 or greater. The system can include a processor configured to process first molecular analyte ion data from the first mass spectrometer and second molecular analyte ion data from the second mass spectrometer. The processor can include a first processor configured to process the first molecular analyte ion data and a second processor configured to process the second molecular analyte ion data.

Aspects of embodiments of the invention are also directed to applications of the mass spectrometer. For example, according to embodiments of the invention, a method of identifying a potential oil-field includes analyzing a sample from a target field using an embodiment of the system described herein to obtain molecular analyte ion data, where the sample includes the analyte. The method further includes analyzing the molecular analyte ion data to obtain an isotopic composition of at least a portion of the analyte. The isotopic composition of the analyte is used to determine relative proportions of at least a portion of isotopologues in the sample. The relative proportions of the isotopologues of the sample are compared to a database to determine a property of the sample, such as the temperature of origin (e.g., temperature of formation) and/or temperature of storage of the sample. The temperature of origin (e.g., temperature of formation) and/or temperature of storage of the sample can be used in conjunction with other information to decide whether or not to drill at the target field. In some embodiments, the analyte is a hydrocarbon, such as methane, ethane, propane, butane, pentane, hexane, or the like.

According to another embodiment of the invention, a method of analyzing a drug or drug metabolite includes analyzing a sample of the drug or drug metabolite using an embodiment of the system described herein to convert the drug or drug metabolite to molecular analyte ions and to obtain molecular analyte ion data, where the sample includes the analyte. The method also includes analyzing the molecular analyte ion data to obtain an isotopic composition of at least a portion of the drug or drug metabolite. The method further includes comparing the isotopic composition obtained for the drug or drug metabolite to a database of isotopic compositions. The correlation between the isotopic composition obtained for the drug or drug metabolite and the database of isotopic compositions can be used to determine a property of the drug or the drug metabolite and is useful in the forensic study of diverse organic compounds.

According to embodiments of the invention, a method of determining an amount of an anthropogenic contribution to an atmospheric concentration of an atmospheric gas includes analyzing a sample of the atmospheric gas using an embodiment of the system described herein to obtain molecular analyte ion data, where the sample includes the analyte. The method further includes analyzing the molecular analyte ion data to obtain an isotopic composition of at least a portion of the analyte. The method also includes comparing the isotopic composition obtained for the analyte to a database of isotopic compositions. The correlation between the isotopic composition obtained for the analyte and the database of the isotopic compositions can be used to determine the amount of the anthropogenic contribution to the atmospheric concentration of the atmospheric gas.

According to another embodiment of the invention, a method for diagnosing or treating a disease includes analyzing a sample from a patient using an embodiment of the system described herein to obtain molecular analyte ion data, where the sample includes the analyte. The method further includes analyzing the molecular analyte ion data to obtain an isotopic composition of at least a portion of the analyte. The method also includes comparing the isotopic composition obtained for the analyte to a database of isotopic compositions. The correlation between the isotopic composition obtained for the analyte and the database of the isotopic compositions can be used to determine a disease diagnosis or disease treatment protocol.

According to another embodiment of the invention, a method for determining a prior temperature of a sample includes analyzing the sample using an embodiment of the system described herein to obtain molecular analyte ion data, where the sample includes the analyte. The method further includes analyzing the molecular analyte ion data to obtain an isotopic composition of at least a portion of the analyte. The method also includes comparing the isotopic composition obtained for the analyte to a database of isotopic compositions. The correlation between the isotopic composition obtained for the analyte and the database of isotopic compositions can be used to determine the prior temperature of the sample.

Aspects of embodiments of the invention are also directed to methods for determining the isotopic composition of an analyte in a sample. For example, according to embodiments of the invention, a method for determining the isotopic composition of an analyte in a sample includes converting a first portion of the analyte to first molecular analyte ions using a first ion source of a first mass spectrometer. The method further includes filtering out second molecular analyte ions from the first molecular analyte ions according to their momenta, and filtering out third molecular analyte ions from the second molecular analyte ions according to their energy levels. The method also includes detecting two or more of the third molecular analyte ions of the third output at a mass resolution of about 30,000 or greater to produce first molecular analyte ion data. The method further includes analyzing the first molecular analyte ion data to determine an isotopic composition of at least a portion of the analyte.

In some embodiments, the two or more of the third molecular analyte ions have respective masses that are the same when rounded to the nearest whole number, and the first molecular analyte ion data comprises a separate, mass resolved signal for each of the two or more of the third molecular analyte ions. In some embodiments, the two or more of the third molecular analyte ions have respective masses that differ by less than one atomic mass unit, and the first molecular analyte ion data includes a separate, mass resolved signal for each of the two or more of the third molecular analyte ions. In some embodiments, the third output includes two or more first molecular analyte ion beams, and the detecting the two or more of the third molecular analyte ions includes scanning at least two of the first molecular analyte ion beams across a single detector. The third molecular analyte ions of each of the two or more first molecular analyte ion beams can have masses that differ from one another by less than about 1 atomic mass unit. The first portion of the analyte can be introduced into the mass spectrometer as a continuous flow prior to converting the first portion of the analyte to the first molecular analyte ions. The first portion of the analyte can be introduced into the mass spectrometer as a time-resolved pulse prior to converting the first portion of the analyte to the first molecular analyte ions. The analyte can include two or more analyte isotopologues, analyte isotopomers or mixtures thereof. The analyzing can further include determining the molecular position of at least one isotope in at least one of the analyte isotopologues or the analyte isotopomers.

In some embodiments, the method further includes converting a second portion of the analyte to fourth molecular analyte ions using a second ion source in a second mass spectrometer. The method further includes filtering out fifth molecular analyte ions from the fourth molecular analyte ions according to their energy levels, and filtering out sixth molecular analyte ions from the fifth molecular analyte ions according to their momenta. The method also includes detecting two or more of the sixth molecular analyte ions at a second mass resolution of about 20,000 or greater to produce second molecular analyte ion data. The method further includes analyzing the second molecular analyte ion data to determine an isotopic composition of at least a portion of the analyte.

According to another embodiment of the invention, a method of identifying a potential oil-field includes determining an isotopic composition of a sample from a target field according to one of the methods described herein, where the sample includes the analyte. The method further includes using the isotopic composition to determine relative proportions of at least a portion of the isotopologues of the analyte in the sample. The relative proportions of the isotopologues of the sample are compared to a database to determine a property of the sample, such as the temperature of origin (e.g., temperature of formation) and/or temperature of storage of the sample. The temperature of origin (e.g., temperature of formation) and/or temperature of storage of the sample can be used in conjunction with other information to decide whether or not to drill at the target field. In some embodiments, the analyte is a hydrocarbon, such as methane, ethane, propane, butane, pentane, hexane, or the like.

According to another embodiment of the invention, a method of analyzing a drug or drug metabolite includes determining an isotopic composition of a sample of the drug or the drug metabolite according to one of the methods described herein, where the sample includes the analyte. The method also includes comparing the isotopic composition obtained for the drug or drug metabolite to a database of isotopic compositions. The correlation between the isotopic composition obtained for the drug or drug metabolite and the database of isotopic compositions can be used to determine a property of the drug or the drug metabolite and is useful in the forensic study of diverse organic compounds.

According to another embodiment of the invention, a method of determining an amount of an anthropogenic contribution to an atmospheric concentration of an atmospheric gas includes determining an isotopic composition of a sample of the atmospheric gas according to one of the methods described herein, where the sample includes the analyte. The method further includes comparing the isotopic composition obtained for the analyte to a database of isotopic compositions. The correlation between the isotopic composition obtained for the analyte and the database of the isotopic compositions can be used to determine the amount of the anthropogenic contribution to the atmospheric concentration of the atmospheric gas.

According to another embodiment, a method for diagnosing or treating a disease includes determining an isotopic composition of a sample from a patient according to one of the methods described herein, where the sample includes the analyte. The method further includes comparing the isotopic composition obtained for the analyte to a database of isotopic compositions. The correlation between the isotopic composition obtained for the analyte and the database of the isotopic compositions can be used to determine a disease diagnosis or disease treatment protocol.

According to another embodiment of the invention, a method of determining a prior temperature of a sample includes determining an isotopic composition of the sample according to one of the methods described herein, where the sample includes the analyte. The method further includes comparing the isotopic composition obtained for the analyte to a database of isotopic compositions. The correlation between the isotopic composition obtained for the analyte and the database of isotopic compositions can be used to determine the prior temperature of the sample.

In another embodiment, a mass spectrometer

BRIEF DESCRIPTION OF THE DRAWINGS

These and other features and advantages of the present invention will be better understood by reference to the following detailed description when considered in conjunction with the accompanying drawings, briefly described below.

DETAILED DESCRIPTION

Figure 1:
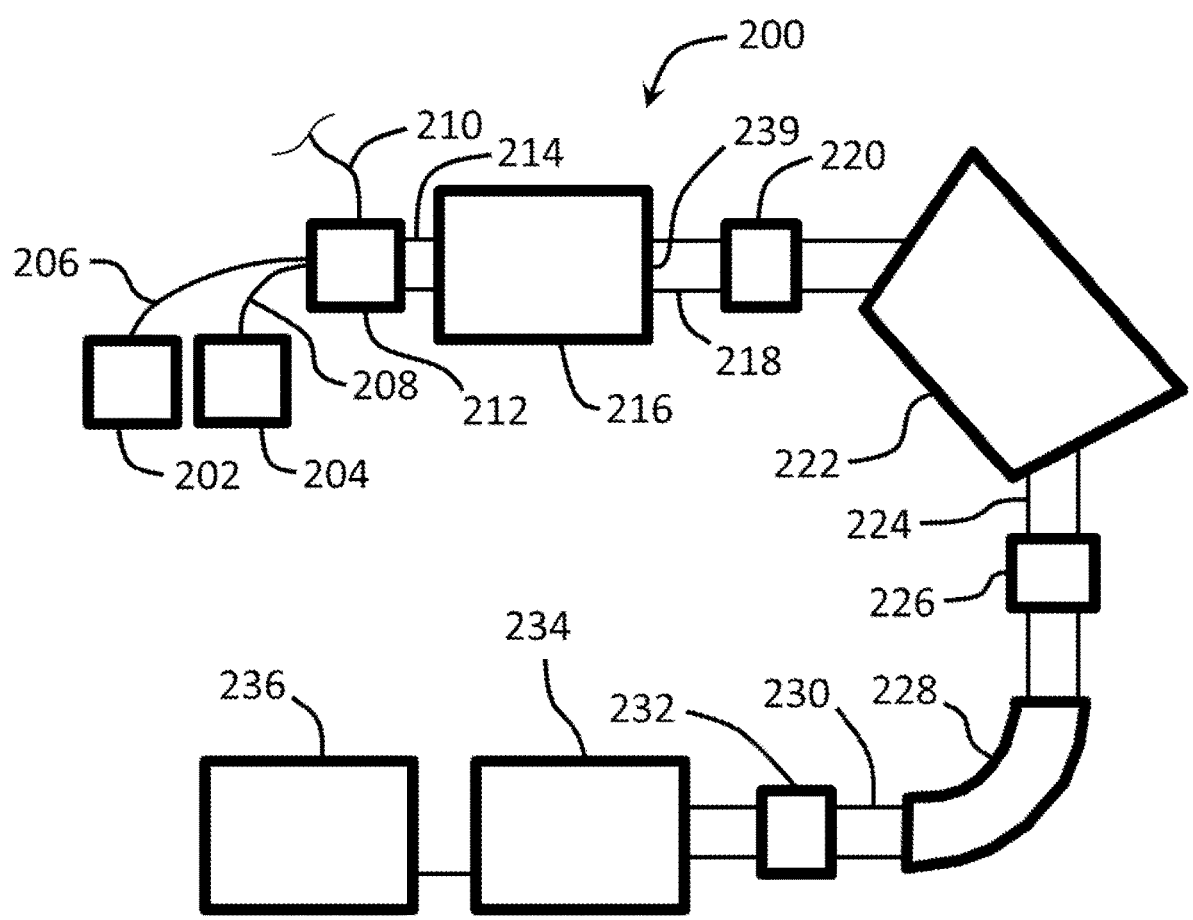
FIG. 1 is a schematic top view of a first mass spectrometer according to one embodiment of the invention.

Embodiments of the present invention are directed to apparatus, systems and methods for determining the isotopic composition (or isotopic anatomy) of an analyte, such as a volatile and/or organic molecule. For example, embodiments of the invention are directed to apparatus and systems for measuring intensity ratios of molecular ions, fragment ions and/or adduct ions, and to methods for determining abundance ratios of isotopologues and position-specific isotopic compositions of an analyte within a sample or samples. Quantitative analysis of the relative abundances of isotopologues of molecules can be accomplished through: (1) high-resolution, multi-collector mass spectrometric analysis of molecular ions, fragment ions and/or adduct ions of such molecules (e.g., the analyte) produced by gas-source electron impact ionization; (2) calibration of a variety of relevant analytical biases through comparison of the data obtained for the sample (e.g., the analyte) with data obtained for appropriately prepared standards (e.g., reference materials); and (3) reconstruction of the original molecular isotopic structure of the analyte through integration of measured compositions of the various fragment species.

As used herein, the term "isotopologues" is used in its art recognized sense and refers to molecules that have the same chemical structure, but differ in their isotopic composition (i.e., the isotopologues have differing isotopic substituents). For example, $CH_3D$ and $CH_4$ are isotopologues of one another. As used herein, the term "multiply-subsituted isotopologue" is used in its art recognized sense and refers to a molecule that includes two or more rare isotopes. For example, $^{13}CH_3D$ is a multiply-substituted isotopologue. As used herein, the term "isotopomers" is used in its art recognized sense and refers to molecules having the same chemical composition and the same kind and amounts of isotopic substituents, but differ in the molecular positions of at least some of the atoms (e.g., the positions of the isotopic substituents). For example, $CH_2D$-$CH_2$—$CH_3$ and $CH_3$-$CHD$-$CH_3$ are isotopomers of one another. Isotopomers are strictly identical at any mass resolution, and cannot be separated by their respective mass to charge ratios, since they have the same mass. As used herein, the term "cardinal mass" refers to the mass of an ion or molecule after rounding to the nearest whole number. Thus, two or more ions (including molecular ions) having the same cardinal mass (or a single cardinal mass) would have masses that each round to the same nearest whole number, even though the two or more ions may have absolute masses that are different from one another. Ions derived from a single sample and having the same cardinal mass may be analyzed separately using a mass spectrometer only when the mass resolving power of the mass spectrometer is sufficient to distinguish the small differences in mass that arise due to one ion containing a heavy isotope (e.g., $^{13}C$) and the other ion containing another, different heavy isotope (e.g., D). As used herein, the term "data" is used in its art recognized sense and refers to quantities obtained using the apparatus or methods described herein and can include, for example, a single ion intensity, a set of ion intensities, ratios of ion intensities, a mass spectrum and/or mass spectra. As used herein, the terms "molecular analyte ion" and "molecular analyte ions" refer to ions of chemical compounds having two or more atoms bonded to one another and, as would be understood by those of skill in the art, encompass ions of intact analyte molecules, ions of fragments of the analyte molecules, and ions of adducts of the analyte molecules and/or its fragments.

Embodiments of the present invention are directed to the combination of a high resolution, high precision measurement, at a single cardinal mass, of ions having high cardinal mass with a high precision, lower resolution measurement, at two or more different cardinal masses, of ions having different cardinal masses.

Apparatus, systems and/or methods according to embodiments of the invention can be used in earth and environmental science (e.g., thermometry of natural compounds and developing budgets for atmospheric gases), chemistry, forensics (e.g., chemical forensics and explosives fingerprinting), biomedical research, diagnosis and treatment of diseases (e.g., drug and/or drug metabolite tracking), and hydrocarbon (e.g., oil and gas) exploration. For example, embodiments of the invention are directed to a method of identifying a potential (e.g., a high-potential) subsurface hydrocarbon deposit (e.g., an oil-field).

FIG. 1 is a schematic top view of a first mass spectrometer 200 according to an embodiment of the present invention. The spectrometer shown in FIG. 1 may be any double-focusing, single-collector sector mass spectrometer capable of ionizing molecular gases and achieving mass resolutions of approximately 50,000 or greater. The embodiment shown in FIG. 1 assumes a reverse Nier-Johnson geometry. In the embodiment shown in FIG. 1, the first mass spectrometer 200 includes a first ion travel path along a first ion source 216, a first entrance slit 239, a first momentum filter 222 (e.g., a magnetic sector), and a first energy filter 228 (e.g., an electrostatic analyzer or "ESA") configured to provide molecular analyte ions to a detector 234. The first mass spectrometer 200 can be configured to provide a first mass resolution (which is described in more detail below) of 30,000 or greater (e.g., 49,000 or greater) at the detector 234 by sequentially arranging the first entrance slit, the first momentum filter and the first energy filter, and by appropriately selecting a first width of the first entrance slit, and a first radius of curvature of the first momentum filter, and a second radius of curvature of the first energy filter.

The mass resolution achieved by a mass spectrometer according to embodiments of the invention is generally proportional to the separation distance between two ion beams that the mass spectrometer can achieve for ion beams that include respective ions having masses that are different from one another. In embodiments of the first mass spectrometer, the separation distance between the ion beams is controlled by the radii of curvature of the ion beams as they pass through the first momentum filter and first energy filter (e.g., the electrostatic analyzer), and inversely proportional to the width of each ion beam, which is proportional to the first width of the first entrance slit. Additionally, the highest mass resolutions can be achieved through a double focusing sector mass spectrometer design, where both momentum and energy filtering occur in an analyzer including the momentum filter and the energy filter. The first momentum filter and the first energy filter work together in that the first energy filter images the focal point of the first momentum filter. Thus, according to embodiments of the first mass spectrometer, the ions are filtered by momentum (e.g., by the momentum filter) prior to being filtered by energy (e.g., by the energy filter). Accordingly, the first momentum filter has dimensions that are consistent with the creation of a double-focusing condition at the detector, given the momenta of the ions as they exit the first ion source and the first radius of curvature of the first momentum filter. For example, in embodiments of the first mass spectrometer, first mass resolutions in the range of about 2,000 to about 100,000 (e.g., about 30,000 to about 100,000; or about 49,000 to about 100,000) can be achieved if the first entrance slit has a first width of about 200 µm to about 1 µm, respectively, the first molecular analyte ions are accelerated to 5 keV after exiting the first ion source, the first radius of curvature of the momentum filter is about 35 cm, and the second radius of curvature of the energy filter is about 50 cm.

Embodiments of the first mass spectrometer also include a source of an analyte and a source of a reference material. For example, the embodiment of the first mass spectrometer shown in FIG. 1 also includes a sample reservoir 202 and a reference reservoir 204. In some embodiments, the analyte is a gas phase analyte, and the first introduction device includes a first inlet coupled to the sample reservoir 202. The sample reservoir 202 can accommodate a the gas phase analyte. In some embodiments, the reference material is a gas phase reference material, and the first introduction device includes a second inlet coupled to the reference reservoir 204. The reference reservoir 204 can accommodate the reference material (e.g., the gas phase reference material). For example, the sample reservoir 202 can include a gas phase sample including a gas phase analyte, and/or the sample reservoir 202 can include a liquid phase sample and a vapor including the gas phase analyte. In some embodiments, the reference reservoir includes a liquid phase reference material and/or the gas phase reference material. Accordingly, in some embodiments, the sample and the reference material may each be a room temperature gas, or a high vapor pressure liquid. The sample reservoir 202 can accommodate the gas phase analyte at a first pressure, the reference reservoir 204 can accommodate the gas phase reference material at a second pressure, and the first and second pressures can be the same (or substantially the same).

The analyte described herein can be any suitable gas or volatile compound (e.g., a volatile organic compound) that can be translated through a tube (e.g., a confined tube) as a pure gas or as an analyte mixed with a carrier gas (e.g., an inert gas). For example, a first portion of the analyte can be entrained in the carrier gas. The analyte can be any analyte that can be suitably analyzed using the subject matter disclosed herein. For example, the analyte can be, or can be derived from, any suitable gas, volatile compound, semi-volatile liquid or sublimable solid. For example, volatile compounds can include any organic compound that can be suitably measured or analyzed in the mass spectrometer, such as, but not limited to alkanes (e.g., n-alkanes), oxygenates, aromatic compounds, heteroaromatic compounds, cyclic compounds, heterocyclic compounds, and the like Additionally, the analyte can be derived from a sample that is unsuitable for analysis in the mass spectrometer, such as a non-volatile liquid organic compound or liquid or non-sublimable solid. For example, a sample that is otherwise incapable of being analyzed in the mass spectrometer can be converted into an analyzable sample by preparing an analyte that is a derivative or reaction product of the sample and that is capable of being analyzed in the mass spectrometer, and thereby the derivative or reaction product can be used as a proxy for the sample that would be otherwise unsuitable for analysis or measurement. The analyte can be any suitable compound that can be introduced into the first mass spectrometer 200.

The analyte and the reference material can be provided to a first introduction device 212 (e.g., a changeover block), which can select between the reference material and a first portion of the analyte and introduce the selected one of the reference material or the first portion of the analyte to the first ion source. For example, the analyte and/or the reference material can be provided to the first introduction device 212 in the gas phase via conduits 206 and 208 (e.g., capillaries), respectively, for example, as a viscous bleed. When the gas phase analyte and the gas phase reference material are provided to the first introduction device 212 from the above-described reservoirs (e.g., as a viscous bleed), the quantity of the analyte or the reference material provided to the first introduction device has little or no variation over time, and stable and time invariant results can be obtained.

In some embodiments, the analyte and/or the reference material are supplied to the first introduction device entrained in (or mixed) in a flow of an inert carrier gas (e.g., a helium carrier gas), for example in an effluent from a gas chromatograph or a liquid chromatograph. For example, in FIG. 1 the analyte and/or the reference material can be provided to the first introduction device 212 via a conduit 210, which can also be coupled to a gas chromatograph and/or a liquid chromatograph. In some embodiments, the first mass spectrometer can include a plurality of conduits 210 for transmitting a plurality of carrier gas streams, and the first mass spectrometer can further include a valve for selecting between the plurality of carrier gas streams.

Figure 2:
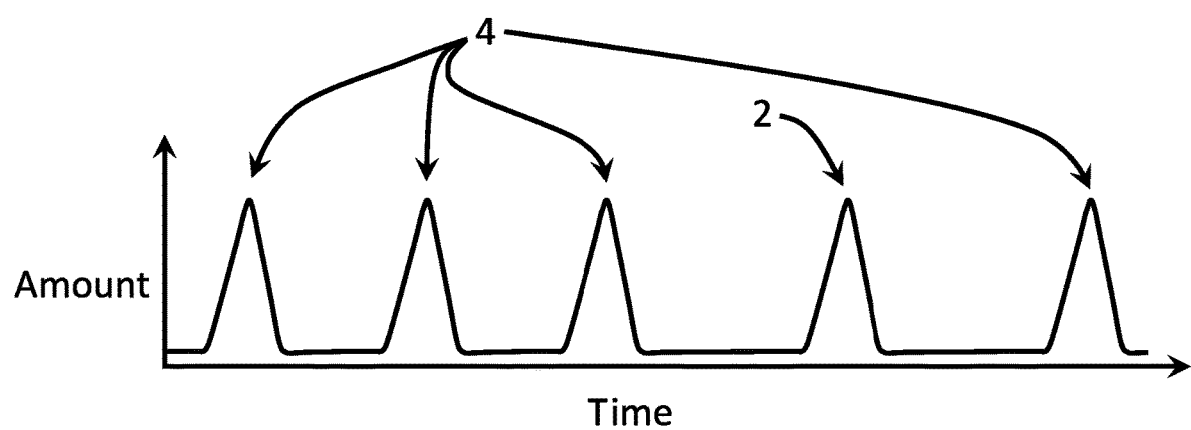
FIG. 2 is a chart showing schematic, time resolved streams of a reference material and an analyte.

Carrier gas streams (or flows) are useful for analytes and/or reference materials having vapor pressures too low to be introduced into the first introduction device as a gas, and/or for analytes and/or reference materials that have been separated by a gas chromatograph or liquid chromatograph prior to being analyzed with the apparatus, systems or methods disclosed herein. When the analyte and/or reference material are provided to the first introduction device entrained in a carrier gas flow, the mixing ratio of the analyte to the carrier gas and the mixing ratio of the reference material to the carrier gas can be held constant (or generally constant). Variations in the mixing ratios result in increased errors in the data obtained from the carrier gas flows, relative to data obtained from the gas phase analyte and the gas phase reference material. The analyte or the reference material can be provided to the first introduction device 212 as a time resolved pulse. For example, FIG. 2 is a graph showing schematic, time resolved pulses of reference material entrained in carrier gas 4 bracketing a time resolved pulse of analyte entrained in a carrier gas flow 2. As described in more detail below, measurements of the analyte can be bracketed by measurements of the reference material to correct for various errors. In FIG. 2, the peak shapes shown are schematic. In actual analyses, the flow rate of gas to the ion source will be controlled such that several seconds of relatively stable signal is observed at the middle of each peak. For example, FIG. 7 includes data from actual analyses.

Figure 3:
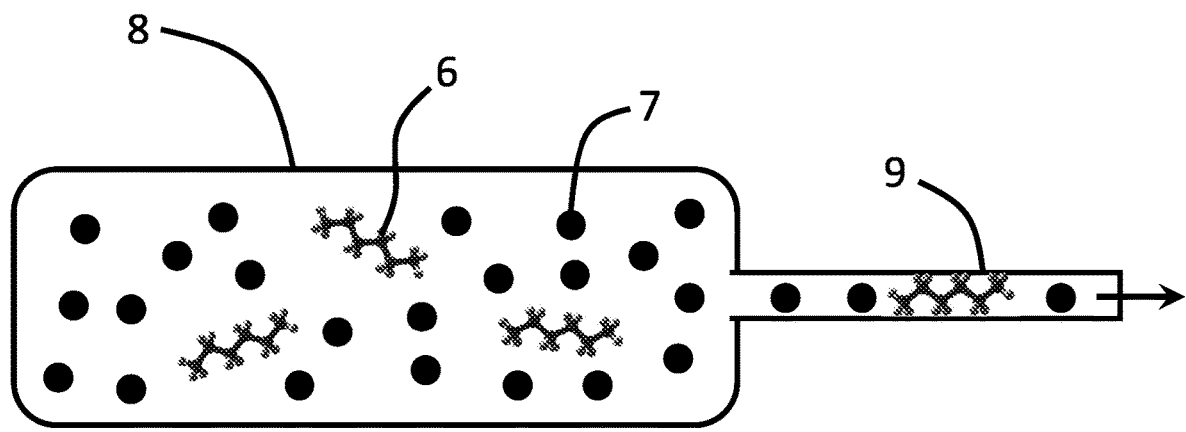
FIG. 3 is schematic view of a mixture of an inert gas and an analyte.

High molecular weight and/or low vapor pressure materials (e.g., low boiling point liquids) can be analyzed at low temperature (e.g., room temperature) using an inert gas to push the analyte into the first introduction device. For example, such an analyte can be cryofocused (or cryopumped) into an evacuated container (e.g., a tube under vacuum) by connecting the container, which is under vacuum, to another container including a sample. The container can then be cooled (e.g., by contacting it with liquid nitrogen or another cold material) to condense (or freeze) the analyte in the container. The container can then be disconnected from other container, filled with an inert gas, and warmed to a higher temperature (e.g., room temperature). The analyte and the inert gas can then be mixed (or thoroughly mixed) and the mixture can be allowed to expand into yet another container (e.g., a bellows). The inert gas can then "push" the analyte through a conduit to the first introduction device. For example, FIG. 3 shows an analyte 6 mixed with an inert gas 7 in a container 8 (e.g., a bellows) being transmitted through a conduit 9 (e.g., a capillary) to the first introduction device 212.

In the embodiment shown in FIG. 1, the first introduction device 212 is configured to provide the first portion of the analyte and the reference material to the first ion source 216 via a conduit 214. In some embodiments, the sample reservoir 202, reference reservoir 204, conduit 206, conduit 208, conduit 210, first introduction device 212, and/or conduit 214 can be heated to facilitate introduction of the analyte and/or reference material to the first ion source 216.

The first ion source can be any suitable ion source used for mass spectrometry, and can be the second ion source described in more detail below with respect to a second mass spectrometer. In some embodiments, the first mass spectrometer includes an inlet system and first introduction device of a gas source mass spectrometer (e.g., an inlet system and changeover block from a Thermo Delta V mass spectrometer, available from Thermo Fisher Scientific, Inc., Waltham, Mass.) modified to be coupled to an ion source of a reverse geometry, single collector gas source mass spectrometer capable of achieving extremely high mass resolutions such as 100,000 (e.g., a Thermo DFS mass spectrometer, available from Thermo Fisher Scientific, Inc., Waltham, Mass.). For example, in one embodiment of the first mass spectrometer, the inlet system and changeover block from a Thermo Delta V mass spectrometer was combined with a Thermo DFS mass spectrometer by connecting an outlet of the changeover valve block of the Thermo Delta V mass spectrometer to an aperture (e.g., a small aperture) on a side of the ion source of the Thermo DFS mass spectrometer. In that embodiment, the connection was made through a vacuum housing of the Thermo DFS mass spectrometer using a connector that abuts the side of the ion source of the Thermo DFS mass spectrometer (e.g., the connector ends at a point flush with the side having the aperture). The connector may be a stainless steel tube (e.g., a ⅛" stainless steel tube) machined to connect the changeover valve block of the Thermo Delta V mass spectrometer and the aperture on the side of the ion source of the Thermo DFS mass spectrometer.

In FIG. 1, the first ion source 216 is configured to convert the first portion of the analyte (or other materials, such as the various reference materials described below) to ions (e.g., first molecular analyte ions). The first ion source 216 produces the ions as a first output (e.g., the first molecular analyte ions). As the ions exit the first ion source 216, they encounter the first entrance slit 239, which can be included as a component of the first ion source 216 or can be separately connected to the first ion source. The first entrance slit 239 can be configured to guide the first molecular analyte ions along the first ion travel path.

The first momentum filter 222 can be positioned along the first ion travel path downstream from the first entrance slit 239 and can be configured to receive the first molecular analyte ions via a conduit 218. The first momentum filter can have a first radius of curvature along the first ion travel path and can be configured to filter out second molecular analyte ions from the first molecular analyte ions according to their momenta and produce a second output of molecular analyte ions. The first momentum filter can be any suitable device that can filter ions according to their momenta, such as a magnetic sector. For example, the first momentum filter can be the momentum filter of a Thermo DFS mass spectrometer, available from Thermo Fisher Scientific, Inc., Waltham, Mass.

The first mass spectrometer can also include tuning optics to guide the analyte ions through the first mass spectrometer. For example, a first ion focusing element 220 can be included along the first ion travel path between the first ion source 216 and the first momentum filter 222 (e.g., the first ion focusing element 220 can be included in the conduit 218). The first ion focusing element 220 may focus the second molecular analyte ions along the first ion travel path to the first momentum filter 222. The first focusing element can be any suitable device capable of focusing the second molecular analyte ions, such as an electrostatic or magnetic lens (e.g., a quadrupole or higher format lens), for example, an ion focusing element of a Thermo DFS mass spectrometer, available from Thermo Fisher Scientific, Inc., Waltham, Mass.

The first energy filter 228 can be positioned along the first ion travel path downstream from the first ion source 216, the first entrance slit 239, the first ion focusing element 220 and the first momentum filter 222, and can be configured to receive the second molecular analyte ions, which have energy levels, via a conduit 224. The first energy filter 228 can have a second radius of curvature along the first ion travel path and can be configured to filter out third molecular analyte ions from the second molecular analyte ions according to their energy levels and produce a third output of molecular analyte ions. The first energy filter can be any suitable device that can filter ions according to their energy levels, such as an electrostatic analyzer. For example, the first energy filter can be the energy filter of a Thermo DFS mass spectrometer, available from Thermo Fisher Scientific, Inc., Waltham, Mass.

A second ion focusing element 226 can be included along the first ion travel path between the first momentum filter 222 and the first energy filter 228 (e.g., the second ion focusing element 224 can be included in the conduit 224). The second ion focusing element 226 may focus the second molecular analyte ions along the first ion travel path to the first energy filter 228. The second ion focusing element can be any suitable device capable of focusing the second molecular analyte ions, such as an electrostatic or magnetic lens (e.g., a quadrupole or higher format lens).

A third ion focusing element 232 can be included along the first ion travel path between the first energy filter 228 and the detector 234. The first energy filter 228 can be coupled to the detector by a conduit 230, and the third ion focusing element 232 can be included in the conduit 230. The third ion focusing element 232 may focus the third molecular analyte ions along the first ion travel path to the detector 234. The third ion focusing element can be any suitable device capable of focusing the third molecular analyte ions, such as an electrostatic or magnetic lens (e.g., a quadrupole or higher format lens), for example, an ion focusing element of a Thermo DFS mass spectrometer, available from Thermo Fisher Scientific, Inc., Waltham, Mass.

The detector 234 can be positioned downstream of the first energy filter 228 (and the third ion focusing element 232) and can be configured to receive the third molecular analyte ions. The detector 234 can be any suitable device used for detecting ions, such as the detector of a Thermo DFS mass spectrometer, available from Thermo Fisher Scientific, Inc., Waltham, Mass. The detector 234 can be a single or sole detector.

The first mass spectrometer 200 can be configured to provide the third molecular analyte ions to the detector 234 at a first mass resolution (which is described in more detail below) of 30,000 or greater (e.g., from 30,000 to 100,000; from 49,000 to 100,000; or from 80,000 to 100,000). For example, the first width of the first entrance slit 239 and the first and second radii of curvature of the first momentum filter and first energy filter can be selected to provide a first mass resolution at the detector 234 of 30,000 or greater (e.g., 49,000 or greater). The detector can be connected to a processor (or a first processor and a second processor) 236 (e.g., a computer or computers), which can be configured to acquire data from the detector and process the data. The processor can be a processor of a Thermo DFS mass spectrometer, available from Thermo Fisher Scientific, Inc., Waltham, Mass. As described in more detail below, the processor can also be configured to control various features of the mass spectrometer, such as the detector. For example, the processor 236 can be connected to any or all of the components of the first mass spectrometer 200, and can be used to control the operation of the components. In some embodiments, control of the first introduction device 212 and other peripherals by the processor 236 facilitates standardization of measurements on the first mass spectrometer 200. In some embodiments, some components of the first mass spectrometer 200 are controlled by processors separate from and in addition to the processor 236.

According to embodiments of the present invention, the first mass spectrometer can obtain a signal at one cardinal mass by setting a magnetic field strength of the first momentum filter to a set value corresponding to the cardinal mass of interest, and varying an electric field strength of the first energy filter to scan across the cardinal mass. For example, by holding the magnetic field strength of the first momentum filter constant (or generally constant) and varying the electric field strength of the first energy filter, the masses of ions that are detected at the detector can be varied across a range of one cardinal mass (or less).

Figure 4:
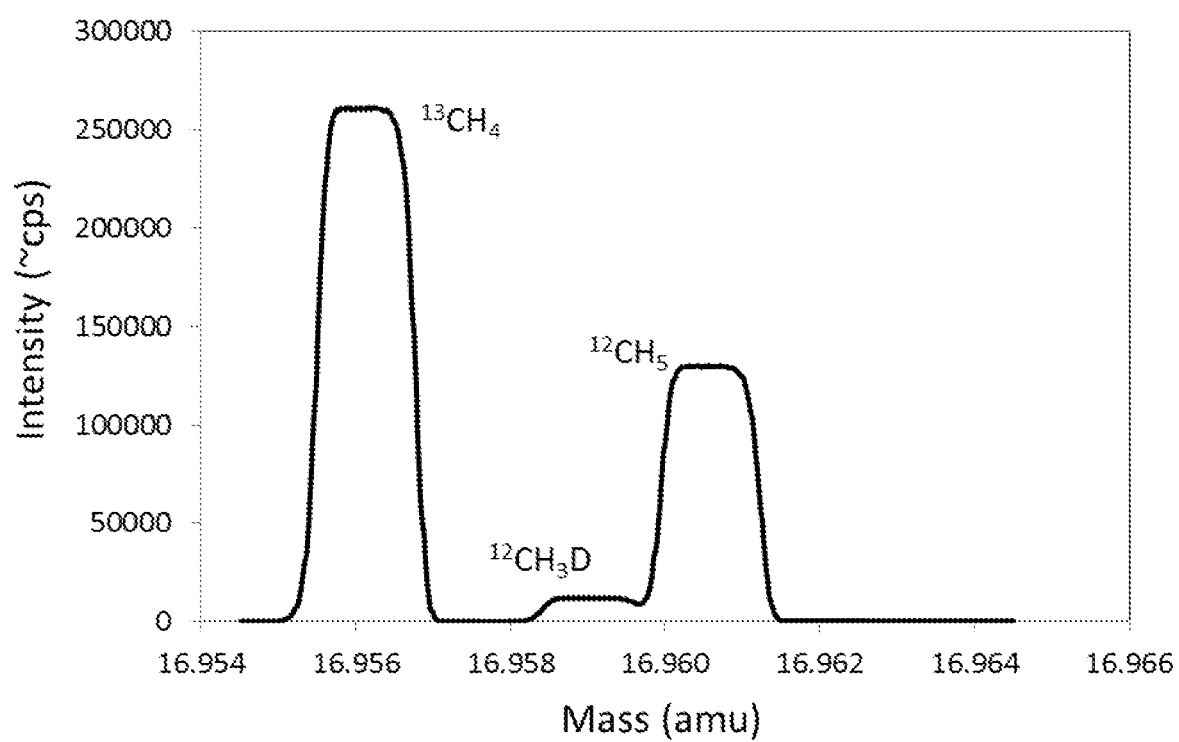
FIG. 4 is graph showing a mass spectrum obtained using a first mass spectrometer according to an embodiment of the present invention.
Figure 5:
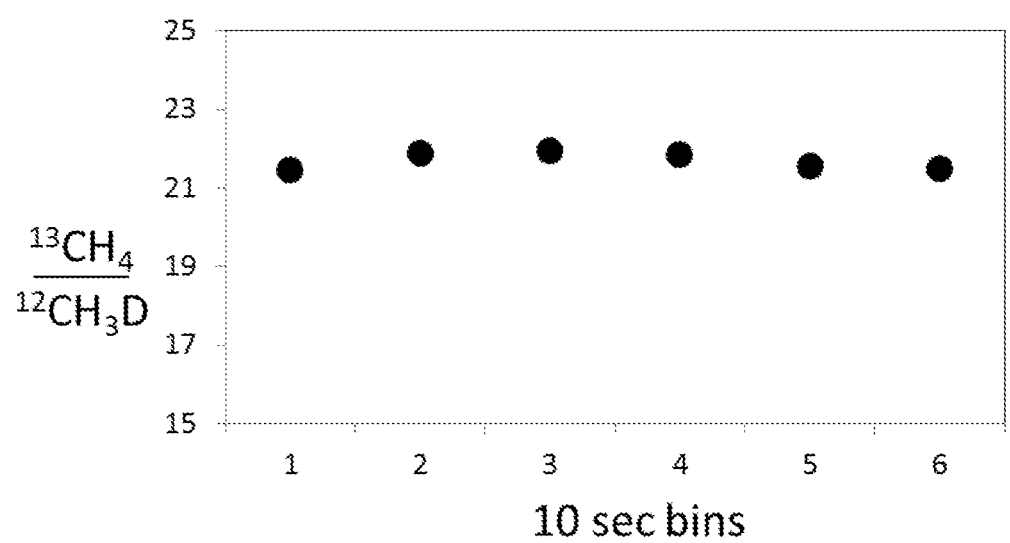
FIG. 5 is graph showing the precision of measurements of the intensity ratios of two of the ion beams illustrated in FIG. 4, made using a first mass spectrometer according to an embodiment of the present invention.

In some embodiments, the third molecular analyte ions include two or more first molecular analyte ion beams, and the detecting the two or more of the third molecular analyte ions includes scanning at least two of the first molecular analyte ion beams across a single detector. FIG. 4 is a graph showing a signal acquired at a cardinal mass of 17 amu using an embodiment of the first spectrometer. The peak shapes shown in FIG. 4 are generated by repeatedly scanning the three labeled ion beams corresponding to the respective peaks across an exit slit of the first mass spectrometer, through subtle, cyclical adjustments of the potential (e.g., electric potential) of the first energy filter, during a period when the delivery of analyte to the ion source is relatively stable over time. The exit slit leads to the detector, and, in some embodiments, ions that pass through the exit slit are registered on a single detector. For example, in FIG. 4, signals corresponding to $^{13}CH_4$, $^{12}CH_3D$, and $^{12}CH_5$ were acquired by holding the magnetic field strength of the first momentum filter generally constant and varying the electric field strength of the first energy filter to vary the mass of the ions detected at the detector at a cardinal mass of 17 amu. Additionally, the signals shown in FIG. 4 were acquired by cycling the electric field strength of the first energy filter to produce a plurality of scans at the cardinal mass of 17 amu. By acquiring a plurality of scans, data having high reproducibility and low error can be obtained. For example, FIG. 5 is graph showing that the ratio of $^{13}CH_4$ to $^{12}CH_3D$ (as shown in FIG. 4) can be acquired with 1 standard deviation (1 sd)=1%, and 1 standard error (1 se) could approach 1‰ after a few minutes of data acquisition.

Figure 6:
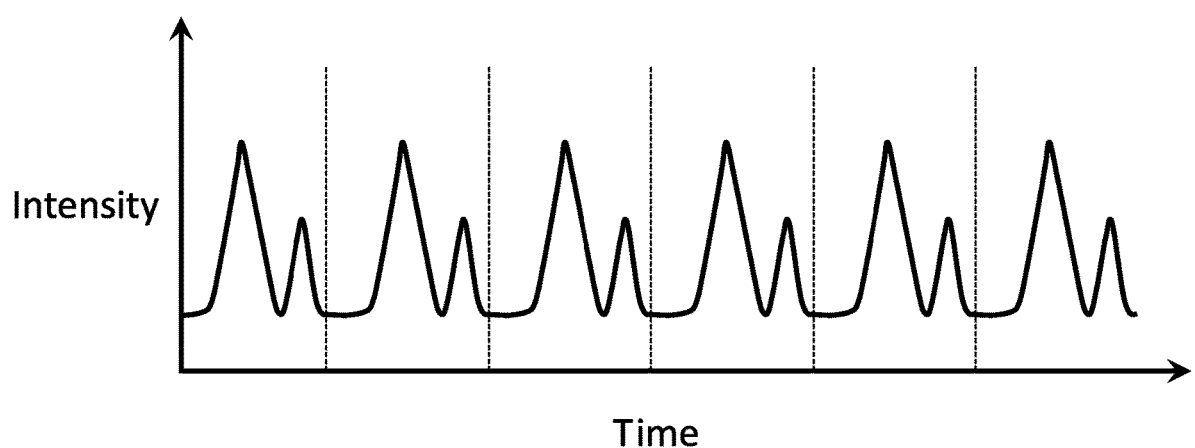
FIG. 6 is a schematic chart showing cycles of mass spectra obtained using a first mass spectrometer according to an embodiment of the present invention.

If the electric field strength of the first energy filter is not cycled to produce a plurality of scans, signals having relatively smaller intensities and/or signals that are close to other signals from isobaric ions may be difficult to detect. Accordingly, in embodiments of the present invention, the first mass spectrometer is configured to vary the strength of the first electric field of the energy filter in a set range to vary the masses of the third molecular analyte ions detected at the detector in a range spanning one atomic mass unit. For example, FIG. 6 is a schematic chart showing a plurality of scans (or sweeps) acquired by cycling the electric field strength of the first energy filter over time. In FIG. 6, each of the scans is separated by a broken line. The scans acquired through cycling (e.g., rhythmic cycling) of the electric field strength of the first energy filter can be averaged together (e.g., "signal-averaged") to obtain high quality data that can be modeled (e.g., using a "peak-fitting" algorithm, such as those described in U.S. Provisional Application No. 61/869,461, the entire contents of which are incorporated herein by reference) and then analyzed using the methods described in more detail below and/or the algorithms described in U.S. Provisional Application No. 61/869,461. In some embodiments, the scans acquired through cycling the electric field strength of the first energy filter can each be modeled (e.g., using a "peak-fitting" algorithm, such as those described in U.S. Provisional Application No. 61/869,461) and the resultant models can be averaged together (e.g., "model-averaged") to obtain high quality data that can then be analyzed using the methods described in more detail below and/or the algorithms described in U.S. Provisional Application No. 61/869,461. Over the period of time illustrated in FIG. 6, the magnetic field of the first momentum filter is fixed (or set) and the delivery of analyte to the first ion source is approximately constant, but the potential (e.g., electric potential) of the first energy filter varies cyclically over a narrow range, causing two closely adjacent ion beams (one large, the other small) to be scanned across the exit slit and measured with the detector. Dashed lines mark the end of one cycle of first energy filter potential adjustment and the start of another. Stacking (or adding) these periodic signals together yields a peak shape such as that shown in FIG. 4.

Figure 7:
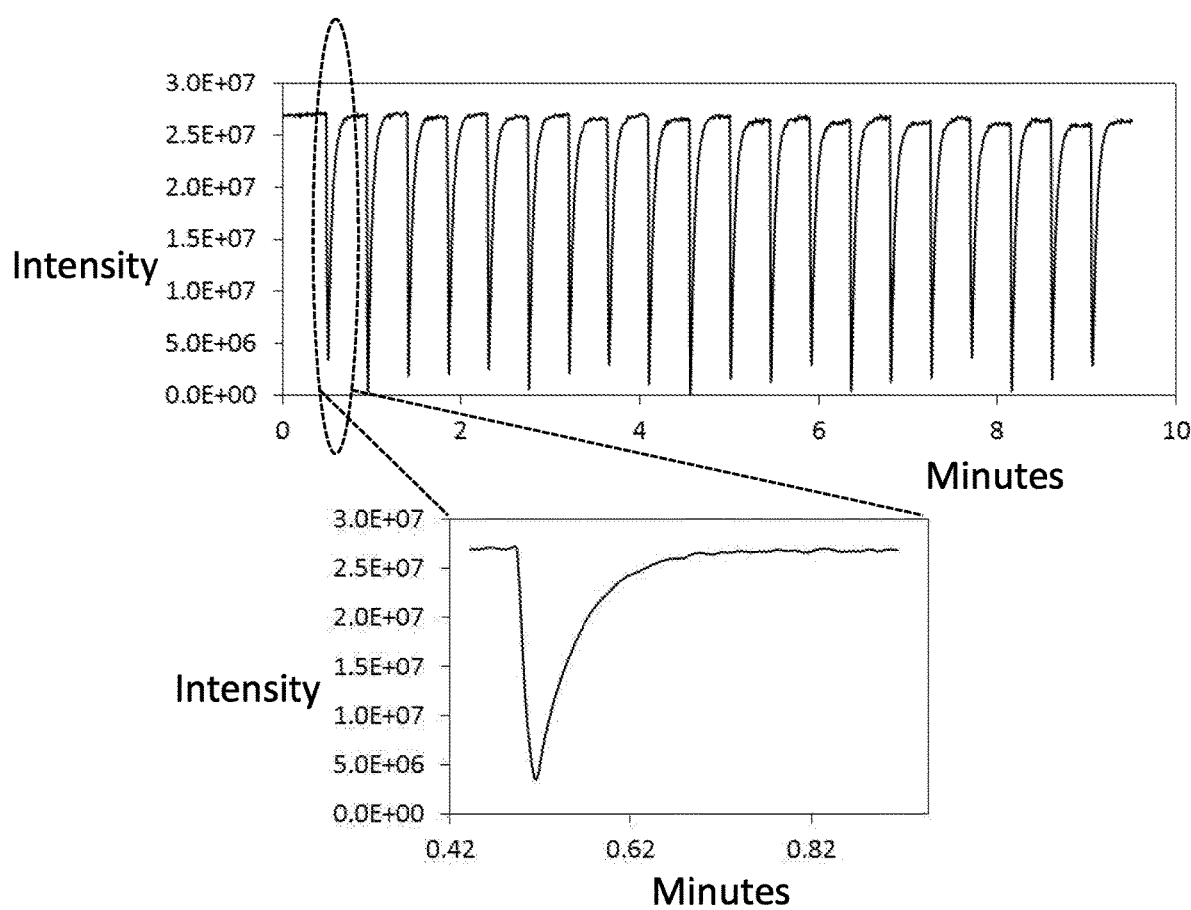
FIG. 7 is a graph, including a close-up view, showing signal intensities generated when pulses of methane are introduced into a first mass spectrometer according to an embodiment of the present invention.
Figure 8:
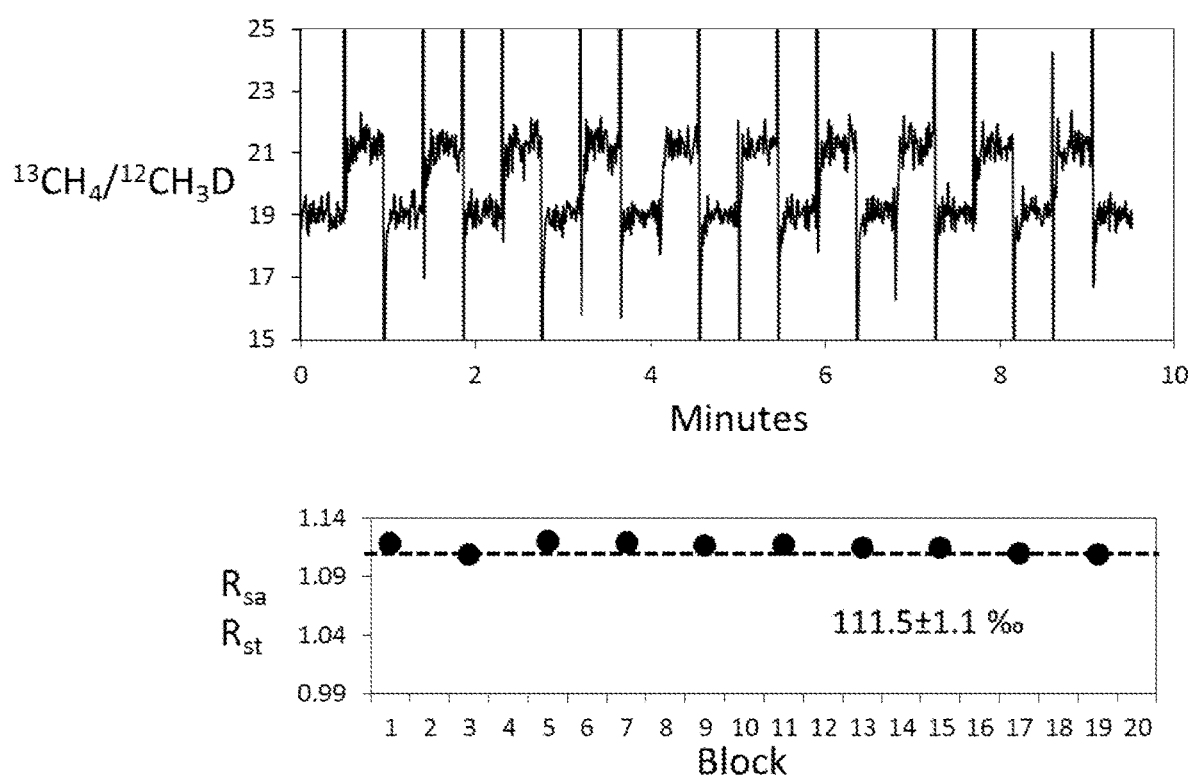
FIG. 8 is a pair of graphs in which the upper graph is a time series of measurements of the ratios of two peaks at 17 amu for methane, where each relatively flat portion of the time trace samples either the sample or standard and the spikes are the ratios measured during the intensity dips shown in FIG. 7, and the lower graph shows averages across the flat parts of each block of data and compares each sample period to the bracketing standard periods.

While the electric field of the first energy filter is being cycled, the first mass spectrometer can switch between the analyte (e.g., the sample), the reference material (e.g., the standard), or another analyte. For example, embodiments of the first introduction device (e.g., a first introduction device having a dual inlet) can provide results having good stability and low error, even when switching between the various materials. For example, FIG. 7 is a graph, including a close-up view of the circled portion, showing performance of an embodiment of the first introduction device of the first mass spectrometer while monitoring the $^{13}CH_4$ signal for 10 mbar of methane in the sample bellows ($10^{-7}$ mbar at the ion source), where the e-folding times were 0.6 second on fall and 8 second on rise, and the signal stability was about $2 \times 10^{-3}$ ($1\sigma$, 1 sec bins). In FIG. 7, the signal intensities are generated from pulses of methane introduced into a first mass spectrometer according to an embodiment of the present invention, where valves controlling the flow of methane from either the sample or reference standard reservoirs are cycled, alternating flow from one or the other into the ion source. Each peak top is produced by the relatively intense, stable signal of a steady flow of one or the other gases into the first ion source, and each dip is produced when flow is interrupted by cycling of the valves that regulate gas flow. In FIG. 7, intensity is integrated across all masses in the mass scan from FIG. 4, yielding the total ion current per scan. FIG. 8 is a pair of graphs demonstrating the performance of an embodiment of the first introduction device of the first mass spectrometer for a sample/standard comparison while monitoring the $^{13}CH_4/^{12}CH_3D$ ratio. The upper graph in FIG. 8 shows a time series of measurements of the ratios of two peaks at 17 amu for methane, where each relatively flat portion of the time trace samples either the sample or standard and the spikes are the ratios measured during the intensity dips in FIG. 7. The lower graph in FIG. 8 shows averages across the flat parts of each block of data and compares each sample period to the bracketing standard periods. The data presented in FIGS. 7 and 8 was acquired using an embodiment of the first mass spectrometer that can obtain precision of ±0.4 to 2% and 1 s.e. (which is common for an acquisition of about 10 minutes) across range of analytes, mass resolutions and peak shapes (generally ~1-2× counting statistics). While there may still be some variation and/or error in data obtained when switching materials (e.g., analyte and standard), such data can be discarded, if desired.

Embodiments of the first mass spectrometer can also acquire data at different cardinal masses. For example, the first mass spectrometer can acquire data at one cardinal mass using generally the same methods as described above, and then the first momentum filter can be set to another magnetic field strength to acquire data at another cardinal mass by varying the electric field strength of the first energy filter as described above. Thus, once data has been acquired at one cardinal mass, the first mass spectrometer can transition (or hop) to detecting ions at another cardinal mass using generally the same procedures as those described above. Because embodiments of the first mass spectrometer detect ions (e.g., the third molecular analyte ions) at one cardinal mass at a time, comparisons between data acquired at different cardinal masses can be made from separate, non-concurrent (or non-simultaneous) measurements. While such comparisons can be made, those comparisons have a relatively high degree of error, unless they are supplemented with data acquired using another apparatus, such as a second mass spectrometer, embodiments of which are described in more detail below.

Figure 9:
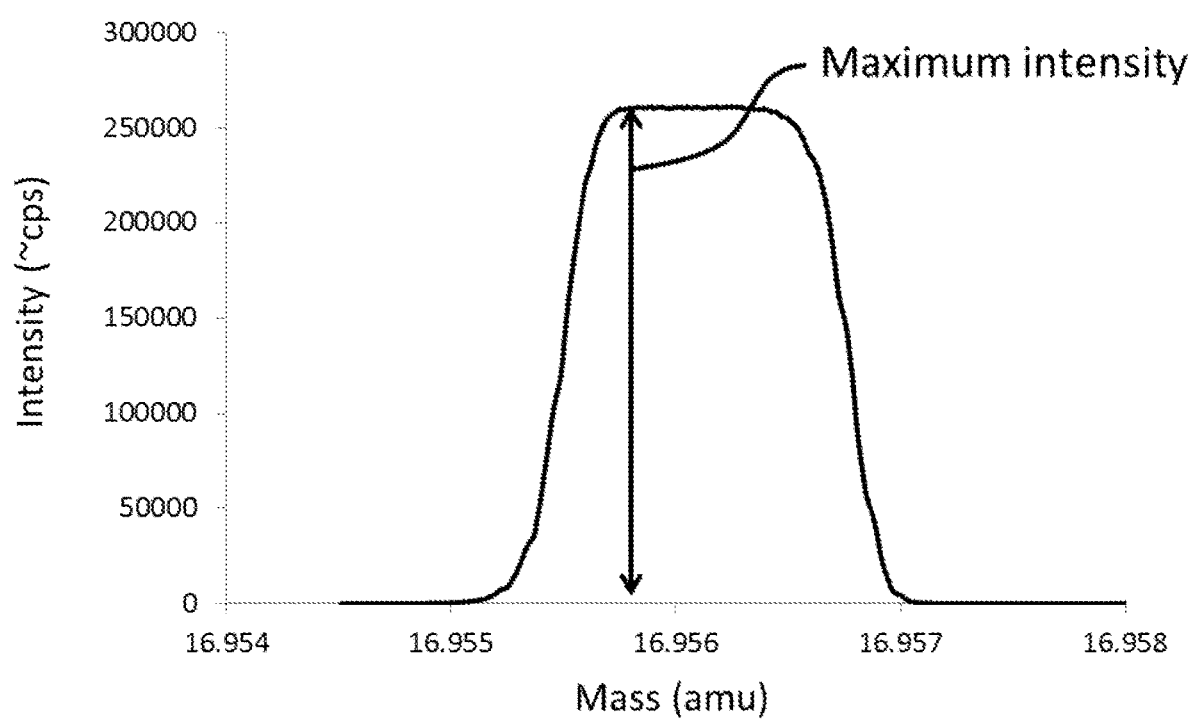
FIG. 9 is a graph showing analysis of a mass spectrum obtained using a first mass spectrometer according to an embodiment of the present invention.
Figure 10:
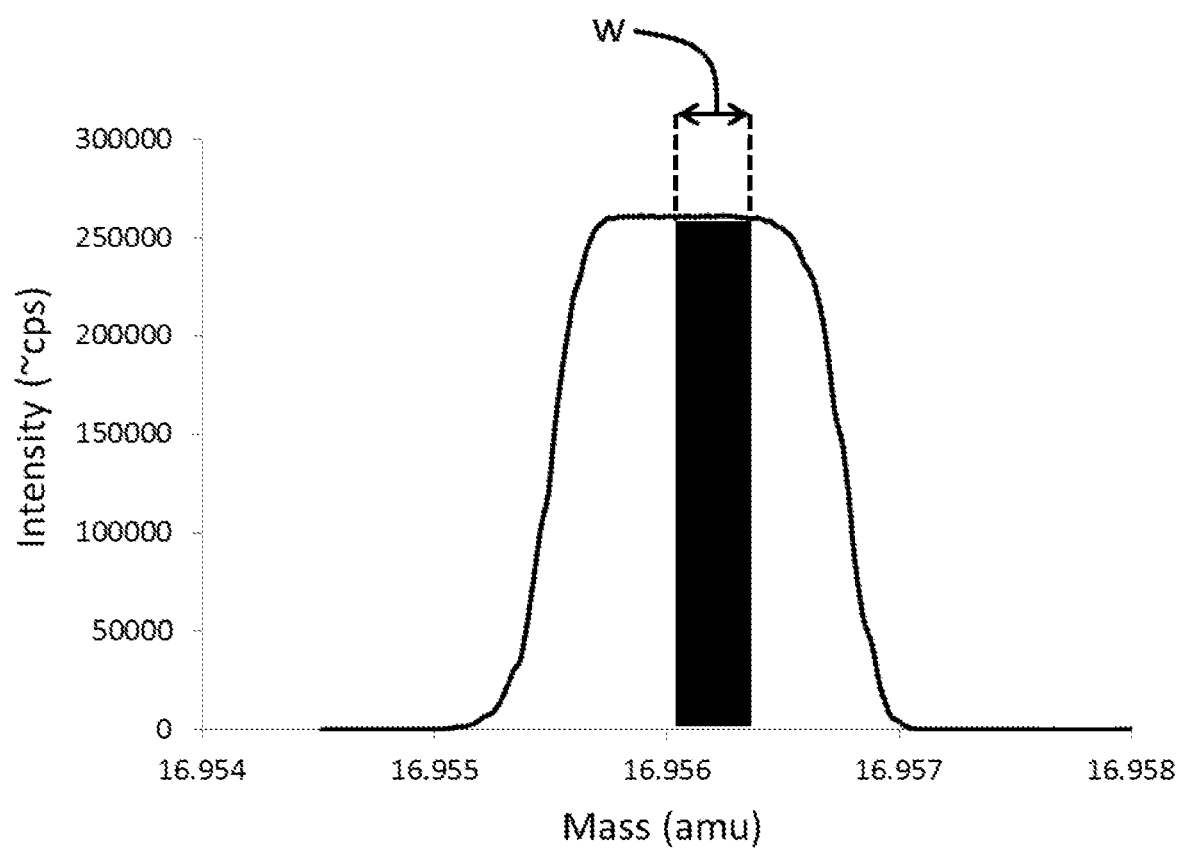
FIG. 10 is a graph showing analysis of a mass spectrum obtained using a first mass spectrometer according to an embodiment of the present invention.
Figure 11:
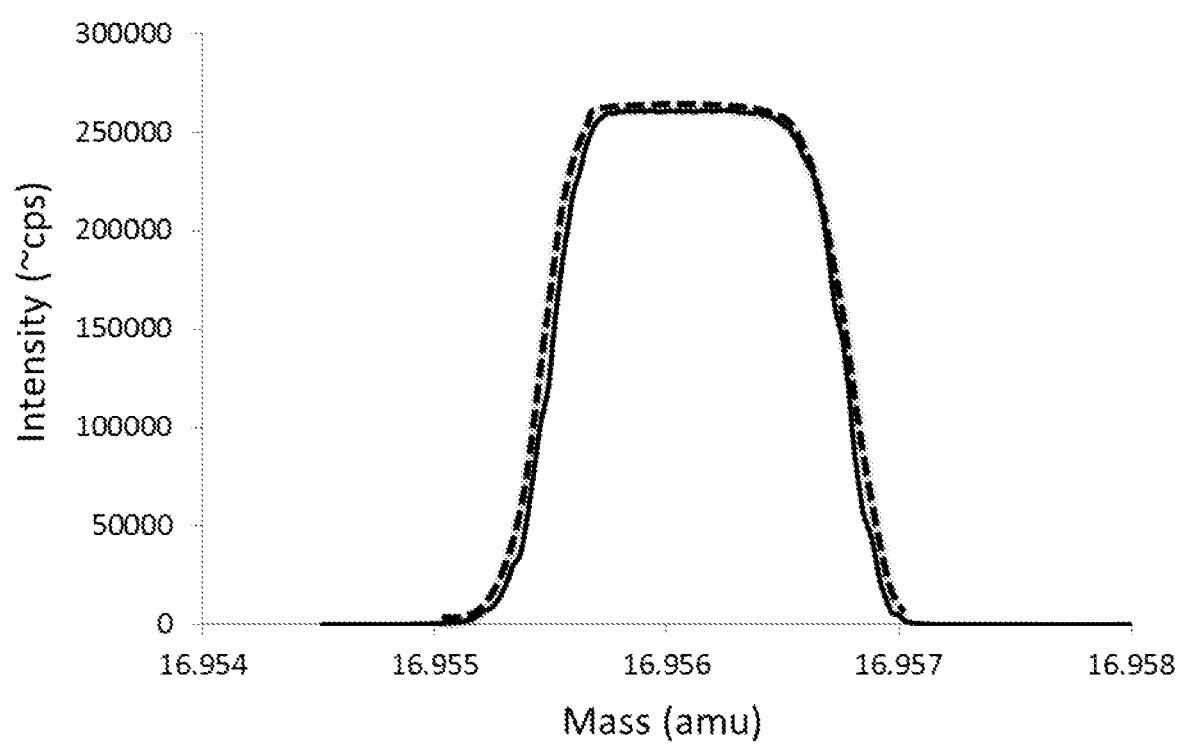
FIG. 11 is a graph showing analysis of a mass spectrum obtained using a first mass spectrometer according to an embodiment of the present invention.

Data collected using an embodiment of the first spectrometer can be analyzed in a variety of ways, some of which are illustrated by FIGS. 9-11. One embodiment of a method for recording the intensity of one ion beam (e.g., one ion beam of the third molecular analyte ions) in one scan is to record the maximum intensity observed as part of the peak of that ion beam. For example, in FIG. 9, the data is analyzed by measuring the maximum signal intensity detected. Another embodiment of a method for recording the intensity of one ion beam in one scan is to average the intensity observed across a portion (e.g., a range) of the peak of that ion beam. The portion of the peak that is averaged may generally be chosen to be the most intense and/or flattest portion of the peak. For example, in FIG. 10, the data is analyzed by integrating over a mass range w. Another embodiment of a method for recording the intensity of one ion beam in one scan is to create a forward model of the shape of the peak, where the first entrance slit width and exit slit width and ion beam intensities are model parameters, and to adjust those parameters to achieve the best statistical fit to the measured peak shape. For example, in FIG. 11, the broken line represents a peak shape model that is fit to the data. As described above, the peak shape model can be fit to a series of scans that have been averaged ("signal averaging"), or the peak shape model can be fit to each of a series of scans and the models can be averaged ("model averaging"). Measuring the maximum intensity, as shown in FIG. 9, is the least labor intensive analysis, but it provides relatively lower precision than the other methods shown. Integrating over a mass range, as shown in FIG. 10, provides the best compromise of convenience and precision among the methods shown. The model averaging approach of FIG. 11 provides the most precise results for complex, rounded peaks. The methods of FIGS. 10 and 11 generally yield similar ion intensity ratios across a range of peak shapes.

Embodiments of the present invention are also directed to systems that include the first mass spectrometer disclosed herein and a second mass spectrometer. U.S. patent application Ser. No. 13/656,447, filed on Oct. 19, 2012, entitled HIGH-RESOLUTION MASS SPECTROMETER AND METHODS FOR DETERMINING THE ISOTOPIC ANATOMY OF ORGANIC AND VOLATILE MOLECULES, the entire contents of which are incorporated herein by reference, discloses a mass spectrometer (referred to herein as "the second mass spectrometer") capable of analyzing singly and multiply substituted isotopologues of methane, higher order alkanes and other organic molecules at mass resolutions (M/ΔM) as high as 27,000, which is sufficient to discriminate among the complex sets of isobaric interferences that occur for molecular ions of organic compounds (e.g., to discriminate between $^{13}CH_4$, $^{12}CH_3D$, and $^{12}CH_5$, each of which have a mass of 17 atomic mass units). One embodiment of the second mass spectrometer is a gas source, double focusing, high resolution multi-collector instrument.

In some embodiments, the second mass spectrometer includes the inlet system of a gas source isotope ratio mass spectrometer (e.g., the Thermo IRMS 253, available from Thermo Fisher Scientific, Inc., Waltham, Mass.) and an analyzer and detector array resembling those of the most sophisticated plasma and thermal mass spectrometers (e.g., the Thermo Neptune, available from Thermo Fisher Scientific, Inc., Waltham, Mass.). In some embodiments, the second mass spectrometer is a dual-inlet, multi-collector instrument capable of precision and accuracy sufficient for applied stable isotope geochemistry (e.g., ±0.01 to 0.10%).

The combination of components and capabilities of embodiments of the second mass spectrometer, which are described in more detail below, provide a mass spectrometer capable of directly and precisely analyzing the stable isotopic compositions of organic molecules in their original structural forms, rather than after chemical or thermal decomposition to $H_2$, CO or $CO_2$. For example, embodiments of the second spectrometer can concurrently (or simultaneously) detect ions at more than one cardinal mass. Additionally, because the second mass spectrometer is capable of analyzing the "original structure" of an analyte (e.g., molecular ions that retain molecular or moiety stoichiometry of the analyte), the analyte can be meaningfully analyzed for multiply substituted (or "clumped") isotopic species. Furthermore, the second mass spectrometer is capable of analyzing fragments of the analyte. Because organic compounds (e.g., the analyte) fragment in distinctive ways under electron bombardment, the second mass spectrometer is capable of performing measurements on pieces or fragments of analyte molecules, which allows for reconstruction of position-specific isotopic anomalies of the analyte. Through study of multiply substituted fragment ions the second mass spectrometer can be used to produce position-specific clumped isotope measurements. The capabilities of the second mass spectrometer allow for new isotopic approaches to the study of organic geochemistry, including the temperatures of generation and/or storage of natural gases and oils, the mechanisms of biosynthetic and maturation reactions, among other applications.

The second mass spectrometer has a demonstrated ability to measure abundances of singly and doubly substituted isotopologues of methane, ethane and propane. Such measurements enable several new geochemical tools, including a "clumped isotope" thermometer for methane based on the reaction: $^{12}CH_3D + ^{13}CH_4 \leftrightarrow ^{13}CH_3D + ^{12}CH_4$, which is described in more detail below. Clumped isotope geochemistry of organic compounds is capable of improving the understanding of the origins of natural gases, methane biogeochemistry, and the like. The second mass spectrometer can also precisely analyze the isotopic compositions of fragments of propane, permitting determination of differences in $\delta^{13}C$ between central and terminal carbon positions.

The second mass spectrometer can also measure doubly $^{13}C$-substituted ethane ($^{13}C_2H_6$). Such measurement of propane and ethane serve as a model for mass spectrometric study of the carbon isotope anatomies of molecular structures of other organic compounds, which can be used to study temperatures of formation and storage, compositions of organic matter in source rocks, and the mechanisms of maturation reactions, all of which are relevant to oil and gas exploration. The above-described features of the second mass spectrometer are, on their own, sufficient for analysis of low-molecular weight alkanes. For example, simple models of the expected mass spectra for other target analytes can be used to develop similar measurements of isotopologues of butane, pentane and hexane.

The second mass spectrometer can detect ions with m/z up to ~300 atomic mass units ("amu") and, therefore, it can be used in the study of the organic chemistry of high-molecular weight components of oils, biomass and other organic materials.

Figure 12:
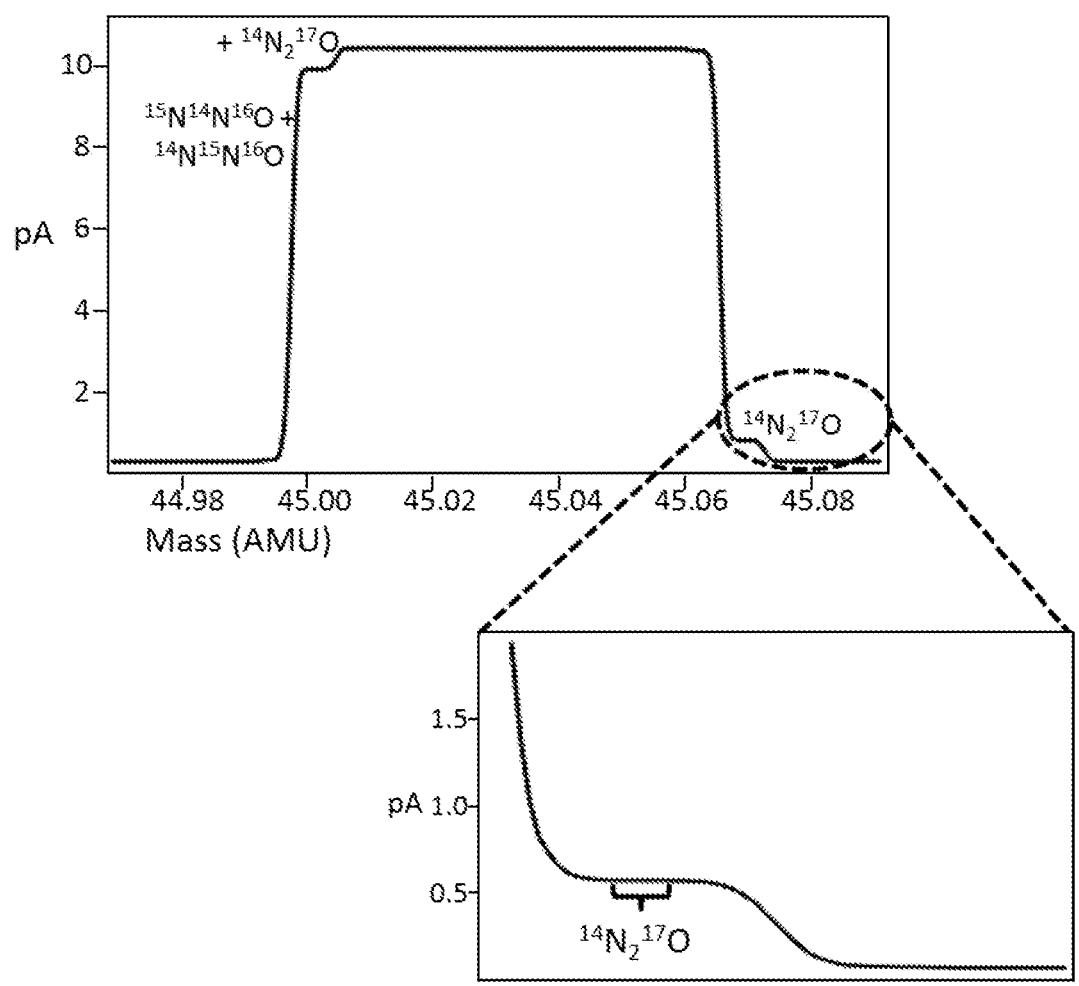
FIG. 12 is a graph, including a close-up view, showing a mass spectrum obtained using a second mass spectrometer according to an embodiment of the present invention.

One embodiment of the second mass spectrometer (the ThermoFisher IRMS 253-Ultra) has sufficiently high mass resolution to fully separate ion beams that are nearly adjacent, provided their mass is sufficiently low and/or mass separation sufficiently large. For example, FIG. 12 is a graph showing data acquired for N2O using an embodiment of the second mass spectrometer at medium resolution (16 μm wide entrance slit; M/ΔM=17,800). The data shown in FIG. 12 was acquired using a normal geometry, multi-collector sector mass spectrometer capable of resolving some nearly isobaric isotopologues from one another, provided that their respective masses are relatively low and/or mass separation of the isotopologues is relatively large. In FIG. 12, the signal corresponding to $^{14}N_2^{17}O$ is easily discernible from the signal corresponding to $^{14}N^{15}N^{16}O$ and $^{15}N^{14}N$, and as can be seen in the close-up view of the portion of the graph encircled with a broken line, the portion of the signal corresponding to $^{14}N_2^{17}O$ that is indicated with the bracket is statistically flat (30 BDAC units; ~0.001 AMU) and easily discernible.

Figure 13:
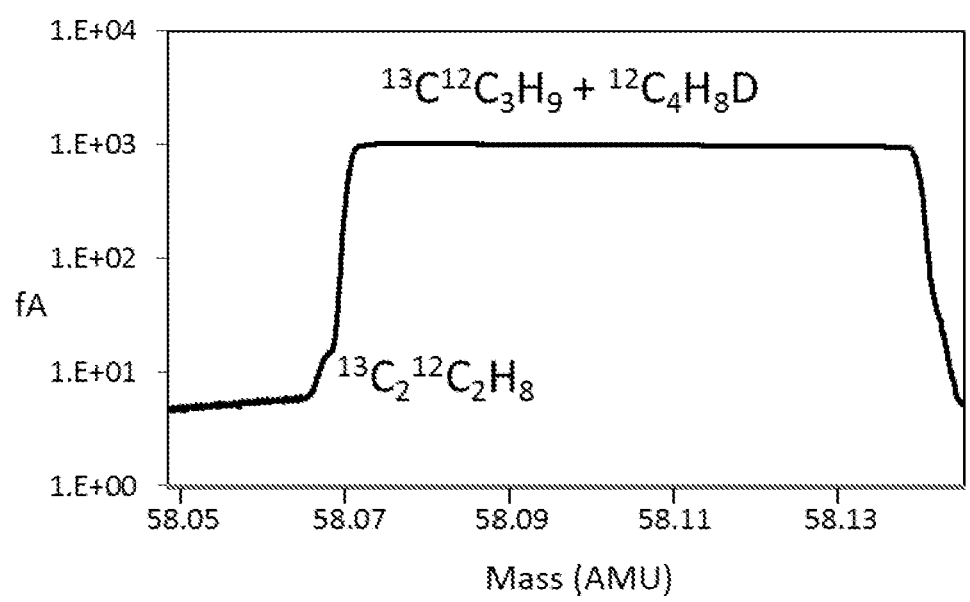
FIG. 13 is a graph showing a mass spectrum obtained using a second mass spectrometer according to an embodiment of the present invention.

One embodiment of the second mass spectrometer is capable of measuring ions having masses up to 300 amu. Even at such high masses, the mass resolution of the second mass spectrometer is sufficient to discriminate between analytes and isobaric interferences from other molecular species (e.g., contaminants). For example, $^{13}C^{12}C_9H_{22}$ ($^{13}C$ substituted decane; having a mass of 143.1755 amu) can be resolved from $^{12}C_5^{16}O_5H_3$ (a prophetic fragment ion from carbohydrate or recombination product having a mass of 142.998 amu) using a mass resolving power of only about 800. Although contaminants that differ in chemical stoichiometry from the analyte (or analyte ions) are relatively easier to separate from the analyte ions, isotopologues of the same chemical species (e.g., $^{13}C$ substituted decane, i.e., $^{13}C^{12}C_9H_{22}$, and D substituted decane, i.e., $^{12}C_{10}H_{21}D$) are substantially more difficult to separate from one another. For example, FIG. 13 is a graph showing data acquired for hexane using an embodiment of the second mass spectrometer at high resolution (5 μm wide entrance slit; M/ΔM=22,500). As can be seen in FIG. 13, the signals corresponding to $^{13}C^{12}C_3H_9$ and $^{12}C_4H_8D$ are not well resolved from one another, and the contributions of each of $^{13}C^{12}C_3H_9$ and $^{12}C_4H_8D$ to the measured signal are not easily discernible. The data shown in FIG. 13 was acquired using a normal geometry, multi-collector sector mass spectrometer that is incapable of fully or partially resolving some nearly isobaric isotopologues from one another when mass is relatively high and/or mass separation relatively small. In cases where the signals corresponding to different isotopologues are not fully resolved from one another, according to embodiments of the methods described herein, the sum of the intensities of the closely adjacent peaks can be measured, and those intensities can be separated into their component parts using data acquired from the same sample on an embodiment of the first mass spectrometer. A mass resolving power of 49,000 (M/ΔM) can be used to distinguish $^{13}C$-substituted decane from D-substituted or H-adducted versions of $^{12}C$-decane. Embodiments of the second mass spectrometer, however, have a mass resolving power of less than 49,000 (M/ΔM), and the present inventor believes that any multi-collector, normal geometry sector mass spectrometer likely will not be able to achieve a mass resolving power of 49,000 (M/ΔM).

In contrast to embodiments of the second mass spectrometer, embodiments of the first mass spectrometer disclosed herein are capable of achieving mass resolutions up to 80-100,000 (M/ΔM) and thus can resolve closely adjacent ion beams that could not be resolved with embodiments of the second mass spectrometer. However, if the first mass spectrometer has only a single detector (e.g., a sole detector), precise analyses of ion intensity ratios can be made by scanning across a very narrow range in mass, and ion intensity ratios of species that share the same cardinal mass are measured together or concurrently. Accordingly, the $^{13}C$ and D rich forms of a high molecular weight compound such as decane can be separated from one another using an embodiment of the first mass spectrometer, but their abundance relative to $^{12}C$ or H forms would be measured using some other constraint.

Embodiments of the present invention are directed to the combination of data from the first and second mass spectrometers, so that their complementary traits (multi-collection at lower resolution; single collection at higher resolution) can both discriminate and quantify isotopologues of high molecular weight compounds.

Accordingly, aspects of embodiments of the present disclosure relate to the study of high molecular mass compounds (e.g., compounds having molecular masses greater than approximately 50 amu) through two separate, but related measurements. For example, in some embodiments the second mass spectrometer is used to precisely measure the relative abundances of ions (e.g., fragments ions) at each cardinal mass of an analyte, such as a high molecular mass analyte (e.g., at each cardinal mass, all isotopologue ions having the same cardinal mass are measured together or concurrently).

Accordingly, in some embodiments, in addition to analyzing an analyte from a sample using the second mass spectrometer, an analyte from the same sample is analyzed using an embodiment of the first mass spectrometer (e.g., a single-collector, reverse geometry mass spectrometer according to embodiments of the present disclosure). For example, the sample can be analyzed at very high mass resolving power (e.g., up to about 100,000) using the first mass spectrometer to establish the ratios of ion beams at each cardinal mass, and the relative abundances of the combination of closely-adjacent (e.g., nearly isobaric) ions at different cardinal masses can be precisely measured using the second mass spectrometer. By analyzing the sample at high mass resolving power with the first mass spectrometer, the proportions of the isotopologues that contribute to the signal intensity at each cardinal mass measured with the second mass spectrometer can be identified. Using this information, minor species can be "peak-stripped" from the signals measured with the second mass spectrometer, allowing for accurate calculation of the abundance of one isotopic species of interest measured with the second mass spectrometer.

Figure 14:
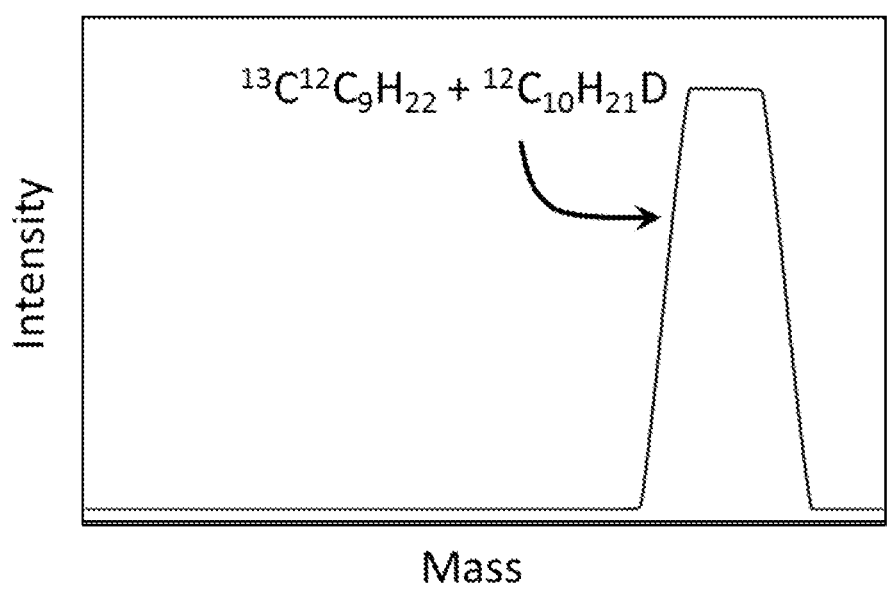
FIG. 14 is a graph showing a schematic mass spectrum corresponding to use of a second mass spectrometer according to an embodiment of the present invention.
Figure 15:
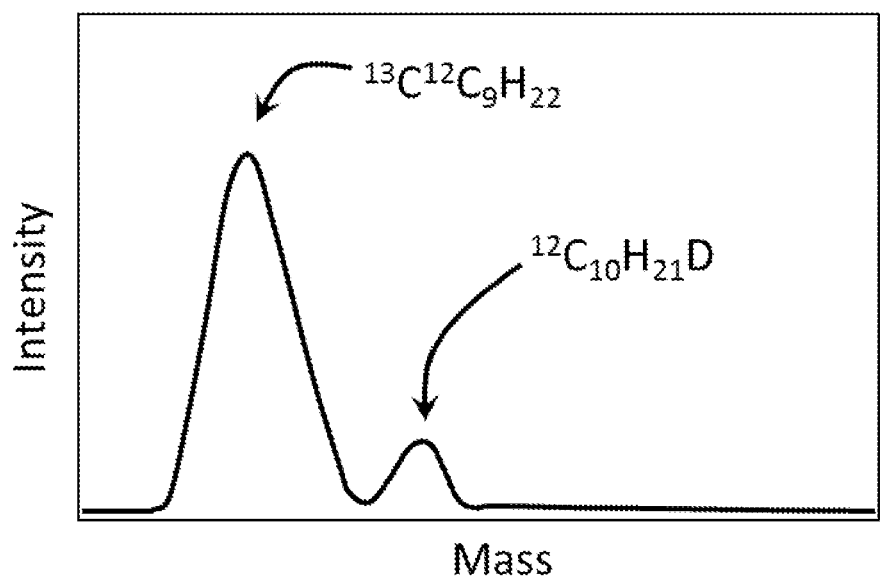
FIG. 15 is a graph showing a schematic mass spectrum of the same two ion beams illustrated in FIG. 14, but corresponding to use of a first mass spectrometer according to an embodiment of the present invention.

For example, FIG. 14 is a graph schematically showing a signal (or mass spectrum) corresponding to use of an embodiment of the second mass spectrometer to analyze $^{13}C$ substituted decane ($^{13}C^{12}C_9H_{22}$) and D substituted decane ($^{12}C_{10}H_{21}D$), which have the same cardinal mass. A signal such as the schematic signal shown in FIG. 14 can be obtained when two closely adjacent ion beams are permitted to simultaneously pass through an exit slit of the mass spectrometer and be collected together in the same detector. Because an embodiment of the second mass spectrometer is a multi-collector mass spectrometer, the sum of the intensities of these two species (the two ion beams) may be compared with intensities of one or more ion beams at some other cardinal mass measured concurrently (or simultaneously) on another detector. As can be seen in FIG. 14, the respective signals for $^{13}C^{12}C_9H_{22}$ and $^{12}C_{10}H_{21}D$ are not mass resolved from one another and, therefore, the contributions of $^{13}C^{12}C_9H_{22}$ and $^{12}C_{10}H_{21}D$ to the peak shown in FIG. 14 cannot be individually attributed to $^{13}C^{12}C_9H_{22}$ and $^{12}C_{10}H_{21}D$. FIG. 15, on the other hand, is a graph schematically showing a signal of the same two ion beams illustrated in FIG. 14, but corresponding to use of an embodiment of the first mass spectrometer to analyze $^{13}C$ substituted decane ($^{13}C^{12}C_9H_{22}$) and D substituted decane $^{12}C_{10}H_{21}D$). In this case, the two ion beams are resolved from one another and their relative intensities can be measured, as in FIGS. 7 and 8. For example, as can be seen in FIG. 15, the respective signals for $^{13}C^{12}C_9H_{22}$ and $^{12}C_{10}H_{21}D$ are mass resolved from one another and the relative proportions of $^{13}C^{12}C_9H_{22}$ and $^{12}C_{10}H_{21}D$ that contribute to the signal measured in the second mass spectrometer can be determined using the data collected using the first mass spectrometer. Thus, the second mass spectrometer can be used to obtain a signal that is free of contributions from contaminant isobars, but combines signals from isobaric isotopologues (e.g., $^{13}C^{12}C_9H_{22}$ and $_{12}C_{10}H_{21}D$), and the first mass spectrometer can be used to measure the abundance ratio of the isobaric isotopologues.

For example, a ratio [A]/[B] can be solved for based on the values of ratios [A+C]/[B] and [A]/[C] in a system in which [A] is the concentration of an isotopologue of interest, [B] is the concentration of a reference isotopologue (e.g., an unsubstituted version of a molecule or fragment of interest), and [C] is the concentration of an interfering species in which the signals measured for A and C using the second mass spectrometer are unresolved and the signals measured for A and C using the first mass spectrometer are mass resolved. If the ratios [A+C]/[B] and [A]/[C] are accurately determined, the system is fully defined, and the ratio [A]/[B] can be solved for explicitly. If, however, the ratios determined from first mass spectrometer and the second mass spectrometer include an associated error, the error will propagate to an error in the final calculated [A]/[B] ratio that can be solved for analytically for simple cases but is more easily addressed through Monte Carlo simulation.

Figure 16:
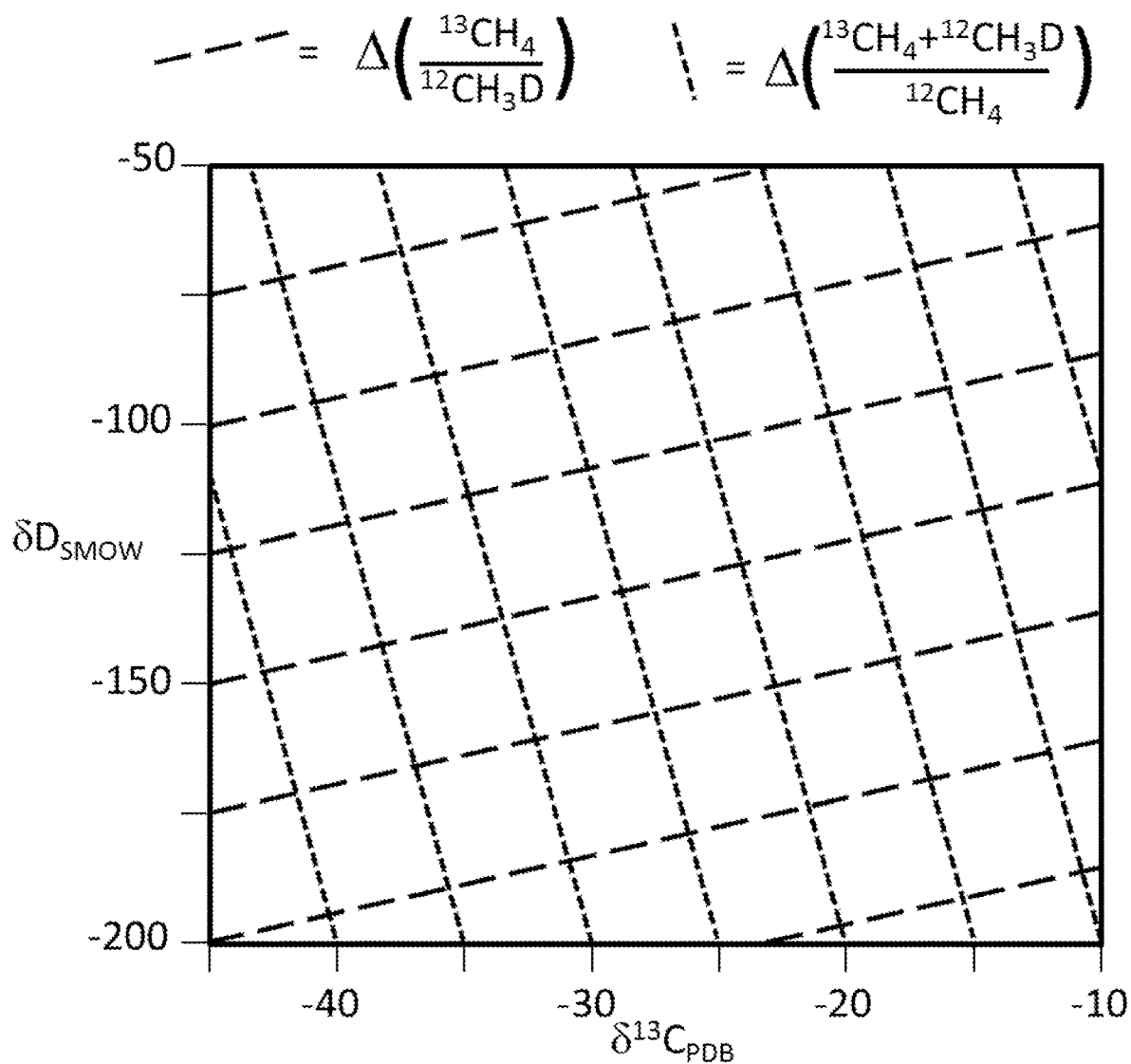
FIG. 16 is a graph showing a two-dimensional composition space for analyzing data acquired according to embodiments of the present invention.

FIGS. 16-22 are charts graphically illustrating embodiments of methods in which data from the first spectrometer and/or data from another analytical tool (e.g., the second mass spectrometer) is used to determine the isotopic composition of an analyte or sample. For example, FIG. 16 is a chart representing a two-dimensional composition space defined by $\delta D_{SMOW}$ and $\delta^{13}C_{PDB}$, which are measures of D and $^{13}C$ concentration, respectively, that are common in the art. $\delta D_{SMOW}$ is the deviation of the D/H ratio from that in Standard Mean Ocean Water, whereas $\delta^{13}C_{PDB}$ is the deviation of the 13C/12C ratio from that in Pee Dee Belemnite. Both variables are conventionally given in units of per mil. In FIG. 16, the Cartesian coordinates represent common variables for reporting concentrations of $^{13}C$ and D isotopologues, and the broken lines represent contours of constant measured ion intensity ratios, measured according to embodiments of the present invention (e.g., one set of contours represents a measurement of the ratio of two nearly isobaric species as measured with and embodiment of the first mass spectrometer and the second set of contours represents a measurement of the sum of those same two species divided by the abundance of some other, normalizing species having a different cardinal mass). Taken together, the intersecting contours of FIG. 16 define a second coordinate system that is a fully defined mathematical transformation of the first coordinate system. For example, in FIG. 16, the small broken lines at a generally vertical diagonal angle correspond to the constant $\Delta(^{13}CH_4+^{12}CH_3D/^{12}CH_3D)$, and the large broken lines at a generally horizontally diagonal angle correspond to the constant $\Delta(^{13}CH_4/^{12}CH_3D)$. The location of a sample in the space shown in FIG. 16 depends upon the concentrations of $^{13}CH_4$, $^{12}CH_3D$, and $^{12}CH_4$ in the sample.

Figure 17:
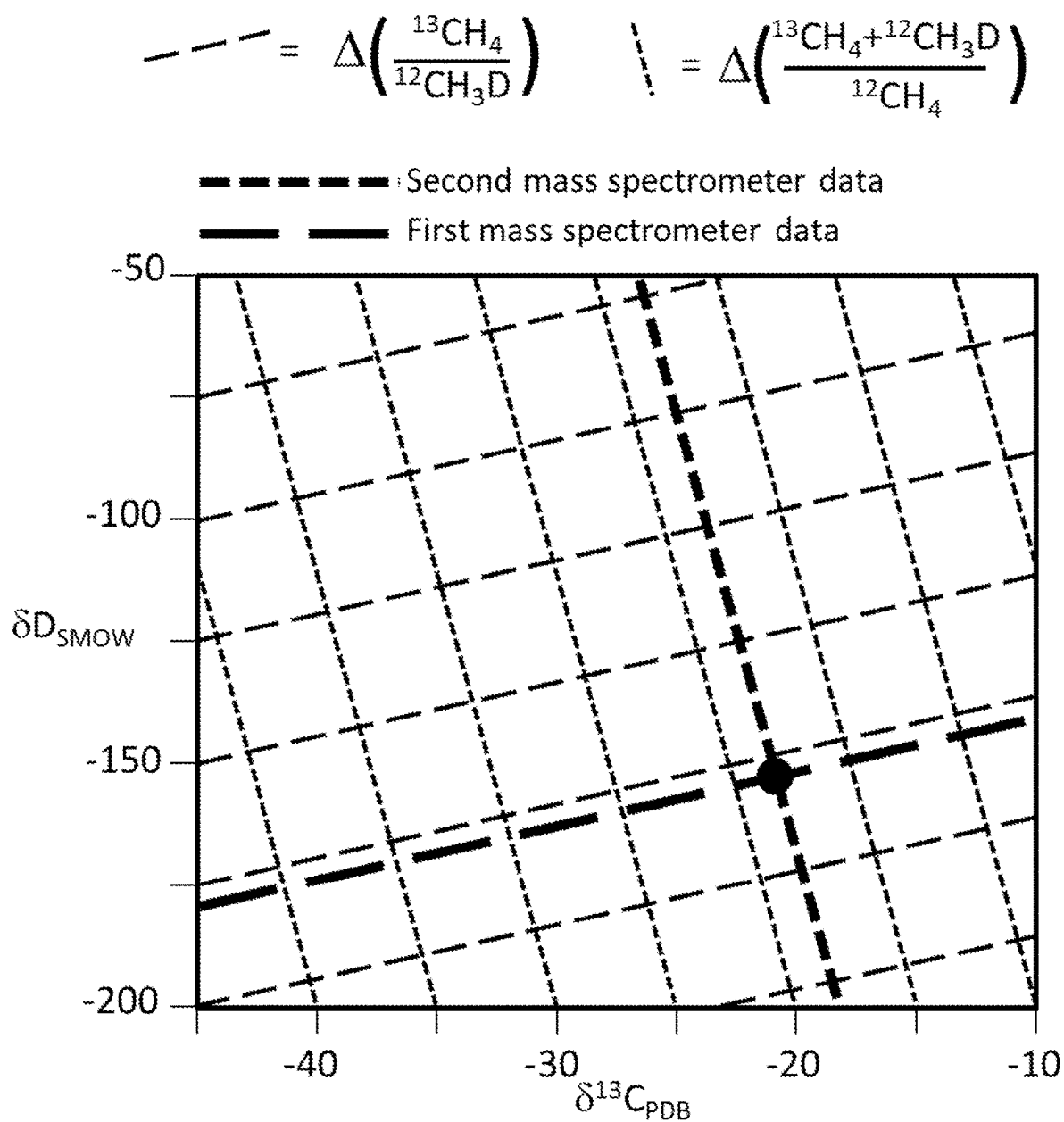
FIG. 17 is a graph illustrating an embodiment of a method in which a measurement of the composition of a sample using an embodiment of the first mass spectrometer and a measurement of the composition of the same sample using an embodiment of the second mass spectrometer can be combined to determine the concentrations of $^{13}C$ and D containing isotopologues in a sample.

Even though $^{13}CH_4$ and $^{12}CH_3D$ have the same cardinal mass of 17 amu, the respective signals corresponding $^{13}CH_4$ and $^{12}CH_3D$ can be mass resolved using an embodiment of the first mass spectrometer, and the ratio of $^{13}CH_4$ and $^{12}CH_3D$ can be determined. Additionally, even though $^{12}CH_4$ has a cardinal mass (16 amu) that is different from that of $^{13}CH_4$ and $^{12}CH_3D$ (17 amu), the signal corresponding to $^{12}CH_4$ and the signal corresponding to $^{13}CH_4$ and $^{12}CH_3D$ can be concurrently (or simultaneously) observed using an embodiment of the second mass spectrometer, and the ratio of $^{13}CH_4$ and $^{12}CH_3D$ to $^{12}CH_4$ can be determined. For example, FIG. 17 is a chart including the two-dimensional space shown in FIG. 16 as well as prophetic data from the first mass spectrometer and prophetic data from the second mass spectrometer. In FIG. 17, the large broken lines correspond to prophetic data from the first mass spectrometer, and the small broken lines correspond to prophetic data from the second mass spectrometer. As can be seen in FIG. 17, the two sets of data can be used (e.g., combined) to identify a point within the two-dimensional space illustrated in FIG. 17, from which the isotopic concentrations in the sample being studied can be determined. In FIG. 17, the compositions of the representative samples in the two-dimensional composition space are independently known based on measurements common to the art.

Figure 18:
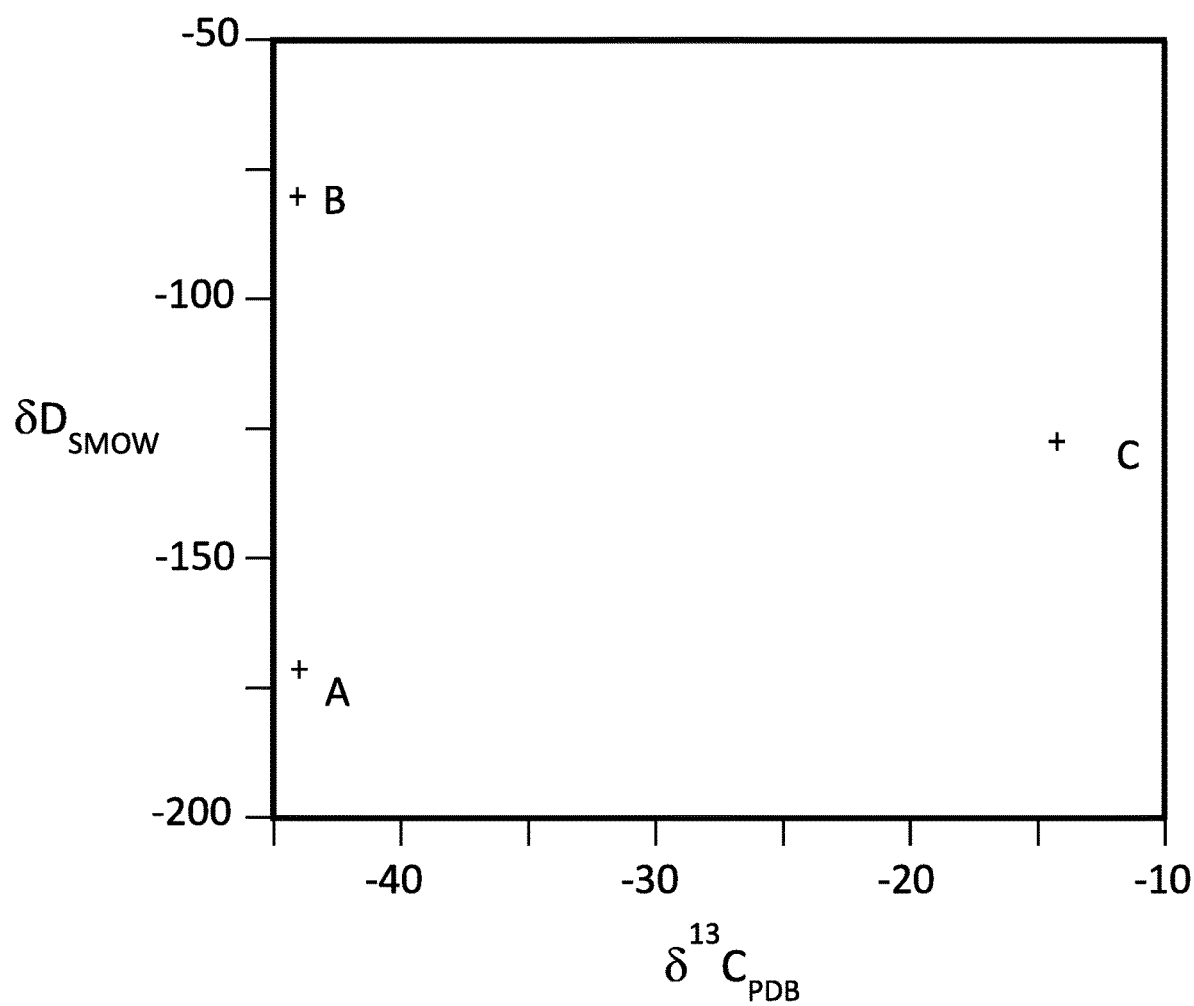
FIG. 18 is a graph illustrating the locations of three representative samples in the two-dimensional composition space illustrated in FIG. 16.
Figure 19:
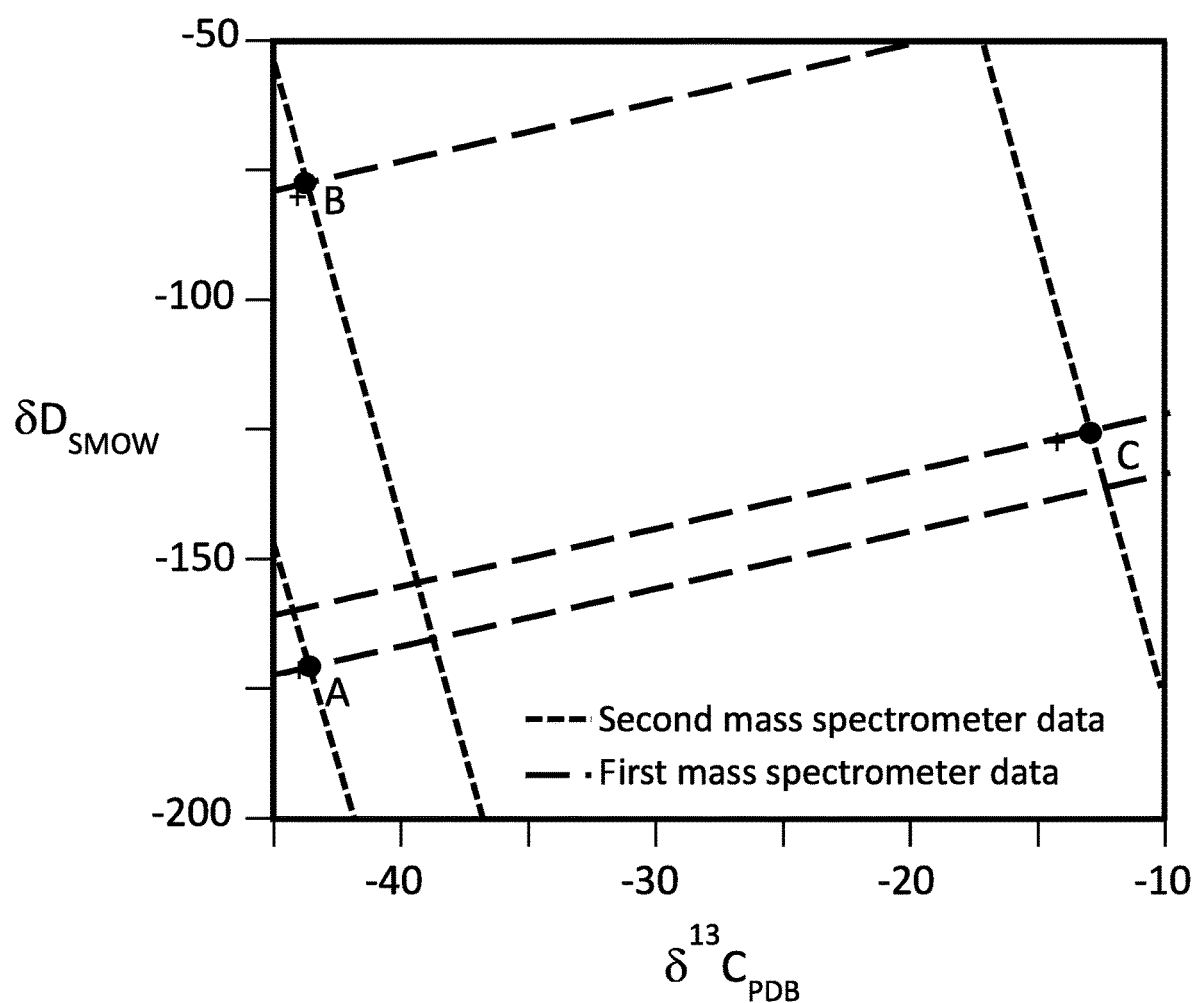
FIG. 19 is a graph showing the results of analyses of the three independently known gases from FIG. 18, using an embodiment of methods according to the present invention.

FIGS. 18 and 19 are charts illustrating application of the above-described methods to methane samples A, B, and C, of which A is a reference sample of known concentration and B and C are samples that were previously analyzed by methods common in the art to determine their isotopic abundances. The concentrations of $^{13}CH_4$, $^{12}CH_3D$, and $^{12}CH_4$ in the standards A, B, and C respectively correspond to the respective crosses shown in FIG. 18 (i.e., the cross for A corresponds to the known concentration of $^{13}CH_4$, $^{12}CH_3D$, and $^{12}CH_4$ in the standard A). FIG. 19 is a chart including the crosses corresponding to the isotopic compositions of samples A, B, and C, as well as data from an embodiment of the first mass spectrometer and data from an embodiment of the second mass spectrometer. In FIG. 19, the large broken lines correspond to data obtained from an embodiment of the first mass spectrometer, and the small broken lines correspond to data obtained from an embodiment of the second mass spectrometer. The data from the first and second mass spectrometers was used to identify the dots shown in FIG. 19, which correspond to the respective concentrations of $^{13}CH_4$, $^{12}CH_3D$, and $^{12}CH_4$ in the standards A, B, and C. The isotopic concentrations of the samples A, B, and C were determined with average errors (1 se) of $\delta^{13}C$: ±0.1%, and $\delta D$: ±0.9%; and average discrepancies of $\delta^{13}C$: 0.2%, and $\delta D$: 1.5%. In FIG. 19, the intersection of contour lines representing measurements made with embodiments of the first and second mass spectrometer lie within expected analytical uncertainties of the independently known compositions.

Figure 20:
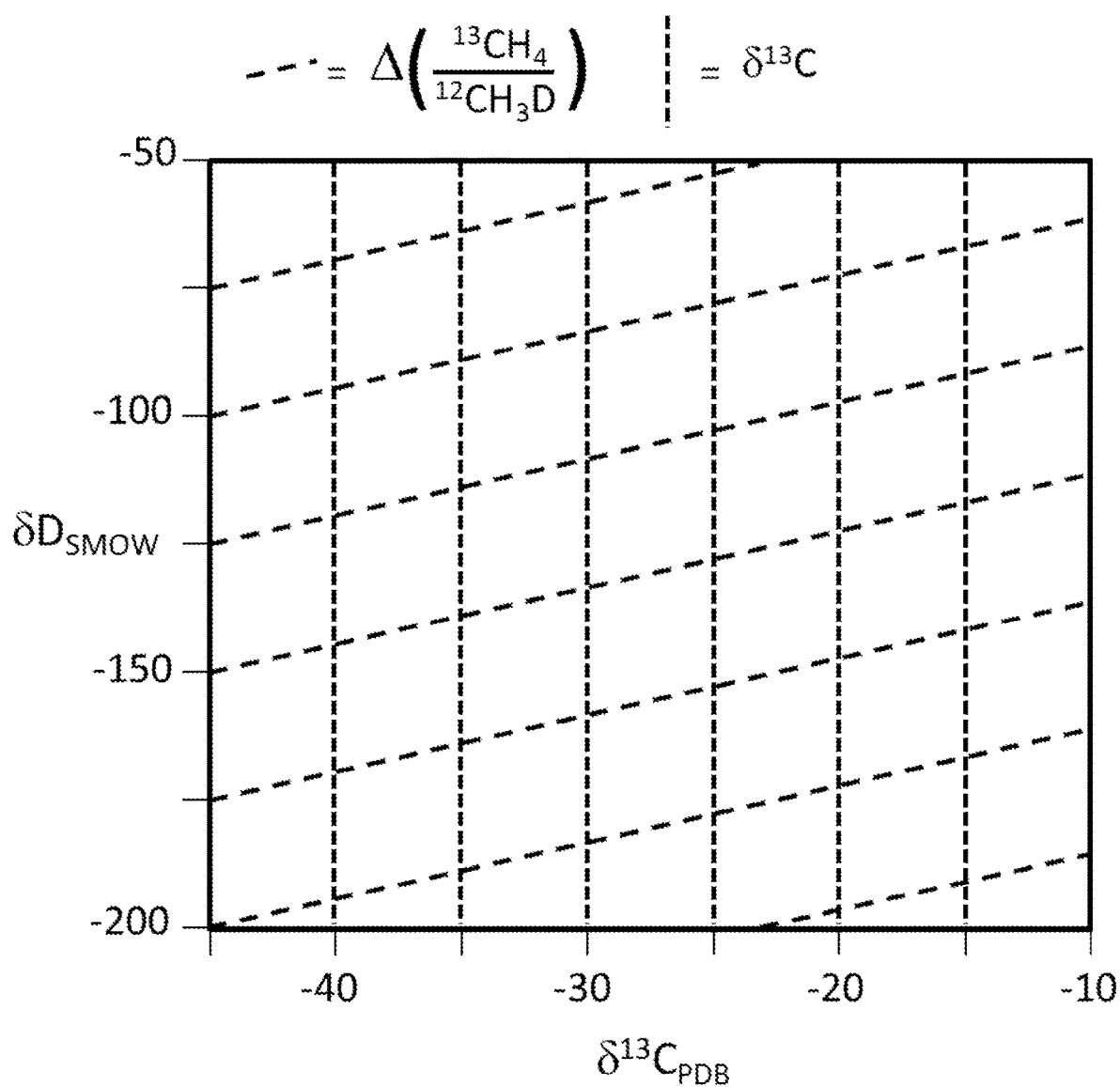
FIG. 20 is a graph showing another embodiment of a two-dimensional composition space for analyzing data acquired according to embodiments of the present invention.

Variations of the above-described methods can also be used to determine the isotopic composition of a sample, such as the methane samples described above. If there is one relevant constraint per each unknown, linear algebra can be used to construct a method for deconvolving mass spectra into component parts. For example, FIG. 20 is a chart showing another embodiment, as in FIG. 16, in which the Cartesian coordinates are common variables for reporting concentrations of $^{13}C$ and D isotopologues and the broken lines represent contours of constant values for independent constraints, one or both of which can be ion intensity ratios measured according to embodiments of the methods of the present invention. In FIG. 20, the two-dimensional composition space is defined by $\delta D_{SMOW}$ and $\delta^{13}C_{PDB}$, in which the vertical, small broken lines correspond to the constant $\delta^{13}C$, and the diagonal, large broken lines correspond to the constant $\Delta(^{13}CH_4/^{12}CH_3D)$. By varying the methods described above, data from an embodiment of the first mass spectrometer alone, or in combination with data from an embodiment of the second mass spectrometer or another device or method can be used to locate a point within the two-dimensional space shown in FIG. 20 that corresponds to the sample being measured, and from that point, the isotopic composition of the sample (or a portion thereof) can be determined.

Figure 21:
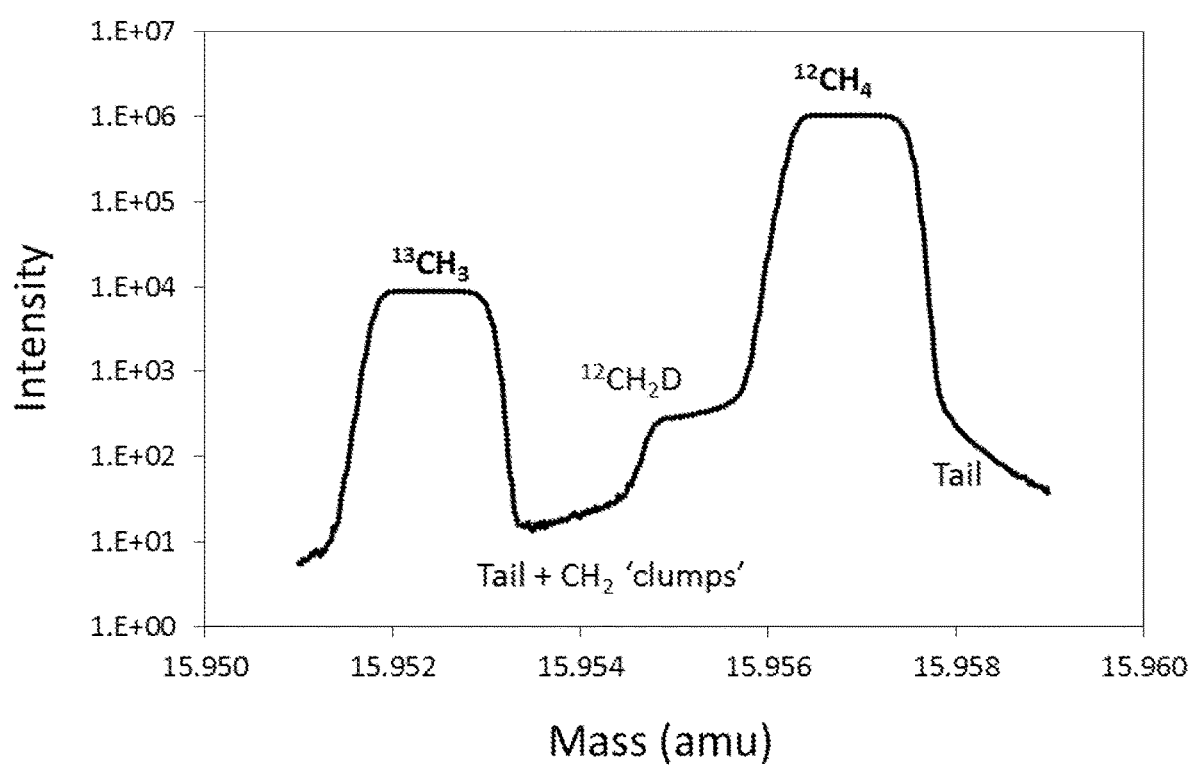
FIG. 21 is a graph showing a mass spectrum obtained using a first mass spectrometer according to an embodiment of the present invention.
Figure 22:
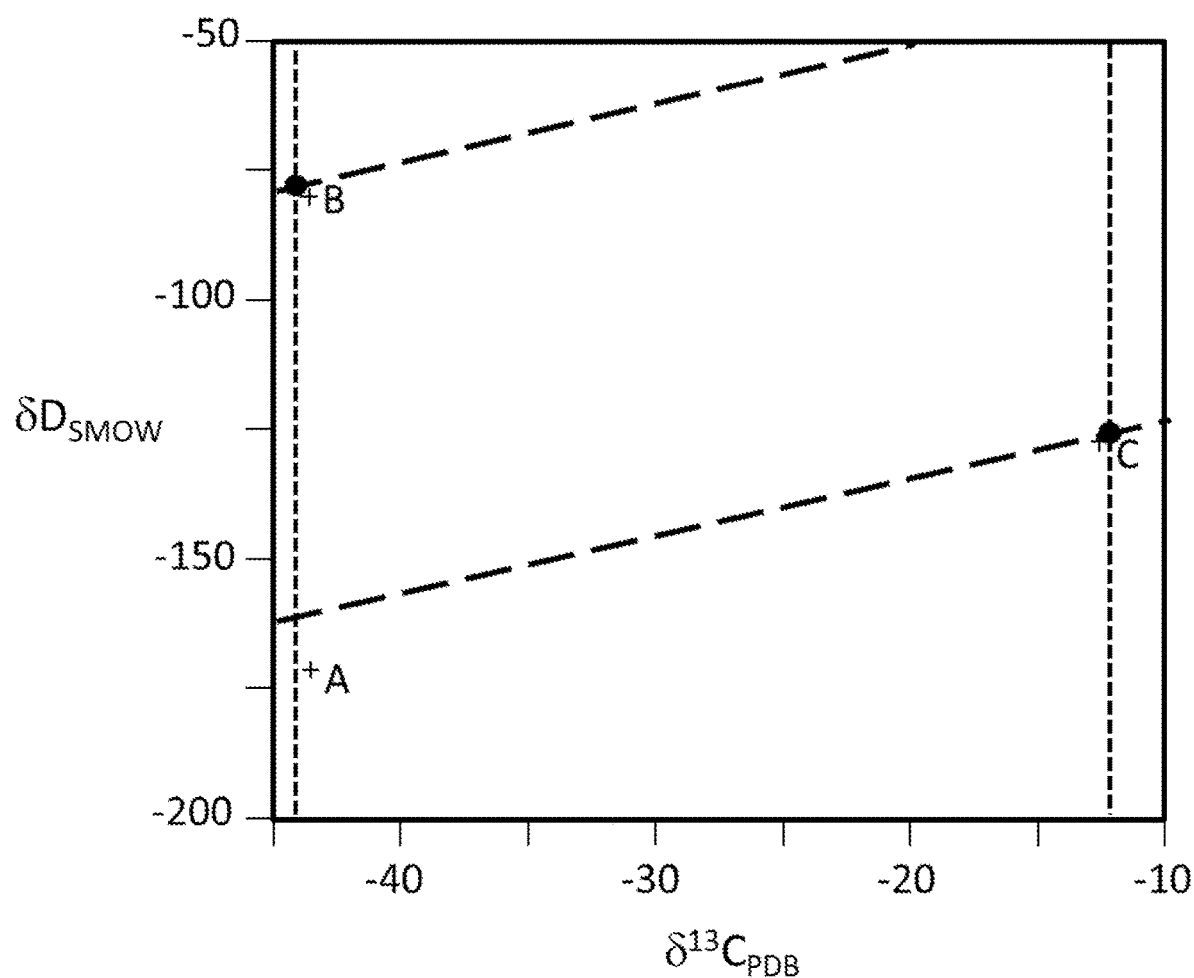
FIG. 22 is a graph showing the results of analyses of the three independently known gases from FIG. 18, using an embodiment of methods according to the present invention where both sets of contours are measured with the first mass spectrometer and the $^{13}C/^{12}C$ ratio is analyzed using features of the mass spectrum of FIG. 21.

In some embodiments, data from the first mass spectrometer may be used, on its own, to determine ratios of isotopes of one element (e.g., $^{13}C/^{12}C$, D/H, $^{15}N/^{14}N$, and the like) in a sample. For example, FIG. 21 shows data collected at one cardinal mass using an embodiment of the first mass spectrometer. In the mass spectrum shown in FIG. 21, when the probability ratio of forming the $CH_3$ and $CH_4$ ion species is equal in the sample and standard, the $^{13}C/^{12}C$ ratio of the analyte can be determined by comparing the $^{13}CH_3$ to the $^{12}CH_4$ ion beam and normalizing to a reference standard having a known $^{13}C/^{12}C$ ratio. Using that data, the ratio of $^{13}C$ to $^{12}C$ in the sample can be determined according to the equation $^{13}C/^{12}C=(^{13}CH_3/^{12}CH_4)\times(CH_3/CH_4)$. For example, FIG. 22 is a chart illustrating application of the above-described method to the methane samples A, B, and C, described above. FIG. 22 shows the results of analyses of the three independently known gases from FIG. 18, using an embodiment of methods according to the present invention where both sets of contours are measured with the first mass spectrometer and the $^{13}C/^{12}C$ ratio is analyzed using features of the mass spectrum of FIG. 21 Data from the first mass spectrometer was used to identify the dots shown in FIG. 22, which correspond to the respective concentrations of $^{13}CH_4$, $^{12}CH_3D$, and $^{12}CH_4$ in the standards B and C. The isotopic concentrations of the samples B and C were determined with average errors (1 se) of $\delta^{13}C$: ±1.1‰, and $\delta D$: ±0.9‰; and average discrepancies of $\delta^{13}C$: 0.9‰, and $\delta D$: 0.7‰. In FIG. 22, the intersection of contour lines representing measurements made with an embodiment of the first mass spectrometer lie within expected analytical uncertainties of the independently known compositions. Such methods are most readily applied to difference in the number of H among, fragments, adducts and hydrides.

Figure 23:
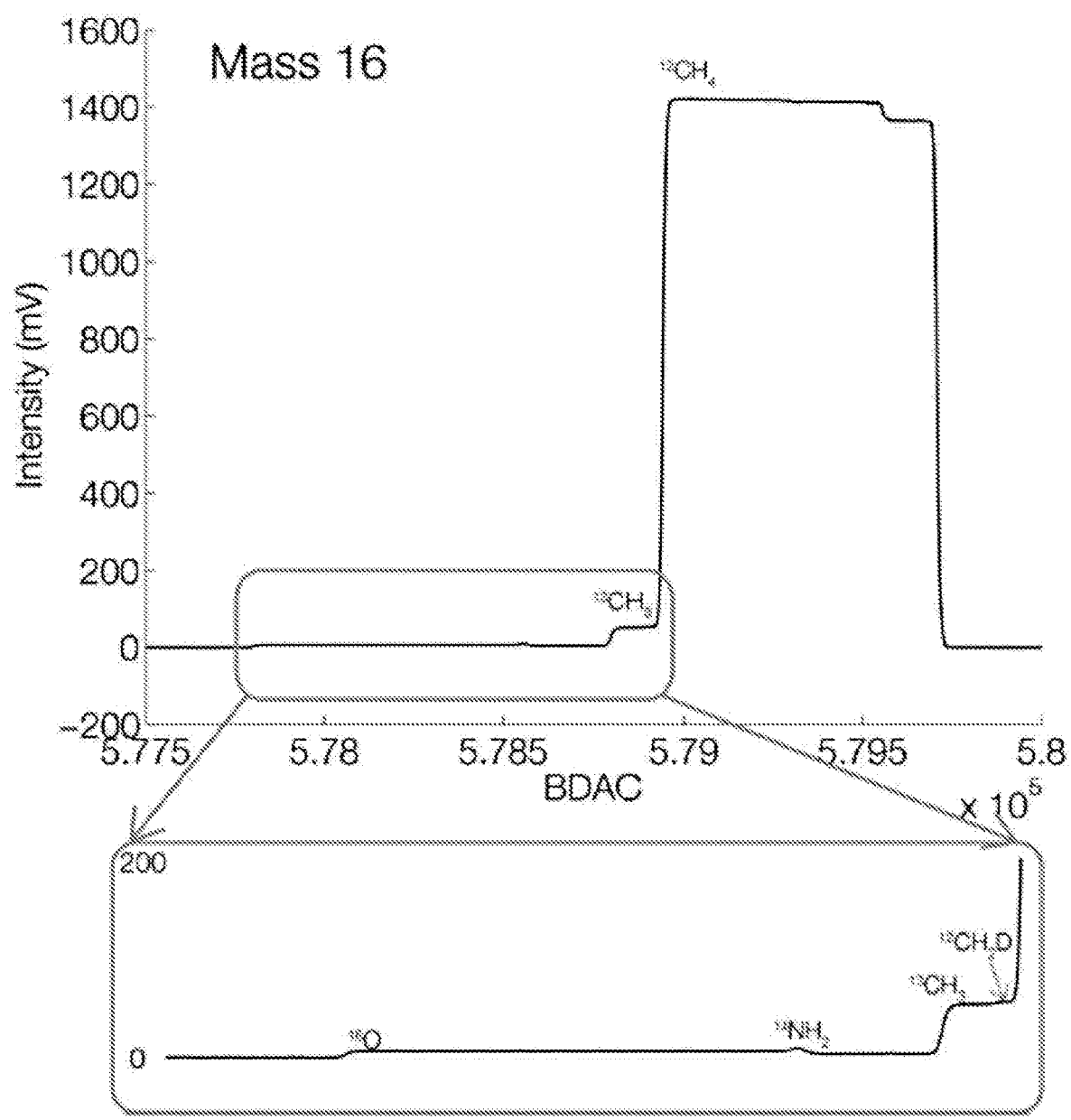
FIG. 23 is a graph, including a close-up view, showing a mass spectrum obtained using a second mass spectrometer according to an embodiment of the present invention.
Figure 24:
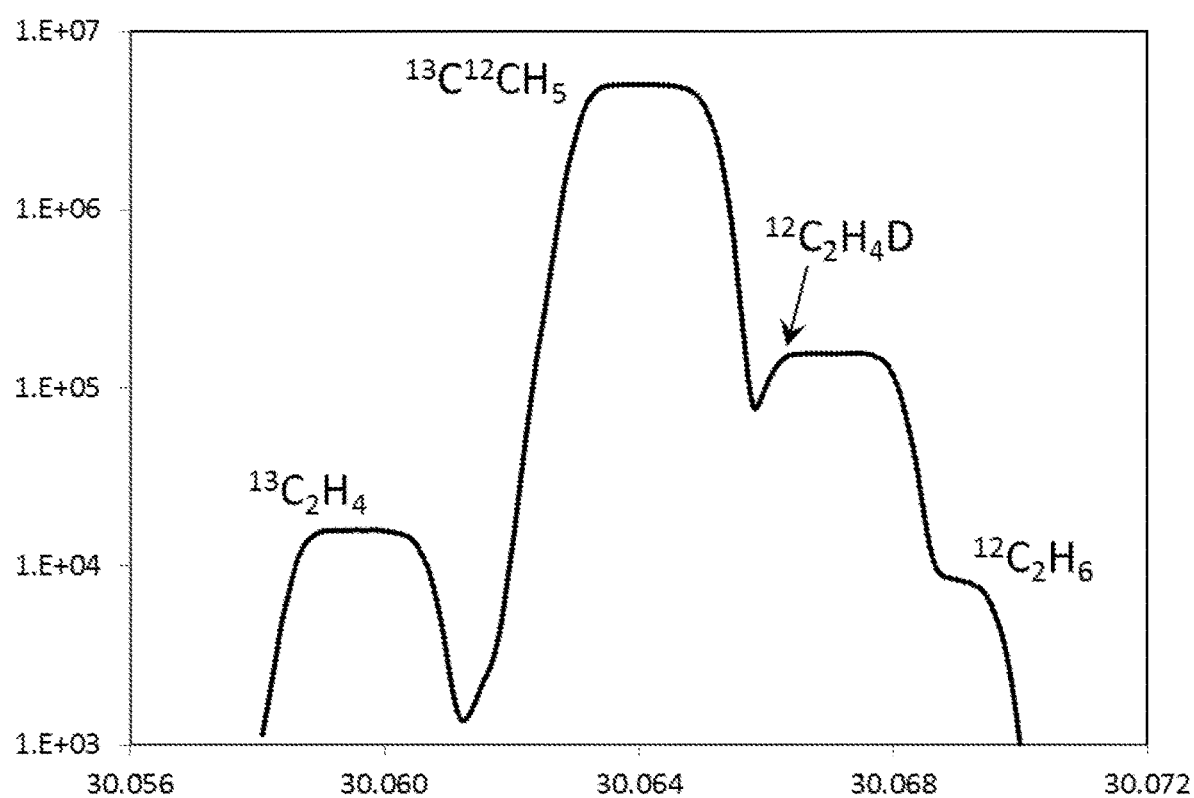
FIG. 24 is a graph showing a mass spectrum obtained using a first mass spectrometer according to an embodiment of the present invention.

Embodiments of the above-described methods can be used to identify isotopes at particular positions of an isotopologue. For example, embodiments of the above-described methods can be used to create a position-specific D/H "thermometer" for propane. FIG. 23 is a chart showing data acquired using an embodiment of the second mass spectrometer at a cardinal mass of 16 amu from a sample including propane. Analysis of the ratio $^{13}CH_3/^{12}CH_3$ using the second mass spectrometer can define the $\delta^{13}C$ of the terminal carbon site of propane. Comparison of this result with any measurement of the $\delta^{13}C$ of the full molecule allows for calculation of the difference in $\delta^{13}C$ between the terminal and central carbon site of propane. FIG. 23 illustrates the ability of an embodiment of the second mass spectrometer to resolve nearly isobaric species of fragment ions of organic molecules (e.g., separating $^{13}CH_3$ from $^{12}CH_4$ ions generated from propane). FIG. 24 is a chart showing data acquired using an embodiment of the first mass spectrometer at a cardinal mass of 30 amu from the sample including propane. FIG. 24 illustrates the ability of an embodiment of the first mass spectrometer to resolve $^{13}C$- and D-bearing isotopologues of the $C_2H_5$ fragment ion of propane. Accordingly, the first mass spectrometer can be used to measure the ion intensity ratios of $^{13}C$- and D-bearing isotopologues of fragment ions of propane. Data of the type shown in FIGS. 23 and 24 can be used to define the difference in D/H ratio between the terminal and central carbon sites of propane. In a population of propane molecules at thermodynamic equilibrium, the hydrogen atoms attached to the central carbon position should have a higher D/H ratio than those attached to the terminal carbon positions, and this difference should be larger at low temperature and smaller at high temperature. Thus, a measurement of the D/H ratios of fragments ions that differ in their proportions of hydrogen at the terminal and central sites should define the contrast between the two sites and thus the temperature of the population of propane molecules.

Figure 25:
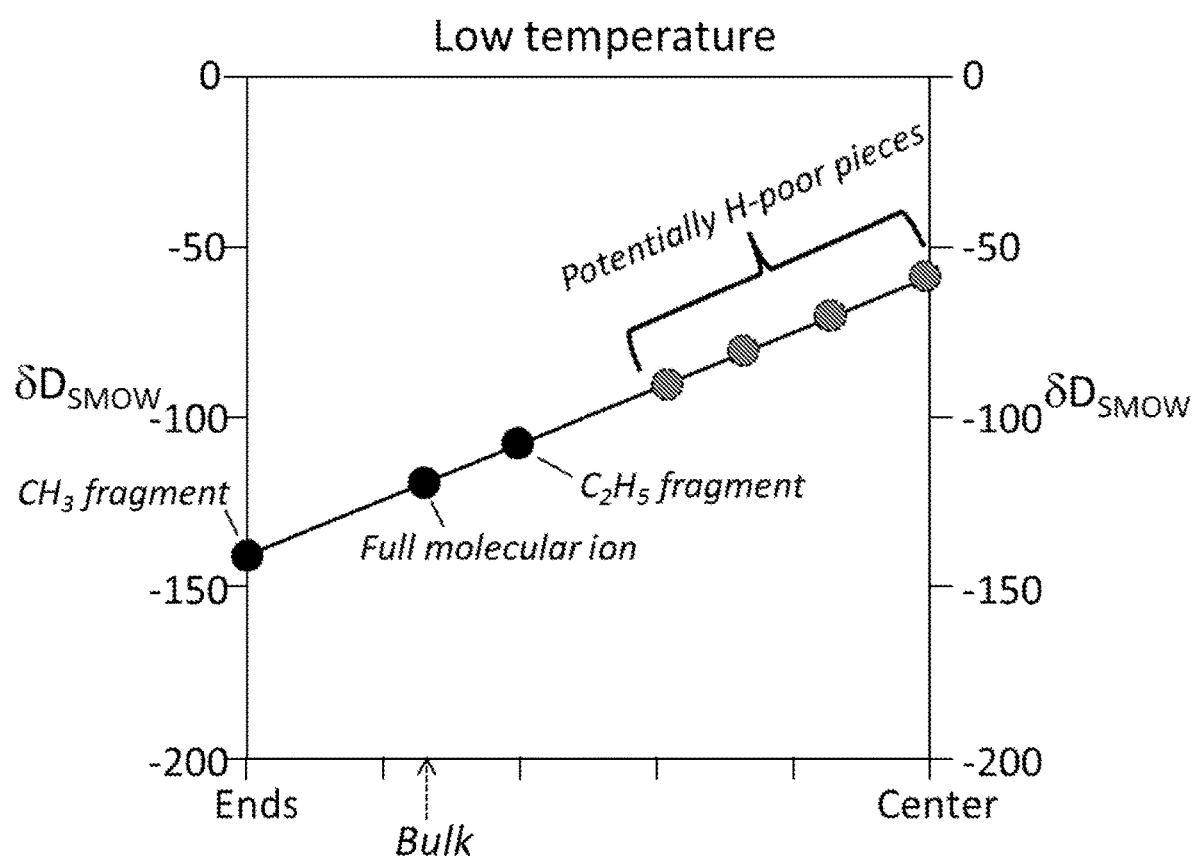
FIGS. 25 and 26 are graphs illustrating how measurements according to embodiments of the present invention can be combined to constrain the temperature of internal isotopic equilibration of propane.
Figure 26:
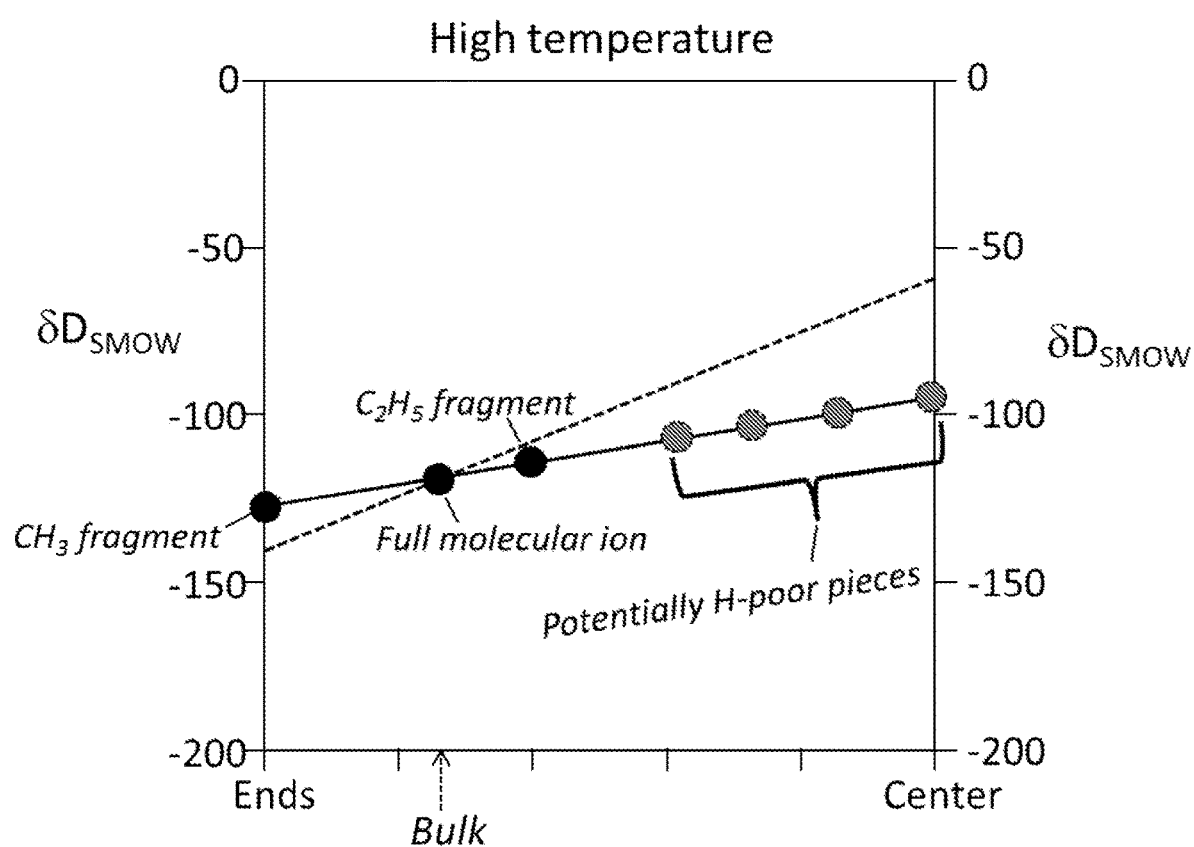

For example, FIGS. 25 and 26 illustrate how measurements according to embodiments of the present invention can be combined to constrain the temperature of internal isotopic equilibration of propane. For example, by measuring the D concentration of two or more fragment ions that differ in their proportions of hydrogen at the terminal and central carbon positions of the molecule, the difference in D/H ratio of those positions can be constrained. As noted above, this difference is large at low temperature and small at high temperature in a population of propane molecules that have achieved thermodynamic equilibrium. Similar methods can be used for multi-component, multi-method analysis of larger molecules.

According to embodiments of the present disclosure, the first mass spectrometer includes a single collector that detects signals at one (e.g., a single or sole) cardinal mass by rapidly scanning across all of the signals produced by the component isobars, before detecting signals at another cardinal mass. As described above, once the first mass spectrometer collects a suitable spectrum at one cardinal mass, the collector of the first mass spectrometer can switch (or jump) to another cardinal mass and the single collector can detect signals at the other (e.g., the other single or sole) cardinal mass by rapidly scanning across all of the signals produced by the component isobars at the other cardinal mass. While embodiments of the first mass spectrometer can determine relative proportions of species at each cardinal mass, and can do so at a very high resolution, embodiments of the first mass spectrometer do not achieve the same high precision as that of the second mass spectrometer (e.g., a multi-collector mass spectrometer). In some embodiments, the relative peak heights measured using the first mass spectrometer have errors of about 1% after standardization with a reference material, but the errors may be substantially smaller. The first mass spectrometer, however, is not required to have high precision, because the measurements from the first mass spectrometer can be used to ion-correct an already precise measurement of the total of all species at each cardinal mass detected using the second mass spectrometer.

Embodiments of the second mass spectrometer can measure ion intensity ratios at two cardinal masses (e.g., measuring on the flat tops of peaks, where all isobars are concurrently or simultaneously observed) with an external error of 0.1 per mil or better. Indeed, attaining such a level of precision is straightforward for an embodiment of the second mass spectrometer that is a multi-collector gas source mass spectrometer. Further, embodiments of the second mass spectrometer have mass resolving power sufficient to separate out most contaminants such that the signals observed using the second mass spectrometer can generally be assumed to include contributions isotopic isobars of the same molecule (or its fragments). For example, in some embodiments, the signal obtained by the second mass spectrometer may be substantially free of a contribution from contaminants (or the signal may include contributions only from isotopic isobars of the same molecule or its fragments). On the other hand, embodiments of the first mass spectrometer may be able to obtain intensity ratios for components at any one cardinal mass at a precision of about 1%. Using bracketing standardization and repeated analyses, substantially better levels of precision may be obtained using the first mass spectrometer. Based on the levels of precision described herein, the errors in measuring each isotopic species can be calculated using the ratios [A+C]/[B], [A]/[C] and [A]/[B] described herein. For example, the errors propagated through the calculations can be calculated using simulations such as Monte Carlo methods. It has been found that Monte Carlo simulations of propagated errors in the final measured isotope ratio of interest follow simple scaling relationships.

For highly abundant species (e.g., species that dominate the measured signal at one cardinal mass), the measured precision is generally equal to (relative error in the measurement from the first mass spectrometer)/(ratio of the abundant species to less abundant species at the cardinal mass). Such levels of precision provide good measurements for major species, even given conservative performance from the first mass spectrometer. For example, if a sample of decane is analyzed using the second mass spectrometer and found to have a ratio of the 143 amu cardinal mass to the 142 amu cardinal mass of $0.138\pm01.38\times10^{-5}‰$ (with 0.1‰ error), which is roughly equivalent to the ratio found in natural abundance decane, and the same sample is analyzed using the first mass spectrometer and found to have a $^{13}C^{12}C_9H_{22}/^{12}C_{10}H_{21}D$ abundance ratio of $42\pm0.42$ (with 1% error), which is also roughly equivalent to the ratio found in natural abundance decane, then the abundance of $^{13}C^{12}C^9H_{22}$ (i.e., the $\delta^{13}C$ of the C10 molecular ion) in the sample will be determined with an error of 0.24‰ (calculated using Monte Carlo techniques based on the levels of precision described herein). Thus, precision in $\delta^{13}C$ is degraded by about 0.1‰ from the error in the measurement of the 143/142 ratio using the second mass spectrometer. An error of about 0.2‰ is generally within the range of experimental error in conventional $\delta^{13}C$ measurements, and so an error of about 0.24‰ is acceptable.

For minor components (e.g., species that provide a relatively minor contribution to the measured signal at one cardinal mass), errors may be larger. In some embodiments, the errors for such species may converge on the relative error for the least abundant species for the spectrum obtained using the first mass spectrometer. For example, Monte Carlo modeling of the decane example described above may provide an error in $^{12}C_{10}H_{21}D$ abundance of 10‰, which is equal to the 1% error that may be obtained using the first mass spectrometer on its own. In some instances, such larger errors will hinder useful application of the subject matter disclosed herein to species that are minor components of a given cardinal mass and that have subtle isotopic variations.

Several methodological approaches, however, may reduce the effects associated with errors corresponding to minor species. For example, the fragmentation spectra of organic compounds are so complex that cardinal masses can be selected for their relatively smaller errors associated with the isotopic species of greatest interest (e.g., H-poor fragments can be selected when $\delta^{13}C$ is being determined). Additionally, results for fragments that differ in relative contributions of H and C can be compared to de-convolve relative contributions of D and $^{13}C$ at each cardinal mass. Furthermore, the use of sample-standard comparisons on pure analytes at matched pressures, which can be achieved for the first mass spectrometer by using a Thermo Delta V changeover (available from Thermo Fisher Scientific, Inc., Waltham, Mass.), will reduce errors to the ‰ range, even for minor species. Moreover, even if the measurements are constrained to the most abundant species at each cardinal mass, the subject matter disclosed herein will still provide a very large number of new measurements and extend the analysis capabilities of embodiments of the second mass spectrometer to analytes far into the high molecular mass range. While embodiments of the first mass spectrometer disclosed herein complement the capabilities of embodiments of the second mass spectrometer, the first mass spectrometer is also useful for isotopic analysis by itself, as described above. Nonetheless, in some embodiments, embodiments of the first mass spectrometer can be included in a system that also includes an embodiment of the second mass spectrometer to provide fully constrained ion correction of isotopic measurements of high molecular weight species.

One of the benefits of embodiments of the subject matter disclosed herein is the ability to analyze single, double and triple $^{13}$C substitutions in high-molecular-weight components of oils, including both proportions of these substitutions in the whole molecule and proportions of some or all of these substitutions in fragment ions. The information provided by such analysis can be used to construct a "map" of $^{13}$C substitutions in the carbon backbones of components of oils, and can be used to provide a high-dimensionality forensic fingerprint for discriminating sources of oil components, which can be used in deconvolving components of oils that have mixed sources or identifying oils and gases that include the same components. Depending upon the physical processes that control the carbon isotope anatomies of oil compounds, the subject matter disclosed herein may also be useful for identifying the biosynthetic pathways of parent compounds to oil components; identifying fingerprints of thermal maturation in the re-arrangement of carbon isotope anatomies; finding proxies quantifying and correcting for biodegradation; and finding molecular sites that are relatively susceptible to exchange or re-ordering and that take on a thermodynamically controlled position-specific and/or clumped isotope composition and thus can be used as quantitative thermometers.

The apparatus, systems and methods disclosed herein may be used to study relatively volatile components of oil that are structurally similar and only somewhat larger than the compounds described with respect to the second mass spectrometer in U.S. patent application Ser. No. 13/656,447, filed on Oct. 19, 2012, entitled HIGH-RESOLUTION MASS SPECTROMETER AND METHODS FOR DETERMINING THE ISOTOPIC ANATOMY OF ORGANIC AND VOLATILE MOLECULES. For example, the apparatus, systems and methods disclosed herein may be used to empirically characterize carbon isotope anatomies of natural and synthetic octanes (e.g., characterize how position-specific and clumped isotope compositions of octanes relate to their environment and mechanism of formation).

The apparatus, systems and methods disclosed herein can also be used to analyze isoprene ($CH_2$=CCH=$CH_2$), which has 2,304 stable isotopologues, 2,295 of which are multiply substituted (i.e., "clumped") isotopologues. As many as 33 of the isotopologues are analyzable at est. ±0.1-2 per mil (‰). Isoprene, which has a boiling point of 34° C. can be introduced into a mass spectrometer by being pushed through a bellows using helium as described above. Isoprene has 5 symmetrically non-equivalent isotopologues having one $^{13}$C; 4 symmetrically non-equivalent isotopologues having one D; 10 symmetrically non-equivalent isotopologues having two $^{13}$C's (4 constraints); 20 symmetrically non-equivalent isotopologues having one $^{13}$C and one D (5+ constraints); and about 18-33 of those isotopologues are analyzable with useful precision using the apparatus, methods and systems described herein. N-hexane has 33 readily analyzable singly and doubly-substituted targets: 3 symmetrically non-equivalent isotopologues having one $^{13}$C; 3 symmetrically non-equivalent isotopologues having one D; 9 symmetrically non-equivalent isotopologues having two $^{13}$C's; and 18 symmetrically non-equivalent isotopologues having one $^{13}$C and one D. In addition to compounds such as octane, isoprene and hexane, the apparatus, systems and methods disclosed herein can be used to study refractory components of oils (and other high molecular weight organics).

Embodiments of the apparatus, systems and methods disclosed herein can be used in the study of temperatures of formation and/or storage of natural gas and oil; climate records (e.g., temperatures) from, for example, cellulose, waxes, and/or lipids; metabolisms of extant and ancient life; sources of pollutants; sources of greenhouse gases; and origins of meteoritic organic matter; mechanisms of chemical isotope effects; and they can be used in criminal forensics; and biomedical research and diagnosis.

As discussed above, isotopologues are compounds, such as organic compounds, that include non-equivalent isotopic substitutions, such as the substitution of $^{13}$C for $^{12}$C, D for H, $^{15}$N for $^{14}$N, and the like, in symmetrically non-equivalent sites or combinations of sites. Isotopologues are generally distinct from one another in their chemical and physical properties. Thus, isotopologues generally can be fractionated from one another by chemical and physical processes, such as processes responsible for formation, consumption and/or transport of the isotopologues. The apparatus, systems and methods disclosed herein can be used in the study of any process, activity, interaction and/or condition that results in fractionation of isotopologues.

For example, the presently disclosed apparatus, systems and methods can be used to study catalyzed reactions that result in fractionation of isotopologues. Catalysts (e.g., enzymes) capable of catalyzing a given reaction, but having structures that are different from one another, may differ in the isotopic dependence of the reactions they catalyze as a result of structural differences between the catalysts, which may result in differences in the distribution of isotopes in the products of the catalyzed reactions (e.g., may result in distributions of isotopologues that are different from one another). For example, the apparatus, systems and methods disclosed herein can be used to study conversion (e.g., metabolic conversion) of coenzyme A and pyruvate, a metabolite derived from sugars and common to all known living organisms, to acetyl coenzyme A. The enzymes pyruvate decarboxylase and pyruvate dehydrogenase can catalyze the reaction of coenzyme A with pyruvate to form acetyl coenzyme A. Those reactions of coenzyme A with pyruvate proceed at a rate that depends upon the carbon isotope at the C2 and/or C3 position of pyruvate (shown below).

For example, the reaction of coenzyme A with pyruvate having $^{12}$C at the C2 and/or C3 position proceeds at a higher reaction rate than that of the reaction of coenzyme A with pyruvate having $^{13}$C at the C2 and/or C3 position. The reaction rate of coenzyme A with pyruvate, however, is relatively insensitive to the identity of the carbon isotope at the C1 position of pyruvate (shown below). Thus, any process (e.g., any metabolic process) that converts pyruvate and coenzyme A into acetyl coenzyme A and converts only a portion of the available pyruvate, will preferentially produce acetyl coenzyme A having $^{12}$C at the C2 (C=O) site (shown below), but leave the C1 site of acetyl coenzyme A (shown below) relatively unmodified.

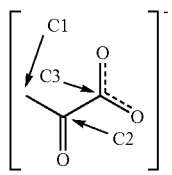

Pyruvate

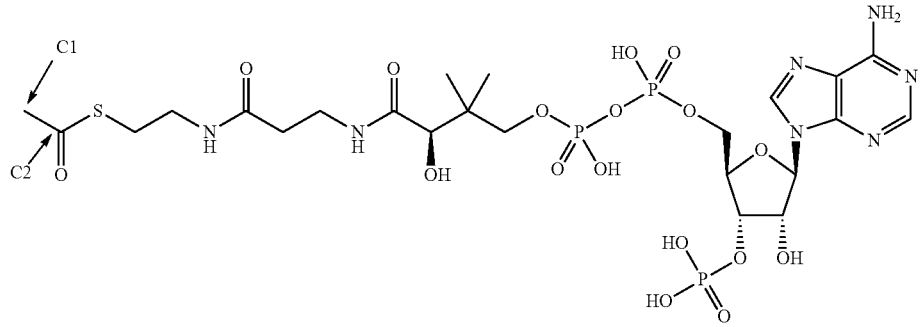

Acetyl coenzyme A

For example, a sample of acetyl coenzyme A prepared from only a portion of a sample of pyruvate will have a carbon isotopic distribution that is $^{12}C$ enriched, relative to the sample of pyruvate, at the C2 sites of acetyl coenzyme A, but will have a carbon isotopic distribution at the C1 site of the acetyl coenzyme A that is generally equivalent to the isotopic distribution of carbon in the sample of pyruvate. The foregoing isotope effect can be thought of as an isotopic "fingerprint" of the reaction that forms acetyl coenzyme A from coenzyme A and pyruvate. For example, a reaction catalyzed by pyruvate decarboxylase may result in fractionation (e.g., isotopic distribution) that is different from fractionation resulting from a reaction catalyzed by pyruvate dehydrogenase. Further, the above-described differences between the C1 and C2 carbon positions of fractionated isotopologues of acetyl coenzyme A also affect carbon isotope distributions in fatty acids produced from those fractionated isotopologues, in that the resultant fatty acids have systematic differences in $^{13}C$ abundances at the even and odd carbon positions (or sites). An example fatty acid is shown below having even sites (e.g., 2) and odd sites (e.g., 1). The above-described principles can also be used in the study of acetate and amino acids prepared from acetyl coenzyme A.

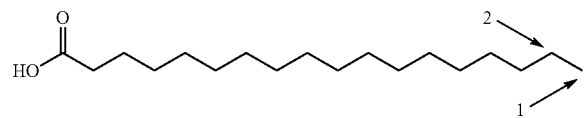 [SMILES: CCCCCCCCCCCCCCCCCC(=O)O]

Intramolecular isotopic differences also occur in other organic compounds produced by catalyzed reactions, such as amino acids, sugars, vanillin and the like. While the origins of the isotopic differences in these other compounds are less well understood than those in acetyl coenzyme A, these isotopic differences likely represent a fingerprint or isotopic signature of the biosynthetic pathways by which these molecules were formed and/or destroyed. Indeed, study of isotope effects on irreversible, abiological chemical reactions using highly isotopically enriched reagents or extreme extents of distillation (e.g., highly purified compounds) confirms that organic reactions generally lead to distinctive patterns of isotopic substitutions in partially consumed reactants and products (e.g., products produced by reactions in which only a portion of the reactants are consumed, and products that have been partially consumed), and that these patterns can be used to infer molecular and/or atomistic mechanisms of reaction. Based on the principles of chemical physics underlying fractionation of isotopologues, such as fractionation of isotopologues of acetyl coenzyme A, the apparatus, systems and methods disclosed herein can be used to study fractionated isotopologues of a wide variety of organic compounds.

Other apparatus, systems and methods distinguish among only a small number of isotopologues and are unable to provide a record of isotopic variations produced by organic synthesis and/or consumption reactions sufficient to make detailed inferences regarding the reaction histories (e.g., identifying specific enzymes involved) by which the isotopologues were made or partially consumed. In contrast, embodiments of the apparatus, systems and methods disclosed herein are capable of quantifying proportions of large numbers (e.g., tens to hundreds) of isotopologues of a wide variety of chemical compounds, at natural isotopic abundances and with precisions of est. $10^{-3}$ to $10^{-4}$, relative (e.g., standard errors on the order of 0.1 to 1 per mil in a measured abundance ratio of two isotopologues). The capabilities of embodiments of the apparatus, systems and methods disclosed herein have been demonstrated for n-alkanes, acetone, acetaldehyde and isoprene. Based on the principles of chemical physics underlying fractionation of isotopologues and the principles described herein, the apparatus, systems and methods herein can be used in the study of many common constituents of living organisms (e.g., sugars, amino acids and fatty acids) and a variety of compounds introduced into the body as drugs (e.g., valproic acid, which is described in more detail below). For example, relatively larger, heavier, and/or less volatile chemical compounds can be studied using the apparatus, systems and methods disclosed herein by way of derivatization chemistry, to improve volatility of the chemical compounds, and/or transfer of the chemical compounds through heated, purged non-reactive tubing, both of which are well understood methods used in the study of chemical compounds. Accordingly, the apparatus, systems and methods disclosed herein present the first practical approach for observing large numbers of isotopologues of diverse biomolecules (which are relatively larger and/or heavier chemical compounds). Applications of the apparatus, systems and methods disclosed herein are described in more detail below.

Environmental and Criminal Forensics

The apparatus, systems and methods disclosed herein can be used to make measurements of natural-abundance isotope distributions that are capable of distinguishing among sources of compounds of forensic interest, such as, for example, environmental pollutants, illicit drugs, mislabeled agricultural products (e.g., intentionally mislabeled agricultural products), and chemical and biological weapon agents. Such measurements take advantage of the fact that compounds made by different reaction pathways, under different environmental conditions (e.g., different temperatures), or in different geographical locations have different abundances of naturally occurring rare isotopes. These isotopic differences can be thought of as "fingerprints" that can be used to distinguish among chemical compounds from different sources.

While the above-described principles can be applied to forensic problems using apparatus, systems and methods other than those disclosed herein, those applications only constrain the bulk abundances of isotopes in a given sample, irrespective of the molecular sites of substitution of the isotopes or the proportion of molecules that contain multiple isotopic substitutions. For this reason, such measurements provide a small number of independent constraints on the origin of a compound, and thus provide insufficient constraints for fully analyzing forensic problems. For example, a measurement of the D/H isotope ratio of hair (principally keratin proteins of the hair) is a function of the D/H isotope ratio of dietary water, which varies with geography and thus can be a "fingerprint" of geographic provenance of the hair.

Local waters of many different geographic locations, however, share similar D/H isotope ratios, and different individuals consume water from regional water sources differently due to differences in diet. Thus, the above-described forensic measurements of hair are non-unique. In the example of hair keratin, an additional constraint based on a measurement of bulk isotopic abundance, such as the $^{13}C/^{12}C$ ratio of carbon, which differs between leafy plants and most grains and thus differs between individuals based on their dietary preferences, could be added. The addition of a second, independent compositional dimension (e.g., the above-described $^{13}C/^{12}C$ ratio of carbon) would improve the reliability of an isotopic forensic analysis based on such measurements. Given the diversity of dietary habits of individuals, however, even with the additional constraint, such measurements would still not provide sufficient constraint for a full forensic analysis.

Due to the very large number of isotopic variants of some chemical compounds, a full forensic analysis may be carried out using additional constraints. For example, each of the amino acids in each protein in hair keratin has a very large number of isotopic variants. Even alanine (chemical formula: $C_3H_7NO_2$), which is a relatively simple amino acid, has 18,432 isotopic variants. The abundance of each of these variants can be thought of as a potentially independent dimension of a composition space in which the locations of samples of forensic interest can be plotted. While measurements of bulk isotopic abundance of D/H and/or $^{13}C/^{12}C$ in a sample of alanine would be plotted in a 1 or 2 dimensional composition space (e.g., a line or plane), a full analysis of all isotopologues of alanine would provide an 18,432 dimensional volume, each dimension of which has the potential to record isotopic differences resulting from differences in geographic origin, dietary sources or other factors relating to the alanine being examined. While creating and using such complex isotopic data presents some challenges, experience gained from working with similarly complex genomic data can be drawn upon to guide analysis of the isotopic data to greatly improve the ability to distinguish among compounds having different origins.

The apparatus, systems and methods disclosed herein are demonstrably capable of measuring dozens to hundreds of isotopologues of many chemical compounds, and in principle could be extended to many more isotopologues. The apparatus, systems and methods disclosed herein should be capable of providing forensic distinctions among compounds of different origin in composition space volumes having dozens to hundreds of independent dimensions.

Oil and Gas Exploration

It is useful in petroleum exploration to identify or define the sources of petroleum products (e.g., the collection of organic compounds from which the petroleum products are derived), the nature and extent of progress of reactions by which they form, and the conditions (e.g., temperatures, pressures, etc.) of their formation and storage. The apparatus, systems and methods disclosed herein can be used to make measurements that can be applied to the field of oil and gas exploration in a variety of ways. A measurement that defines the temperature of formation and/or storage of iso-octane ($C_8H_{18}$; an important component of gasoline and one of the most valuable distillates of natural petroleum) is one example of such a measurement.

Hydrogen occupies a variety of symmetrically non-equivalent sites in iso-octane. Among the differences in the hydrogen atoms of iso-octane are the number of hydrogen atoms bound to each carbon: 15 are present as groups of 3, bound to a single carbon (the hydrogen atoms of the methyl groups); 2 are present together, bound to a single carbon (the hydrogen atoms of the "$CH_2$" group); and 1 is bound alone to a single carbon (the hydrogen atom of the "CH" group). A population (or sample) of iso-octane molecules that achieves intra-molecular and inter-molecular isotopic equilibrium will distribute D unevenly among the above-described hydrogen atom sites, concentrating D into the "CH" (or "CD") and "$CH_2$" (or "CHD" or "$CD_2$") groups, and H into the methyl groups. The strength and temperature dependence of the foregoing effect is known from experiment and theory for some fatty acids and n-alkanes, indicating that the difference in D/H ratio between the "$CH_2$" and methyl groups should be a factor of ~1.09 at subterranean, near-earth-surface temperatures (e.g., ~50° C.), and decrease monotonically with increasing temperature to a factor of ~1.03 at the highest temperatures of petroleum genesis (e.g., ~200° C.).

The apparatus, systems and methods disclosed herein are capable of measuring D/H ratios of fragment ions of organic compounds with a precision of ~0.001, relative (e.g., a standard error of 1 per mil). Different fragment ions contain different proportions of hydrogen atoms from different molecular sites and, thus, by comparison of the D/H ratios of two or more fragment ions, the temperature of equilibration of iso-octane can be defined with a precision on the order of a few degrees. It has not yet been established whether natural iso-octane forms in isotopic equilibrium with respect to the foregoing property, or whether the temperatures it records are those of its formation or storage (or perhaps both, depending on circumstances). Nevertheless, the above-described analysis of iso-octane is just one representative example of a large number of possible analyses related to the apparatus, systems and methods disclosed herein.

Personalized Medicine

The apparatus, systems and methods disclosed herein can be used in monitoring and analysis of drug budgets. Many drugs introduced into the human body are destroyed and excreted by diverse mechanisms. For example, valproic acid ($C_8H_{16}O_2$), which is often used as an anti-seizure medication (e.g., for treatment of epilepsy) and, less often, as a mood stabilizer for bipolar disorder, is destroyed by a chemical reaction in a patient's mitochondria, by reaction with one or more of six different enzymes in the patient's liver, or it is directly excreted from the patient's body. As such, the body of a patient taking this drug can be thought of as a living chemical rector having a quasi-steady-state budget of valproic acid that is characterized by one source term (the ingested drug) and eight "sink" terms (the various mitochondrial and enzymatic destruction pathways and excretion).

Many drugs have associated side effects that result, directly or indirectly, from the metabolic destruction of the drug rather than through action of the intact drug. For example, valproic acid interferes with liver function, reduces the ability of the liver to metabolize dietary fatty acids, possibly leading to liver damage or death, pancreatitis and/or extreme weight gain. These side effects likely result from the chemistry of valproic acid destruction in the liver. The severity of side effects on any given patient are difficult to predict, and generally can be monitored only by observing negative symptoms in the patient.

It may be possible to characterize an individual patient's tolerance for a drug, such as valproic acid, prior to the emergence of negative side effects in the patient by analyzing the state of the "budget" for that drug in the patient (e.g., by analyzing the balance of sink processes that the patient's body uses to destroy or excrete the drug). Because enzymes of a given type may vary in their structure and reactivity, a full characterization of an individual patient's budget for a drug, including isotopic "fingerprints" associated with each sink term, may detect and characterize any pathological abnormalities in the efficiencies of one or more of the enzymes that a patient's body uses to metabolize the drug.

Previous studies using isotopically labeled drug compounds, such as valproic acid, have identified possible sink processes for the destruction of the drug and indicated their typical or average relative rates. More information is needed, however, to fully characterize the state of an individual patient's chemical budget of a drug at any given time. The measurement of a large number of isotopologues of a drug (for example, measurement of several dozen isotopologues may be sufficient) may provide an isotopic fingerprint useful for characterizing the state of a patient's chemical budget for that drug, provided that the isotopic composition of the drug is known prior to being administered (e.g., by measuring the isotopic composition of the drug prior to ingestion by the patient). Each of the sink processes for the destruction of the drug may have associated with it a set of distinctive isotopic fractionations that result from the isotope dependence of rates of enzymatic reaction. While some of these isotope effects are unknown at present, they may be determined through experimental study of in vitro reaction of the drug (e.g., valproic acid) with the relevant isolated enzymes. If each sink process is unique with respect to an isotopic fingerprint (e.g., the dependence of reaction rate on isotopic substitutions in valproic acid), then a measurement that constrains proportions of 9 or more isotopologues in both the consumed drug (e.g., the medicinal dose taken by the patient) and the quasi-steady-state blood level of the patient would be sufficient to characterize the proportions of all 8 major sink processes and, thus, the balance of that patient's budget for that drug. Measurement of more than 9 isotopologues would over-constrain the budget (e.g., provide surplus information) and mitigate against any loss of information that results from too close of a similarity in some isotope effects associated with multiple sink processes (e.g., "degeneracy" in the family of constraints).

Similar principles could be used to constrain (or analyze) the budgets of a wide range of drug compounds in individuals (e.g., people or animals). The foregoing principles can be put into practice for any one case by addressing the following technical matters: (1) obtaining concentration analyzable quantities (typically micrograms to milligrams) of the compound of interest from blood or tissue samples; (2) chemical preparation of the analyte to increase volatility (e.g., derivatization of valproic acid to methylate or perfluorinate the hydroxyl site of valproic acid), if desired; and/or (3) experimental characterization of the end-member reactions involved in that drug's biochemistry (e.g., determination of the set of fractionations of proportions of all measured isotopologues associated with reaction with each of the "sink" enzymes).

The apparatus, systems and methods disclosed herein can be used in the diagnosis of metabolic disease. For example, the principles described above could be extended to biochemical compounds other than drugs, including a large number of sugars, amino acids, fatty acids and other metabolites. Budgets of these biochemical compounds in individuals (e.g., people or animals) may be identified through characterization of a number isotopic constraints (e.g., measurements of a number of isotopologues) equal to or greater than the number of major source and sink processes in the budget. Similarly to the above-described drug budgets, the possibility of redundancy or close similarity in some isotope effects among two or more source and/or sink terms may make it advantageous to substantially (or significantly) over constrain the budget (e.g., by measuring ~2 dozen isotopologues of a compound that has a budget characterized by 5-10 source and/or sink terms).

The above-described methods may be particularly useful for the diagnosis and detailed characterization of metabolic diseases, such as those involving carbohydrate metabolism (e.g., diabetes) or amino acid metabolism (e.g., phenylketonuria). For example, type 2 diabetes is characterized by a failure to metabolize glucose (or a lessened ability to metabolize glucose), despite the presence of an adequate abundance of insulin in the body. This disorder is believed to involve a defect (or defects) in an insulin receptor, but the exact mechanism of the disorder is unclear. A measurement that characterizes the isotopic "budget" of blood glucose could provide insight into the balance of sink reactions (or terms) for blood glucose (e.g., in response to catabolic and/or anabolic hormones) and the molecular or atomistic mechanisms of those reactions (e.g., by characterizing the pattern of isotope effects associated with the consumption or destruction of blood glucose). Such measurements may reveal the existence of unrecognized sub-types of type 2 diabetes, and provide for monitoring and characterizing the disease in individuals.

Environmental Chemistry

The apparatus, systems and methods disclosed herein can also be used in the study of photochemical fractionations that occur in the Earth's atmosphere. Indeed, intra-molecular isotopic distributions have many uses, such as, for example, the study of atomistic reaction mechanisms (e.g., the study of the Diels-Alder reaction of isoprene and maleic anhydride to form cyclohexene products), diffusion, gravitational settling, mixing, high-dimensionality "fingerprinting," deconvolving complex budgets, and chemical or pyrolitic degradation (e.g., ozonolysis, oxidation, and/or decarboxylation; such as the degradation of palm itoleic acid).

The above-described applications of the apparatus, systems and methods disclosed herein are technically straightforward when applied to compounds that are intrinsically volatile and are readily available at high concentrations (e.g., have high abundances in the blood stream, such as glucose or urea).

Figure 27:
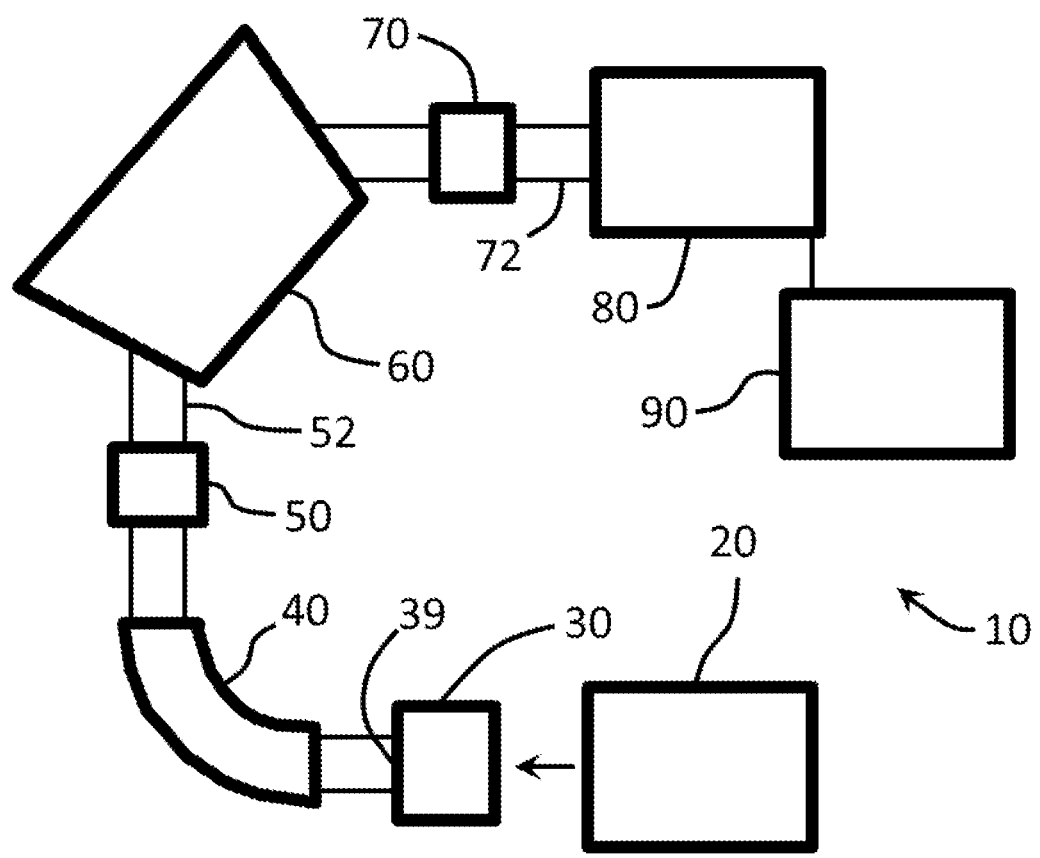
FIG. 27 is a schematic top view of a mass spectrometer according to another embodiment of the invention.

Embodiments of the second mass spectrometer will now be described in more detail. The aspects, features and methods described with respect to the second mass spectrometer may also be available for embodiments of the first mass spectrometer described herein. According to an embodiment of the invention, the second mass spectrometer has the ionization capabilities of a gas source isotope ratio mass spectrometer and the mass resolution, sensitivity and versatility of analyzers and detector arrays of ion microprobe and inductively coupled plasma mass spectrometers. An embodiment of the second mass spectrometer is shown in FIG. 27. The spectrometer shown in FIG. 27 may be a normal geometry, double-focusing sector mass spectrometer. A sector mass spectrometer of this kind is suitable as an embodiment of the "second mass spectrometer," because such instruments are capable of multi-collection, permitting concurrent (or simultaneous) analysis of ion beam intensities at two or more cardinal masses. In the embodiment shown in FIG. 27, the second mass spectrometer 10 includes a second ion travel path along a second entrance slit 39, a second energy filter 40 (e.g., an electrostatic analyzer or "ESA") and a second momentum filter 60 (e.g., a magnetic sector) configured to provide ions (e.g., sixth molecular analyte ions) to a detector array 80. The second mass spectrometer can be configured to provide a second mass resolution (which is described in more detail below) of 20,000 or greater at the detector array by sequentially arranging the second entrance slit, the second energy filter and the second momentum filter, and by appropriately selecting a second width of the second entrance slit, a third radius of curvature of the second energy filter and a fourth radius of curvature of the second momentum filter.

The second mass resolution achieved by a second mass spectrometer according to embodiments of the invention (e.g., a magnetic sector mass spectrometer) is generally proportional to the separation distance between two ion beams that the second mass spectrometer can achieve for ion beams that include respective ions having masses that are different from one another. The separation distance between the ion beams is proportional to the fourth radius of curvature of the second momentum filter (i.e., magnet) along the second ion travel path, and inversely proportional to the width of each ion beam, which is proportional to the width of the second entrance slit. Additionally, the highest mass resolutions can be achieved by momentum filtering (e.g., magnetic sector mass spectrometry) if the ions being filtered by momentum have substantially uniform kinetic energy. Thus, according to embodiments of the invention, the ions are filtered by energy (e.g., by the energy filter) prior to being filtered by momentum (e.g., by the momentum filter). Accordingly, the second energy filter has dimensions that are consistent with the creation of a double-focusing condition at the ion detector, given the accelerating potential of the ions as they exit the second ion source and the radius of the second momentum filter. For example, second mass resolutions in the range of about 2,000 to about 20,000 can be achieved if the second entrance slit has a second width of about 250 µm to about 5 µm, respectively, the ions are accelerated to 5 keV after exiting the second ion source, the third radius of curvature of the energy filter along the second ion travel path is about 20 cm to about 25 cm, the ions are further accelerated by an additional 5 keV after the second energy filter, and the fourth radius of curvature of the second momentum filter (e.g., magnetic sector) is about 20 cm to about 25 cm. In one embodiment, the second width of the second entrance slit is about 5 µm, the third radius of curvature of the second energy filter is about 22 cm, and the fourth radius of curvature of the second momentum filter is about 23 cm.

Embodiments of the second mass spectrometer also include a source of an analyte and a source of a reference material. For example, as shown in FIG. 27, the second mass spectrometer 10 can also include a sample introduction apparatus 20 (e.g., a second sample introduction apparatus), which is configured to provide an analyte gas (or other gases) to a second ion source 30. The second ion source is configured to convert the analyte gas (or other gases, such as various reference materials described below) to ions (e.g., fourth molecular analyte ions). The ion source produces the ions as a first output (e.g., the fourth molecular analyte ions). As the ions exit the ion source, they encounter the second entrance slit 39, which can be included as a component of the second ion source or can be connected to the second ion source. The second entrance slit is configured to guide the first output of molecular analyte ions (the fourth molecular analyte ions) along the second ion travel path.

The second energy filter 40 (e.g., the ESA) is positioned along the second ion travel path downstream from the second entrance slit 39 and is configured to receive the first output of molecular analyte ions (the fourth molecular analyte ions), which have energy levels. The second energy filter has a third radius of curvature along the second ion travel path and is configured to filter out fifth molecular analyte ions from the fourth molecular analyte ions according to their energy levels and produce a second output of molecular analyte ions. The second energy filter can be any suitable device that can filter ions according to their energy levels, such as an ESA.

A first ion focusing element 50 can be included along the second ion travel path between the second energy filter 40 and the second momentum filter 60. The first ion focusing element is configured to focus the second output of molecular analyte ions (the fifth molecular analyte ions) along the second ion travel path to the second momentum filter. The first focusing element can be any suitable device capable of focusing the second output of molecular analyte ions (the fifth molecular analyte ions), such as an electrostatic or magnetic lens (e.g., a quadrupole or higher format lens).

The second momentum filter 60 is positioned along the second ion travel path downstream from the second ion source 30, the second entrance slit 39, the second energy filter 40 and the first ion focusing element 50, and is configured to receive the second output of molecular analyte ions (the fifth molecular analyte ions). The second momentum filter has a fourth radius of curvature along the second ion travel path and is configured to filter out sixth molecular analyte ions from the fifth molecular analyte ions according to their momenta and produce a third output of molecular analyte ions. The second momentum filter can be any suitable device that can filter ions according to their momenta, such as a magnetic sector.

A second ion focusing element 70 can be included along the second ion travel path between the second momentum filter 60 and the detector array 80. The second ion focusing element is configured to focus the third output of molecular analyte ions (the sixth molecular analyte ions) along the second ion travel path to the detector array. The second ion focusing element can be any suitable device capable of focusing the third output of molecular analyte ions (the sixth molecular analyte ions), such as an electrostatic or magnetic lens (e.g., a quadrupole or higher format lens).

The detector array 80 is positioned downstream of the second momentum filter 60 (and the second ion focusing element 70) and is configured to receive the third output of molecular analyte ions (the sixth molecular analyte ions). The detector array may be any suitable device or combination of devices capable of concurrently detecting two or more molecular analyte ions of the third output of molecular analyte ions (the sixth molecular analyte ions), of which the two or more molecular analyte ions have masses that are different from one another (and mass to charge ratios that are different from one another).

The second mass spectrometer 10 can be configured to provide the third output of the molecular analyte ions (the sixth molecular analyte ions) to the detector array 80 at a second mass resolution (which is described in more detail below) of 20,000 or greater. For example, the width of the second entrance slit 39 and the third and fourth radii of curvature of the second energy filter and second momentum filter can be selected to provide a second mass resolution at the detector array of 20,000 or greater. In one embodiment, the third output of molecular analyte ions (the sixth molecular analyte ions) includes at least two ion beams and respective molecular analyte ions of the ion beams have respective masses that differ from one another by about 1 atomic mass unit, and the second width, third and fourth radii of curvature, and detector array are configured to resolve and concurrently detect the at least two ion beams and to distinguish between molecular analyte ions within each ion beam at one part in 20,000. The detector array is configured to concurrently detect the at least two molecular analyte ions. The detector array can be connected to a processor (or processors) 90 (e.g., a computer or computers), which can be configured to acquire data from the detector array and to process the data. As described in more detail below, the processor (e.g., computer) can also be configured to control various features of the second mass spectrometer, such as the detector array. In some embodiments, some components of the second mass spectrometer 10 are controlled by processors separate from and in addition to the processor 90.

Figure 28:
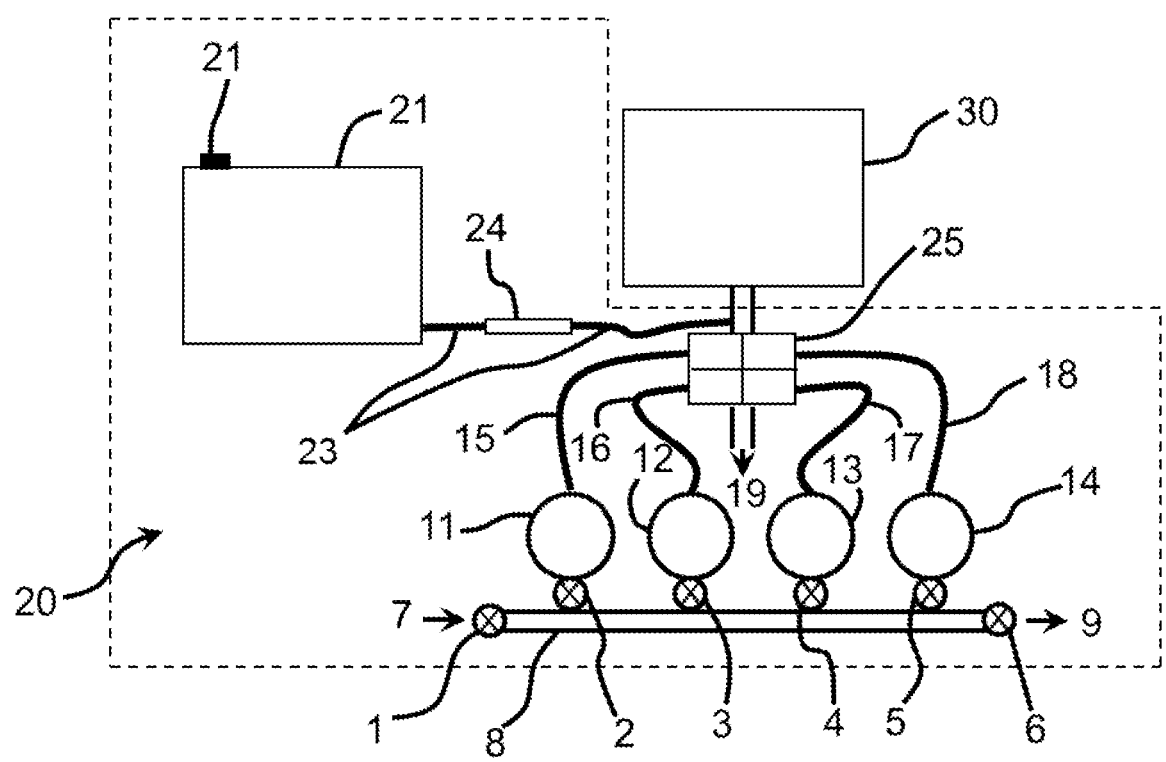
FIG. 28 is a schematic view of a sample introduction system for a mass spectrometer according to one embodiment of the invention.

Embodiments of the individual components of the second mass spectrometer will now be described in more detail. FIG. 28 shows an embodiment of the sample introduction system 20 coupled to the second ion source 30 through five separate conduits (e.g., capillaries). The sample introduction system of FIG. 28 includes a system of valves and reservoirs suitable for alternate introduction of samples and reference standards into a mass spectrometer ion source. Any of the following conduits can be heated to facilitate the delivery of an analyte or reference material to the ion source. The sample introduction system is configured to provide analyte(s) or reference material(s) to the ion source as a neutral gas. The analyte(s) or reference material(s) can be introduced to the second ion source as a pure gas through a viscous capillary bleed (e.g., a flow of gas through a capillary column) or they can be entrained (or mixed) in a flow (e.g., a continuous flow or a pulsed flow) of any suitable carrier gas (e.g., an inert gas, such as helium gas).

The sample introduction system can selectively introduce the analyte or the reference material to the ion source. For example, in the embodiment shown in FIG. 28, the sample introduction system includes an introduction tube 8 configured to receive pure sample gases 7, such as analyte or reference material gases. A first valve 1 (e.g., a first high-vacuum pneumatic valve) is configured to control the flow of the gases into the introduction tube. The introduction tube is further coupled to four sets of valves, bellows and conduits (e.g., capillaries) arranged in parallel and coupled to a valve block configured to selectively couple the introduction tube to the ion source through each set of valves, bellows and conduits.

As shown in FIG. 28, the introduction tube 8 is coupled to a second valve 2, a third valve 3, a fourth valve 4, a fifth valve 5 and a sixth valve 6, each of which can be a high-vacuum pneumatic valve. The second through fifth valves are each configured to selectively couple the introduction tube to a first bellows 11, a second bellows 12, a third bellows 13, and a fourth bellows 14, respectively. The first through fourth bellows 11-14 are each coupled to a first conduit 15, a second conduit 16, a third conduit 17, a fourth conduit 18, respectively. The first through fourth conduits 15-18 (e.g., the first through fourth capillaries) are coupled to a valve block 25 (e.g., a change-over valve block), which is coupled to the second ion source 30. The sixth valve is coupled to a high-vacuum system 9.

By appropriately selecting the first through sixth valves 1-6, a gas, such as an analyte, analytes or reference material, can be introduced into the introduction tube and confined therein. For example, the first valve 1 can be opened to introduce a gas to the introduction tube, and one of the second through fifth valves 2-5 can be selected to couple the introduction tube to one of the first through fourth bellows 11-14, respectively, to thereby provide the gas to the selected bellows. By opening the first valve, a gas can be introduced into the introduction tube, and by opening the second valve 2, the gas can be provided to the first bellows 11. From the first bellows, the gas can then be provided to the first conduit 15 (e.g., the first capillary), which is coupled to the valve block 25. The valve block can selectively couple the first conduit to the second ion source 30. Thus, the sample introduction system 20 can provide a gas to the second ion source through the first valve, the introduction tube, first bellows, first conduit and change-over block. Similarly, other gases can be provided to the second ion source through the first valve, introduction tube, third through fifth valves, second through fourth bellows, second through fourth conduits and valve block. The sixth valve is configured to selectively couple the introduction tube to the high-vacuum (HV) system 9 to evacuate and purge the introduction tube when switching between gases. As shown in FIG. 28, the valve block is also selectively coupled to an HV system 19 configured to evacuate and purge the valve block when switching between gases. The HV systems 9 and 19 can be the same or different. Any of the above-described introduction tube, first through sixth valves, first through fourth bellows and valve block can be heated to facilitate delivery of an analyte or reference material to the ion source.

In the embodiment shown in FIG. 28, the sample introduction system 20 further includes a gas chromatograph 22 coupled to the second ion source 30 through a fifth conduit 23 (e.g., a fifth capillary) including an open split 24. A sample can be injected into the gas chromatograph through an injector 21 and the sample can be separated by the gas chromatograph to provide a purified analyte (e.g., a specific compound or specific set of compounds) to the fifth conduit, which transmits the analyte through the open split to the second ion source. Any suitable gas chromatograph can be used. The analyte can be entrained in a carrier gas flow (e.g., He) that flows through the gas chromatograph, the fifth conduit and the open split to the second ion source. The open split is configured to allow the sample introduction system to provide equivalent conditions to the second ion source regardless of whether an analyte is provided by the chromatograph to the fifth conduit. The fifth conduit and/or open split can be heated to facilitate delivery of an analyte or reference material to the second ion source.

The above-described first through fifth conduits 15-18 and 23 are configured to provide two or more streams of matter (e.g., analyte(s) or reference material(s)) to the second ion source 30. The conduits can be configured to accommodate: (1) a sample of purified compounds that are gases at room temperature; (2) a capillary bleed of carrier gas (e.g., He delivered through the open split 24 and fifth conduit 23); and (3-5) three separate reference materials (e.g., reference gases) that differ from one another in their isotopic compositions by known amounts. With respect to (2), the capillary bleed of carrier gas can be configured to serve as the carrier gas for volatile organic compounds, such as volatile organic compounds introduced through the gas chromatograph 22. Each of the conduits (e.g., capillaries) described above is capable of introducing analyte(s) or reference material(s) to the second ion source as a stream of matter and of being separately and independently selected.

As discussed in more detail below, in some embodiments, measurements of an analyte (or analytes) are standardized to concurrently analyzed standards (e.g., reference materials) and, therefore, the sample introduction system 20 can be configured to deliver the analyte (or analytes) to the second ion source 30 through two or more separate conduits described above. Using the sample introduction system, reference materials can be preselected such that inter-comparison of the reference materials can be used to determine the mass discrimination of the second mass spectrometer source, the reaction constants for relevant fragmentation/adduct reactions at the second ion source, and the linearity of the second mass spectrometer detector system.

Figure 29:
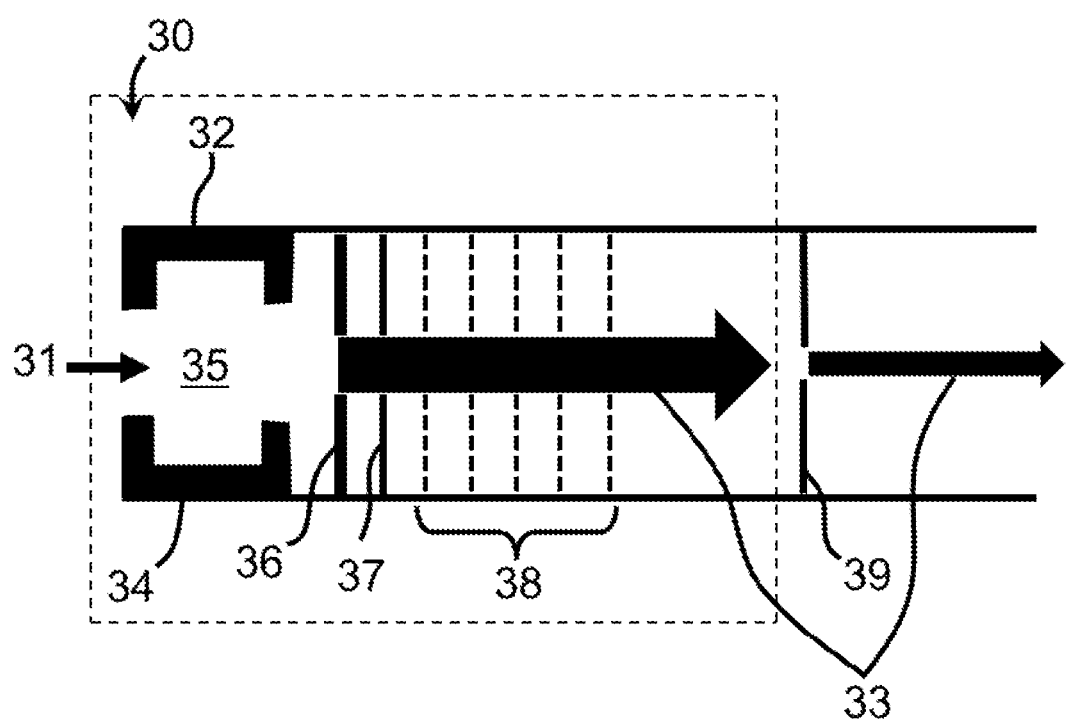
FIG. 29 is a cutaway schematic view of an ion source and entrance slit aperture for a mass spectrometer according to one embodiment of the invention.

The sample introduction system 20 can be any apparatus that is suitable for use with a gas source isotope ratio mass spectrometer, such as, for example, a mercury bellows, an automated mechanical bellows (e.g., the dual inlet systems of the mass spectrometers available from Nu Perspective or the MAT-253 mass spectrometer available from Thermo Fisher Scientific, Inc., Waltham, Mass.), a He-purged carrier gas system that interfaces with a capillary bleed through an open split, or the like. Any apparatus capable of delivering the analyte with flow sufficient to support pressures at the second ion source 30 on the order of $10^{-6}$ mbar can be used. Backing pressures of several mbar to about 1 bar are generally achieved using a capillary bleed having an interior diameter of tens to hundreds of microns. In some embodiments, the second mass spectrometer 10 includes a modified version of the "front end" of the MAT-253 mass spectrometer available from Thermo Fisher Scientific, Inc., including a sample introduction system including 4 bellows and a carrier-gas port (as described above with respect to FIG. 28), and a modified second ion source 30 as shown in FIG. 29. The sample introduction system and second ion source can be modified to have the characteristics described herein and to be compatible with the other components of the second mass spectrometer described herein. For example, in one embodiment, the sample introduction system 20 includes each of the components of the sample introduction system of the MAT-253 mass spectrometer available from Thermo Fisher Scientific, Inc., with the components of the sample introduction system physically rearranged to fit within a cabinet that differs in size and shape from that of the MAT-253.

In the embodiment shown in FIG. 29, the second ion source includes an ionization chamber 35 between a trap 32 (e.g., an anode) and a filament 34 (e.g., a hot cathode). The ion source can further include electrostatic lenses and apertures generally similar to those used in other gas source mass spectrometers. For example, in FIG. 29, the second ion source further includes an extraction lens 36, a shield 37, and focusing/grounding elements 38. Neutral gas 31 (e.g., analyte or reference material gas) enters the ionization chamber and molecular ions are generated by electron impact. The molecular ions are then extracted as an ion beam 33, accelerated and focused by the extraction lens, shield, and focusing/grounding elements. The second ion source can provide molecular ions with an initial acceleration of about 5 kV. In FIG. 29, the second entrance slit 39 is adjacent to the second ion source, and the ion beam is further focused or narrowed as it exits the second ion source through the second entrance slit.

The second ion source 30 can be any suitable ion source, such as those including an electron-impact ionization chamber resembling the Nier-type ion source used in existing gas-source isotope ratio mass spectrometers. For example, the second ion source can be a Nier-type ion source available from Nu Perspective or Thermo Fisher Scientific, Inc. (e.g., the ion source of the MAT-253 mass spectrometer) that has been modified by expanding the range of electron impact energy to extend down to at least 5 eV, rather than the standard lower limit of 50 eV. In one embodiment, the second ion source 30 is the ion source of the MAT-253 mass spectrometer available from Thermo Fisher Scientific, Inc., machined to fit within a housing that differs in size and shape from that of the MAT-253, and machined to fit together with the other components of the second mass spectrometer.

An ion source capable of providing an electron impact energy of less than 50 eV provides improved control over the fragmentation spectrum of the molecular ions as compared to an ion source that has a 50 eV lower limit on electron impact energy. The second ion source can be configured to have a voltage potential between the source filament (e.g., the filament 34) and the housing of the ionization chamber (e.g., the trap 32) that is adjustable in a range of at least 5 eV to less than or equal to 150 eV. For example, the second ion source can be capable of providing an electron impact energy of less than 50 eV, such as an ion source that is configured to provide an electron impact energy of about 5 eV to about 150 eV, or about 25 eV to about 150 eV.

As shown in FIG. 29, the second entrance slit 39 is the last aperture encountered by the ion beam 33 as it exits the second ion source 30. The second entrance slit can be adjacent to the second ion source, and it can be between the second ion source and the detector array 80. In some embodiments, the second entrance slit has a variable aperture. For example, the second entrance slit can be adjustable to a second width in a range of about 10 µm to about 250 µm, such as a second width of 5 µm to about 250µ, or a second width of about 5 µm. The second entrance slit can be adjustable, either continuously or through movement of two or more fixed-width apertures (having the same or different fixed-widths), such that the ion beam width can reach the intended mass resolution of about 20,000 or greater at the detector array. For example, the second entrance slit width can be achieved by using two or more slits movable relative to one another to achieve the desired width. Thus, the second width of the second entrance slit can vary between 5 µm and about 250 µm by way of a mechanical device that translates slits of variable width in and out of the path of the ion beam through the second mass spectrometer analyzer. In some embodiments, when the second mass spectrometer has overall dimensions and ion optics similar to those of conventional high-resolution inductively coupled mass spectrometers, an entrance slit as small as 5 to 10 µm can be used.

Referring back to FIG. 27, the second energy filter 40 is configured to receive the first output of molecular analyte ions (the fourth molecular analyte ions) from the second entrance slit 39. The second energy filter can be any suitable device capable of separating ions according to their energy levels, such as an electrostatic analyzer. The second energy filter can be dynamically pumped to maintain the interior of the second energy filter under high-vacuum. The second energy filter can have a third radius of curvature of about 20 cm to about 25 cm, which may be equal (or roughly equal) to the fourth radius of curvature of the second momentum filter, provided that the kinetic energy of the ions entering the second energy filter is about one half of the kinetic energy that the ions will have when entering the second momentum filter. For example, a third radius of curvature of the second energy filter of about 20 cm to about 25 cm will provide suitable mass resolution at the detectors if the ions are accelerated to one half of their final energy prior to entering the second energy filter and the ions are then accelerated to their full final energy after energy filtering. For example, a third radius of curvature can be about 22 cm. One or more electrostatic lenses may be used to shape, focus and/or center the ion beam before the ion beam enters the second energy filter. Similarly, one or more electrostatic lenses may be used to shape, focus and/or center the ion beam between the second energy filter and the second momentum filter, and/or between the second momentum filter and the detectors. The second energy filter can provide the first output of molecular analyte ions (the fourth molecular analyte ions) with about 5 kV of acceleration in addition to the acceleration provided by the second ion source 30. As an example, the second energy filter can be the energy filter of a Neptune mass spectrometer or Triton mass spectrometer (each of which are available from Thermo Fisher Scientific, Inc.), modified to have the above-described characteristics and to be compatible with the other components of the second mass spectrometer described herein. For example, in one embodiment, the second energy filter is the electrostatic analyzer of the Neptune mass spectrometer available from Thermo Fisher Scientific, Inc.

In FIG. 27, the second energy filter 40 is configured to produce a second output of molecular analyte ions (the fifth molecular analyte ions). The second output can pass through the first ion focusing element 50, which can function as a transfer lens (e.g., a quadrupole or higher format lens). The first ion focusing element can be configured to focus the second output of molecular ions. For example, in one embodiment, the first ion focusing element is one of the ion focusing elements of the Neptune mass spectrometer available from Thermo Fisher Scientific, Inc.

The second momentum filter 60 is positioned downstream from the second energy filter 40 and the first ion focusing element 50, and is configured to receive the second output of molecular analyte ions (the fifth molecular analyte ions). The second momentum filter has a fourth radius of curvature and is configured to filter out sixth molecular analyte ions from the fifth molecular analyte ions according to their momenta. The second momentum filter produces a third output of molecular analyte ions (the sixth molecular analyte ions). The second momentum filter can have a fourth radius of curvature of about 20 cm to about 25 cm. For example, the second momentum filter can include a magnet having a fourth radius of curvature of about 23 cm. As an example, the second momentum filter can be the momentum filter of a Neptune mass spectrometer or Triton mass spectrometer (each of which are available from Thermo Fisher Scientific, Inc.), modified to have the above-described characteristics and to be compatible with the other components of the second mass spectrometer described herein. For example, in one embodiment, the second momentum filter is the magnetic sector of the Neptune mass spectrometer available from Thermo Fisher Scientific, Inc.

A second ion focusing element 70 can be positioned downstream of the second momentum filter 60. The second ion focusing element can be configured to focus the third output of molecular analyte ions (the sixth molecular analyte ions). For example, the second ion focusing element can be a "zoom" lens, such as a dispersion quadrupole or higher format lens. In some embodiments, the second ion focusing element has "zoom" optic capability (±5% mass range) and is configured to provide 2× magnification at the image plane of the detector array 80. For example, in one embodiment, the second ion focusing element is one of the ion focusing elements of the Neptune mass spectrometer available from Thermo Fisher Scientific, Inc.

As shown in FIG. 27, the detector array 80 is positioned downstream of the second momentum filter 60 and the second ion focusing element 70. At least a portion of the molecular ions (e.g., analyte ions, reference material ions, etc.) that pass through the second momentum filter and second ion focusing element are detected at the detector array. For example, the detector array can be configured to receive the third output of molecular analyte ions (the sixth molecular analyte ions) from the second momentum filter.

Figure 30:
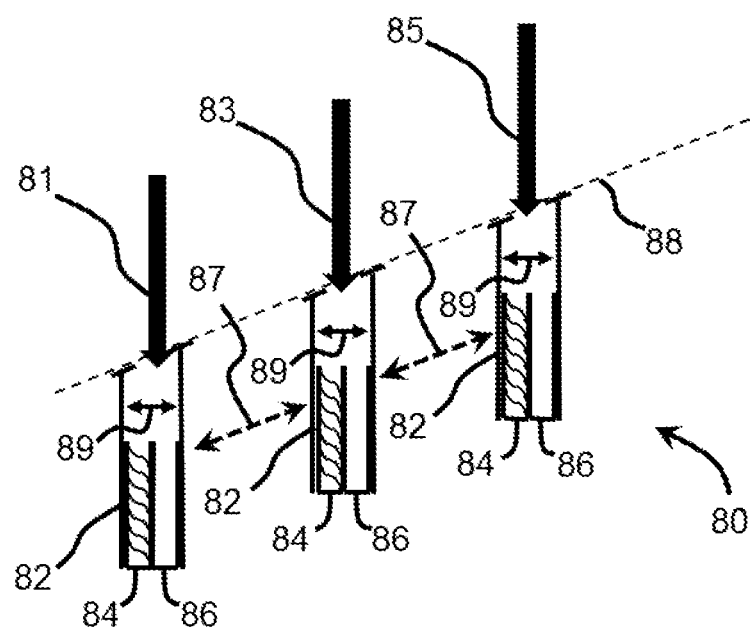
FIG. 30 is a cutaway schematic view of a detector array for a mass spectrometer according to one embodiment of the invention.

The detector array 80 can be a multi-collector array including two or more detectors (e.g., 5 to 10 detectors) capable of faraday-cup or ion counting detection at each of several positions. For example, FIG. 30 is a partial schematic view of the detector array 80 including detectors 82. As shown in FIG. 30, the ion current of the ion beams 81, 83 and 85 arriving at the respective detectors is registered through either an electron multiplier 84 (or ion counting system having similar performance characteristics) or faraday cup 86 current monitoring system to enable quantitative analysis over a large dynamic range in sensitivity at each mass position. The ion beams can include molecular analyte ions or reference material ions, and the ions of the respective ion beams have masses that are different from one another. For example, the third output of molecular analyte ions (the sixth molecular analyte ions) can include the ion beams 81, 83 and 85.

Both the position and sensitivity (e.g., ion counting vs. faraday cup current measurement) of at least one detector 82 can be controlled in an automated fashion (e.g., through the computer 90 of FIG. 27) so that the collection characteristics of the detector can be adjusted on time scales of minutes, without disturbing the delivery of analyte to the second mass spectrometer source or the vacuum within the second mass spectrometer. The foregoing switching capability is beneficial, because most analyses of interest benefit from comparison of measured ratios for two or more molecular or fragment ions derived from the same analyte species (see examples, below).

In some embodiments, the detector array 80 can be reconfigured over the course of measurements made on a single sample (e.g., a single analyte), and the reconfiguration can be both rapid and convenient. At least one of the detectors 82 is capable of movement relative to the other detectors such that the relative positions of detected ions can be adjusted. For example, in FIG. 30, the detectors can vary their relative spacing as shown by the arrows 87. The detectors can vary their position along the focal or image plane of the second mass spectrometer, which is indicated by the dashed line 88. The detectors can be sufficiently mobile to permit rapid reconfiguration to achieve a wide range of relative and absolute mass positions, up to a mass to charge ratio of about 300. Reconfiguration of detector position can be motorized and automated, and can be performed through stepper motors or analogous mechanical devices, which can be controlled and powered remotely through vacuum feedthroughs.

Switching between ion counting and current monitoring detectors at each detector position can be achieved through electrostatic deflectors at the exit slit positioned before each detector position. The arrows 89 indicate the electrostatic deflection that can be used to switch between detection by ion counting (e.g., detection by the electron multiplier 84) and detection by current measurement (e.g., detection by the faraday cup 86).

In one embodiment, the detector array 80 includes seven detectors 82, six of which are movable. Each detector includes a faraday cup (FC) and an electron multiplier (EM), and each detector is switchable between FC and EM measurement. Additionally, signals can be collected from each FC and EM concurrently (or simultaneously). Detector signals are converted to digital measures of intensity (e.g., ion current or counts-per-second rates) using digital-to-analog (DAC) circuits common to the detector systems of several commercially available isotope ratio mass spectrometers, and then delivered to the computer 90 (shown in FIG. 27) capable of storing relative ion beam intensities for later data processing. In one embodiment, the detector array further includes a retarding potential quadrupole (RPQ) lens upstream of the central detector, such that ions pass through the RPQ lens prior to arriving at the central detector.

Examples of suitable detector arrays include the detector arrays of the Cameca ims 1280 microprobe and NanoSIMS ion probes, each available from Cameca, Societe par Actions Simplifiée, and the detector array of the Triton thermal ionization mass spectrometer, available from Thermo Fisher Scientific, Inc.

According to embodiments of the invention, the above-described components can be arranged to provide a double-focusing, normal-geometry sector mass spectrometer having an ion beam size, mass separation and system stability sufficient to achieve a mass resolution at the detector array of 20,000 or greater (mass/$\Delta$M, according to the 5%-95% definition, which is described in more detail below). The second mass spectrometer can have the following capabilities: a vacuum under analytical conditions of not more than $10^{-8}$ mbars; useful ion yield of not less than 1 ion per $5\times10^4$ molecules at the highest mass resolution; a mass range of about 2 to about 300 atomic mass units ("AMU"), such as a mass range of about 2 to about 280 AMU; a mass resolution on the order of 20,000 (according to the mass/$\Delta$M, 5%-95% definition, which is described in more detail below); and abundance sensitivity of not more than $10^{-6}$. Other mass spectrometers are not capable of multi-collection of molecular analyte ions (e.g., concurrently detecting two or more molecular analyte ions, the molecular analyte ions having different masses) generated by electron impact ionization at a mass resolution of 20,000 or greater (as described in more detail below). Embodiments of the invention further include a Nier-type gas source and associated inlet system to the analyzer, such that high-resolution multi-collector mass spectrometry can be performed on molecular ions generated by electron impact on gases and volatile compounds (e.g., volatile organic compounds). The second mass spectrometer has a mass range sufficient for analyzing ions of large volatile organic molecules (e.g., phytane) and their associated fragments. When the second mass spectrometer has a mass resolution at the detector array of 20,000 or greater, the second mass spectrometer can resolve isobaric interferences among isotopologues of organic molecules (e.g., internal isobars, such as isotopologues having the same cardinal mass), their fragments, their adducts, and contaminant species (e.g., contaminants having the same cardinal mass as the molecular analyte ion or molecular analyte fragment ion being measured). These features are not found in other mass spectrometer designs that are also capable of multiple simultaneous collection of two or more ion beams.

Methods

Figure 31:
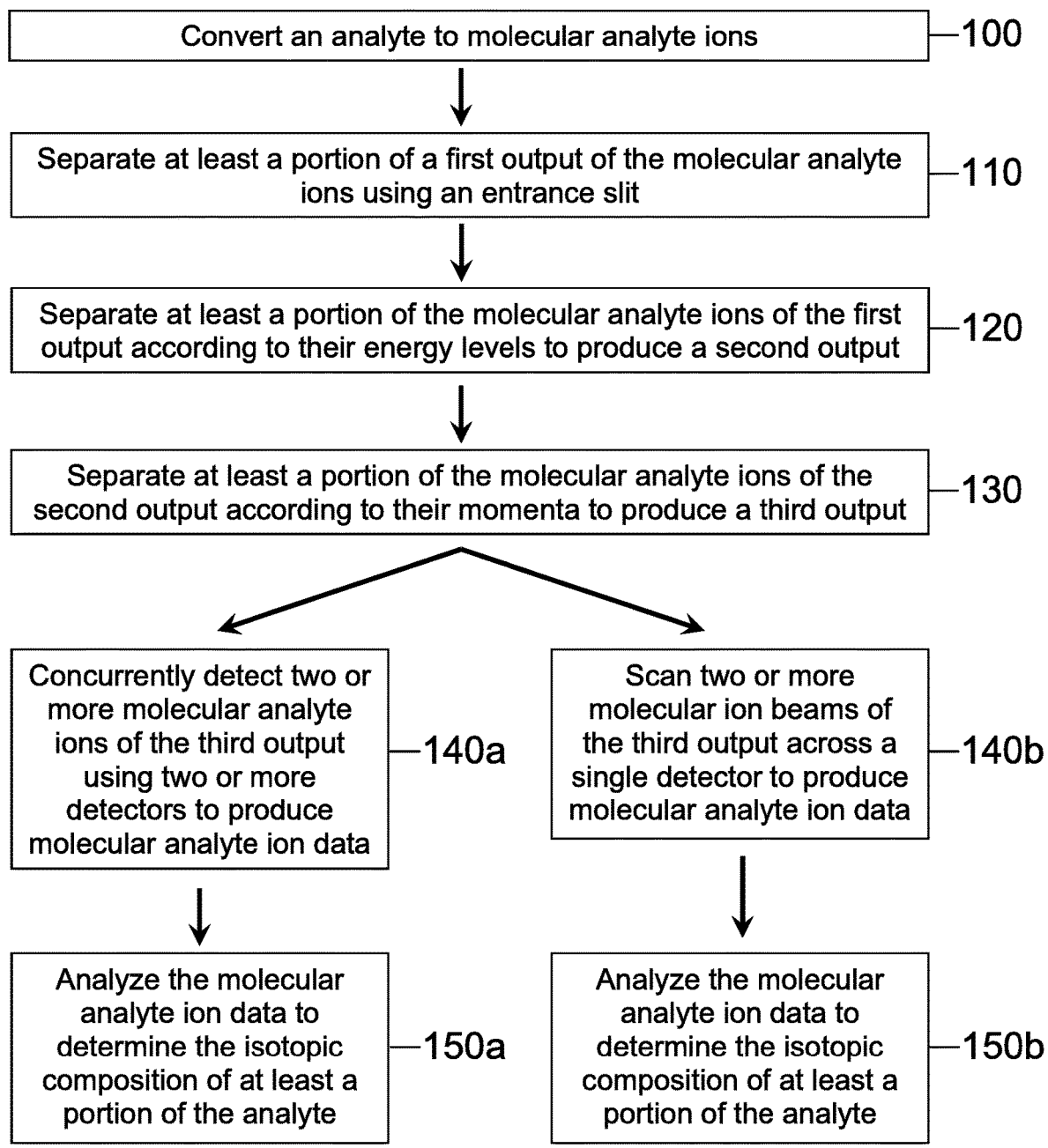
FIG. 31 is a flowchart showing methods for determining the isotopic composition of an analyte in a sample according to embodiments of the invention.

Embodiments of the invention are also directed to methods for determining the isotopic composition of a compound (e.g., an analyte), such as methods of using the above-described second mass spectrometer 10. For example, FIG. 31 is a flow chart illustrating a method for determining the isotopic composition of an analyte in a sample. The method includes (100) converting an analyte to molecular analyte ions. The analyte can be converted to the molecular analyte ions using a second ion source of a second mass spectrometer (e.g., the second ion source 30 described above). The ion source can produce the molecular analyte ions from the analyte. The method further includes (110) separating at least a portion of the molecular analyte ions using a second entrance slit to produce a first output of molecular analyte ions (fourth molecular analyte ions). The molecular analyte ions from the ion source can be separated using the above-described second entrance slit 39 to produce the first output (the fourth molecular analyte ions). As described above, the second entrance slit 39 can have an adjustable second width. The second width can be adjusted to vary the separation of the molecular analyte ions from the second ion source and to adjust the second mass resolution of the spectrometer at the detector array (e.g., the above-described detector array 80).

The method of FIG. 31 also includes (120) further separating at least a portion of the molecular analyte ions of the first output (the fourth molecular analyte ions) according to their energy levels to produce a second output (e.g., filtering out fifth molecular analyte ions from the fourth molecular analyte ions according to their energy levels). The further separating of the molecular analyte ions of the first output can be accomplished using the above-described second energy filter 40 (e.g., the electrostatic analyzer). The degree of the further separation of the molecular analyte ions by the second energy filter depends upon the third radius of curvature of the second energy filter. Thus, as described above, the third radius of curvature of the second energy filter affects the second mass resolution of the spectrometer 10 at the detector array 80. The second energy filter can have any of the above-described third radii of curvature. The second energy filter filters out the fifth molecular analyte ions from the fourth molecular analyte ions according to their energy levels.

The method further includes (130) separating at least a portion of the molecular analyte ions of the second output according to their momenta to produce a third output (e.g., filtering out sixth molecular analyte ions from the fifth molecular analyte ions according to their momenta). The above-described second momentum filter 60 (e.g., the magnetic sector) can be used to separate the molecular analyte ions of the second output according to their momenta. The degree of separation of the molecular analyte ions by the second momentum filter depends upon the fourth radius of curvature of the second momentum filter. Thus, as described above, the fourth radius of curvature of the second momentum filter affects the mass resolution of the spectrometer 10 at the detector array 80. The second momentum filter can have any of the above-described fourth radii of curvature. The second momentum filter filters out the above-described third molecular analyte ions from the second molecular analyte ions according to their momenta.

Multi-Collection/Detection

The method shown in FIG. 31 further includes (140) concurrently detecting (e.g., multi-collection) two or more molecular analyte ions of the third output (the sixth molecular analyte ions) to produce second molecular analyte ion data, the two or more molecular analyte ions having respective masses that are different from one another (and respective mass to charge ratios that are different from one another). As shown in FIG. 31, there are two different approaches to multi-collection.

In the first approach (140a), the two or more molecular analyte ions of the third output (the sixth molecular analyte ions) are detected using two or more detectors to produce the second molecular analyte data. This embodiment is referred to as "parking," since each of the molecular ion beams is "parked" at one detector. According to this embodiment, the analyte may be introduced to the second ion source 30 by the sample introduction system 20 as a continuous flow or as a time resolved pulse. Concurrent detection by parking is suitable for detecting molecular ions having respective masses that differ by at least 1 AMU. Molecular ions that differ by less than 1 AMU may not be sufficiently resolved to be concurrently detected at separate detectors.

Figure 32:
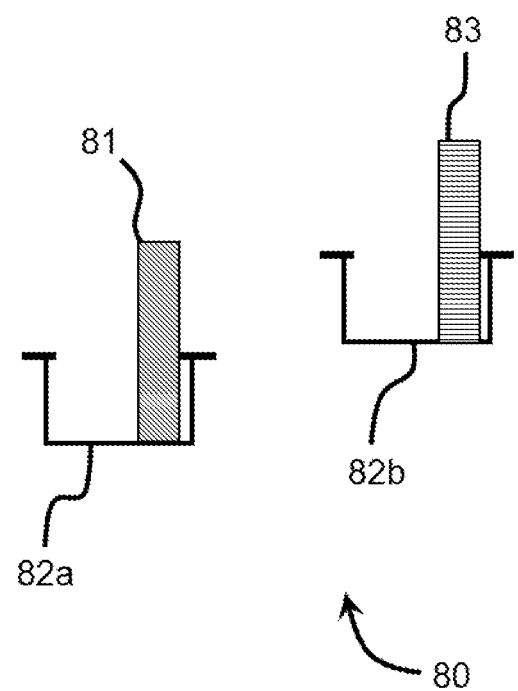
FIG. 32 is a partial schematic view of two detectors of a detector array concurrently detecting two molecular ion beams according to an embodiment of the invention.

According to this embodiment, the two or more molecular ions (e.g., molecular analyte ions) differ from one another by at least 1 AMU and can be concurrently (or simultaneously or quasi-simultaneously) detected in two separate detectors. FIG. 32 shows an example of concurrent detection by "parking" in which a first molecular ion beam 81 is detected at a first detector 82a and a second molecular ion beam 83 is concurrently detected at a second detector 82b. The intensity ratio of these two separately registered (e.g., detected) signals at any one time is the measure of the abundance ratio of the two relevant isotopic species (e.g., the respective molecular ions). The intensities detected (or registered) for the first ion beam 81 and second ion beam 83 are each recorded and averaged over a specified period of time (generally seconds). In FIG. 32, the first detector 82a and the second detector 82b are part of the same detector array 80.

This method of concurrent (or simultaneous or quasi-simultaneous) detection of ions by "parking" can be employed when the intensities of the ion beams exiting the second ion source do not vary substantially over time, for example when delivering a stable (e.g., continuous) flow of gas to the ion source through a capillary bleed, or when the intensities of the ion beams vary through time, for example when analyte is delivered to the second ion source as a brief pulse in a helium carrier gas stream. This method also further includes (150a) analyzing the second molecular analyte ion data to determine the isotopic composition of at least a portion of the analyte. Other ions (e.g., reference material ions) can also be analyzed in the second mass spectrometer in a similar manner.

In the second approach (140b), the two or more molecular analyte ions are detected by scanning the sixth molecular analyte ions (or ion beams including the respective molecular analyte ions) across at least one detector. In some embodiments, scanning at least one molecular analyte ion beam across at least one detector produces a change in a detected signal intensity as masses of molecular analyte ions detected by the detector change at an amount of one part in 20,000. This method is referred to as "peak scanning," since the ion beams are scanned across a detector. This method of scanning can be employed when the analyte is delivered to the second ion source 30 from the sample introduction system 20 as a continuous flow (e.g., through a capillary bleed that varies little in flow rate over time). This method of scanning the ion beams across a single detector is unsuitable, however, for analyses of brief pulses of analyte, such as those delivered to the second ion source as components of a helium carrier gas.

Figure 33A:
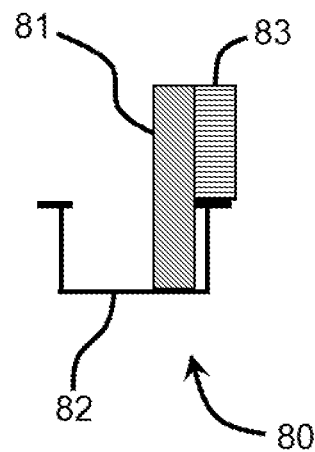
FIGS. 33A-D are partial schematic views showing two molecular ion beams being scanned across a single detector.
Figure 33B:
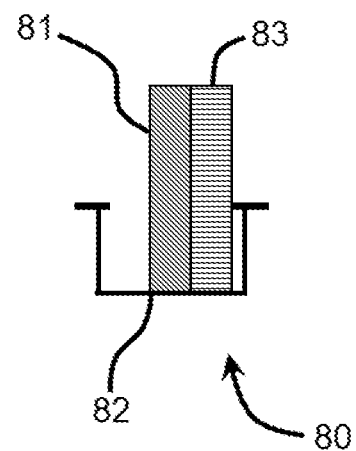
Figure 33C:
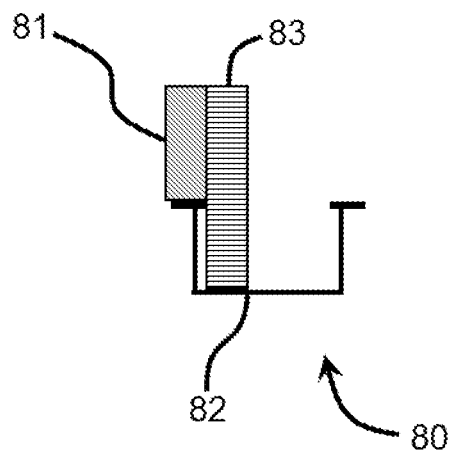
Figure 33D:
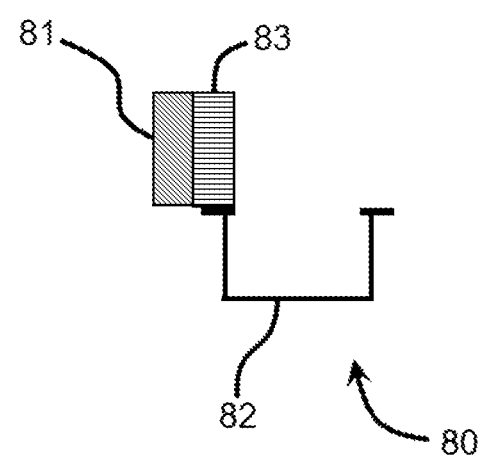
Figure 33E:
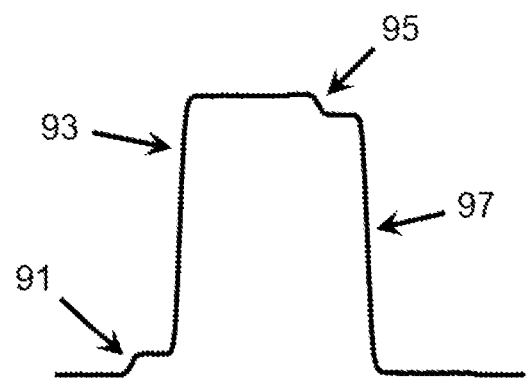
FIG. 33E is a graph showing the resultant mass spectrum.

FIGS. 33A-D illustrate the scanning of a first molecular ion beam 81 and a second molecular ion beam 83 across a single detector 82 of a detector array 80. FIG. 33E illustrates the mass spectrum that results from the scanning of the ion beams across the single detector in FIGS. 33A-D. As shown in FIG. 33A, the first molecular ion beam enters the detector first. In the mass spectrum of FIG. 33E, the first molecular ion beam is shown entering the detector at 91. Then, as shown in FIG. 33B, the second molecular ion beam enters the detector, resulting in both ion beams being detected concurrently (or simultaneously) in the detector. The second molecular ion beam is shown entering the detector at 93 of the mass spectrum of FIG. 33E, at which point the measured signal is a composite signal that includes a contribution from each of the first and second molecular ion beams. Then, the first molecular ion beam exits the detector as shown in FIG. 33C. At this point only the second molecular ion beam is detected in the detector. The first molecular ion beam is shown leaving the detector at 95 of the mass spectrum of FIG. 33E. Then, as shown in FIG. 33D, the second molecular ion beam exits the detector. The second molecular ion beam is shown leaving the detector at 97 of the mass spectrum of FIG. 33E.

Figure 33F:
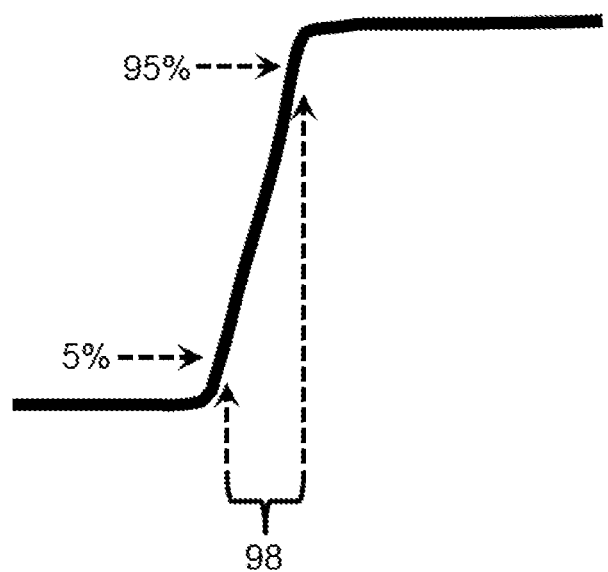
FIG. 33F is a schematic view showing the components of a signal intensity used for calculating mass resolution.

FIG. 33F illustrates the portions of a measured signal intensity that can be used to calculate the first mass resolution of the first mass spectrometer at the detector or the second mass resolution of the second mass spectrometer at the detector array. In FIG. 33F, 90% (5%-95%) of the measured signal intensity for a particular mass is contained in the width ΔM between the two vertical arrows. The mass resolution can be calculated by dividing the mass of the ion measured by the width ΔM. Accordingly, as used herein, the term "mass resolution" refers to the value calculated by dividing the mass of the ion measured by the width ΔM that contains 90% of the measured signal intensity.

The above-described scanning results in a time-varying detected ion beam intensity in the detector across which the ion beams are scanned, with an example of a resultant mass spectrum shown in FIG. 33E. The scanning can take place over a time period of seconds or minutes. The ion beams can be scanned by adjusting the accelerating potential of the ion beams (e.g., by adjusting the accelerating potential of the ion source 30 or the energy filter 40) or by adjusting the magnetic field strength of the second momentum filter 60 (e.g., by adjusting the intensity of a current delivered to an electromagnet included in the second momentum filter).

The peak scanning method of detecting ions can be employed when the ion beams include respective ions that have similar, but not identical, mass to charge ratios (e.g., the respective ions each have the same cardinal mass but are at least partially discriminated from one another in the second mass spectrometer analyzer). Accordingly, the peak scanning approach can be applied when the sixth molecular analyte ions have respective masses that differ from one another by less than 1 AMU. The peak scanning approach can also be applied when the sixth molecular analyte ions have respective masses that differ from one another by at least 1 AMU (or more than 1 AMU). This method also further includes (150b) analyzing the molecular analyte ion data to determine the isotopic composition of at least a portion of the analyte. Other ions (e.g., reference material ions) can be analyzed in the second mass spectrometer in a similar manner. While the above-described "parking" approach and "peak-scanning" approach can be carried out separately, measurements made using parking and peak-scanning can be used in a single analysis.

The above-described analyzing, as well as that described below, can be carried out as described in the above referenced U.S. Provisional Application No. 61/652,095, filed on May 25, 2012, the entire contents of which are incorporated herein by reference. The analyzing can also utilize one or more databases of isotopic information. The databases can be generated using the methods and apparatus described herein, or they can be generated using numerical simulations. A person of skill in the art would recognize the type of isotopic information that should be included in a database to be used in the methods described herein. For example, such databases would include commonly observed proportions of fragment and adduct ions in the full mass spectrum of analytes of interest, as measured under common (or consistent) instrumental tuning conditions (including properties such as the electron impact energy of the ion source and source pressure of the analyte or compound being introduced into the second mass spectrometer).

Standardization

All analyses described herein can be standardized by comparison with reference materials (e.g., reference analytes) having known (or preset) isotopic compositions, including predetermined (or preset) proportions (or concentrations) of isotopologues of interest. The reference materials can be analyzed under conditions (i.e., chemical purity, ion-source pressure and instrument settings) that are closely similar to those of the unknown samples (e.g., the analyte). Additionally, the reference materials can be converted to ions, separated and detected according the methods described above with respect to the analyte. The description provided below illustrates some means by which these standards can be created and characterized. As described below, analysis of the standards (e.g., reference materials) can be used to calibrate several instrumental artifacts.

For example, standardization can include alternate measurement of a sample (e.g., an analyte) and a standard (e.g., one or more reference materials) according to the methods described herein (e.g., converting the analyte or standard to ions, separating and detecting the ions as described above with respect to the analyte). In one embodiment, each of the analyte and the standard is drawn from a relatively large (~$10^{-6}$ mol or larger) reservoir of gas (e.g., a gas containing the analyte or standard) and delivered to the second ion source through a capillary bleed (e.g., one of the conduits 15-18 described with respect to FIG. 28) at a rate that varies little with time (e.g., as a continuous flow). For example, the standard can be drawn from the relatively large reservoir of gas by the sample introduction system and introduced into the second ion source. The standard can then be converted to ions by the second ion source and the ions can be separated by the second entrance slit, the second energy filter and the second momentum filter. The separated ions of the standard can be detected by the detectors and then analyzed. The process can then be repeated for analyte drawn from another relatively large reservoir of gas that is different from the standard. The process can also then be repeated for another standard that is the same as or different from the first standard. Each time the gas stream entering the second ion source (e.g., the second ion source 30) is alternated from sample to standard or standard to sample, the operator can wait several seconds until ion intensities reach stable, relatively time-invariant values before recording signal intensities.

As with the analyte, reference materials delivered by the sample introduction system 20 as a continuous flow can be detected by either concurrently detecting the reference material ions using two or more detectors (e.g., the above-described concurrent detection 140a or "parking") or by scanning the reference material ion across at least one detector (e.g., the above-described concurrent detection 140b or "peak scanning").

When the reference material ions are concurrently detected by two or more detectors (e.g., the above-described concurrent detection 140a or "parking"), intensities detected (or registered) for two or more separate masses are recorded and averaged over a specified period of time (generally seconds) before switching the gas flow to another reservoir (e.g., from sample to standard or standard to sample). This process is repeated two or more times, generating a time series of observations of two or more ion intensities (and thus one or more intensity ratios) for sample (e.g., analyte) and standard (e.g., reference material). Interpolation between any two standard measurements provides the basis for standardizing the intervening sample measurement. Aspects of this method are based on techniques common to existing dual-inlet gas source isotope ratio mass spectrometers.

When the reference material ions are concurrently detected according to the "peak scanning" approach 140b, all reference ion beams having a single cardinal mass are scanned across at least one detector 82 (e.g., at least one collector). The reference ion beams can be scanned by adjusting the accelerating potential of the ion beams (e.g., by adjusting the accelerating potential of the second ion source 30 or the second energy filter 40) or by adjusting the magnetic field strength of the second momentum filter 60 (e.g., by adjusting the intensity of a current delivered to an electromagnet included in the second momentum filter).

As with the analyte, the "peak scanning" can be done using a single detector, or using two or more detectors as part of the same scan. This results in a time varying intensity at each detector, where variations in intensity reflect changing proportions of the various ion species that contribute to the population of ions at each cardinal mass, as shown in the mass spectrum of FIG. 33E. According to this embodiment, gas flow to the second ion source should be relatively stable over the time scale of each scan (though subtle variations may be corrected for by introducing a modest correction to intensity as a function of time to account for depletion of a vapor reservoir being analyzed, or other similar artifacts). Resulting composite peaks can be de-convolved for the relative intensities of their component ion beams by methods readily understood by those of skill in the art, such as through an algorithm that assumes an initial guess as to the number, identity and relative intensities of the component ion beams and then iteratively solves for the least-squares best fit relative intensities of those ion beams.

For example, a program, such as a MATLAB® script (MATLAB is a registered trademark of The Mathworks Inc., Delaware USA), can be used to construct a synthetic data set by stipulating, for example, the shapes of the ion beams (e.g., the widths of the ion beams), the width of the detector, the intensity of a first ion beam, and the intensity of a second ion beam. The program can then produce a simulated mass spectrum based on the stipulated conditions and compare the simulated mass spectrum to the measured mass spectrum. The program can then iteratively solve for the least-squares best fit relative intensities of the ion beams (e.g., by searching for the set of conditions that best match the measured mass spectrum) to thereby determine the relative contribution of each ion beam to the measured mass spectrum. Standardization can be achieved by performing the above-described operations for a standard gas stream (e.g., analyte or reference material of the same chemical composition and source pressure as the sample but having a known or preset composition) near in time to the analysis of the sample (e.g., the analyte), and under closely or relatively similar source pressures and instrument settings to those used for the sample. The relative intensities of component ion beams determined for sample (e.g., analyte) and standard (e.g., reference material) are recorded and used in one or more of the standardization schemes described below.

In an alternative embodiment, a sample (e.g., an analyte) and a standard (e.g., a reference material) can be measured alternately, where each is introduced to the second ion source (e.g., the second ion source 30) through time-resolved pulses contained within a helium carrier gas stream that continuously flows into the second ion source or is added to the second ion source through a separate capillary bleed concurrent with introduction of the helium carrier gas. According to this embodiment, the method includes concurrently detecting (e.g., concurrently detecting according to the "parking" 140a described above), for any one pulse of sample (standard or analyte), the ion intensity of molecular ions having two or more different masses for any one pulse of sample, standard or analyte, the masses of the molecular ions differing from one another by at least 1 AMU. The ion intensities are integrated over the duration of the pulse. Signals registered during periods of unstable or negligibly small signal intensities at the beginning and end of each pulse can be omitted to improve the quality of the data obtained. Standardization can be achieved by comparing ion intensity ratios measured for pulses of the analyte of the sample to those measured for pulses of the standard (e.g., the reference material) introduced before and/or after the sample analyte pulse, either by the averaging of all bracketing standard analyses or by interpolation between any two bracketing standard analyses. Aspects of this method are based on that common to existing carrier gas isotope ratio mass spectrometers.

Examples of several parameters (e.g., instrumental artifacts) that can be standardized are described in more detail below.

Instrumental Mass Bias

Figure 34:
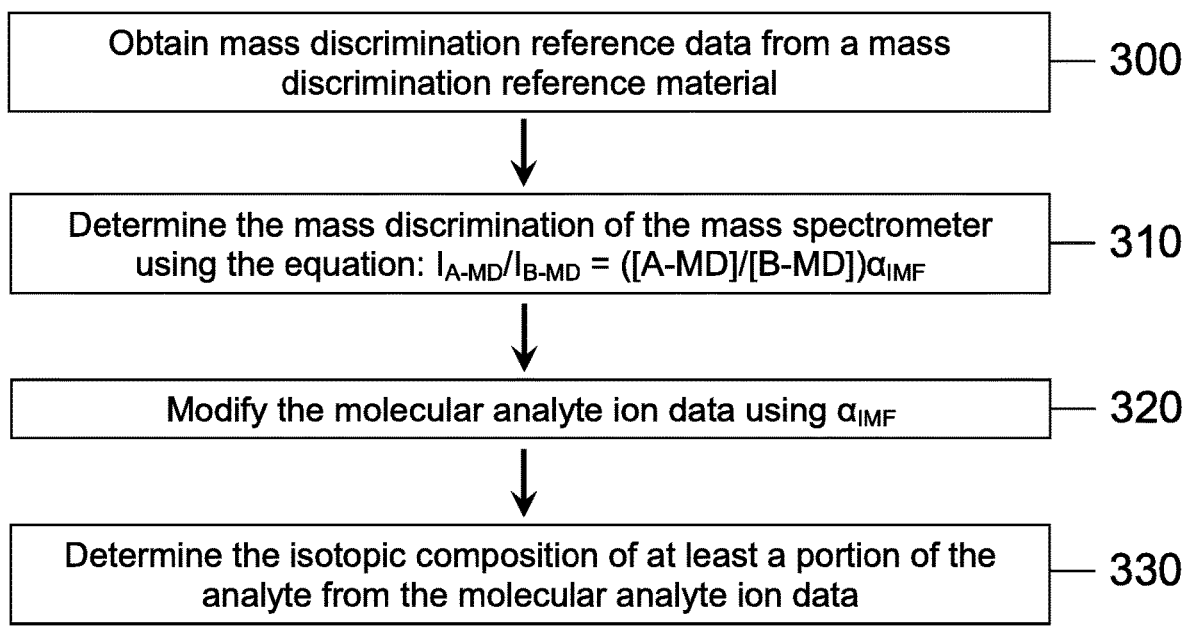
FIG. 34 is a flowchart showing a component of a method for determining the isotopic composition of an analyte in a sample according to an embodiment of the invention.

The mass discrimination in the above-described second ion source 30, second energy filter 40 and detector array 80 of the second mass spectrometer 10 can be calibrated by comparing mass discrimination reference data (e.g., an ion intensity ($I_i$) ratio) for two or more mass discrimination reference ion beams to the known (or preset) concentrations of the isotopologues or isotopomers from which the mass discrimination reference ion beams are produced by electron impact ionization. For example, as shown in FIG. 34, calibrating the mass discrimination of the second mass spectrometer can include (300) obtaining mass discrimination reference data from a mass discrimination reference material including mass discrimination reference isotopologues or isotopomers A-MD and B-MD that differ in their respective mass to charge ratios and have respective mass discrimination reference concentrations [A-MD] and [B-MD]. The mass discrimination reference data can be obtained by analyzing the mass discrimination reference material according to the methods described above with respect to the analyte. The mass discrimination reference data includes mass discrimination reference ion intensities $I_{A\text{-}MD}$ and $I_{B\text{-}MD}$ corresponding to the respective mass discrimination reference isotopologues or isotopomers A-MD and B-MD. The method according to this embodiment can further include (310) determining the mass discrimination of the second mass spectrometer by comparing a ratio of the mass discrimination reference ion intensities $I_{A\text{-}MD}$ and $I_{B\text{-}MD}$ to a ratio of the mass discrimination reference concentrations [A-MD] and [B-MD] using a constant of proportionality $\alpha_{IMF}$ according to the Equation:

$$I_{A\text{-}MD}/I_{B\text{-}MD}=([A\text{-}MD]/[B\text{-}MD])\alpha_{IMF}$$

The molecular analyte ion data acquired according to the methods described above can then be modified using the constant of proportionality $\alpha_{IMF}$ (320). The isotopic composition of at least a portion of the analyte can then be determined from the modified molecular analyte ion data.

Instrument Linearity

Figure 35:
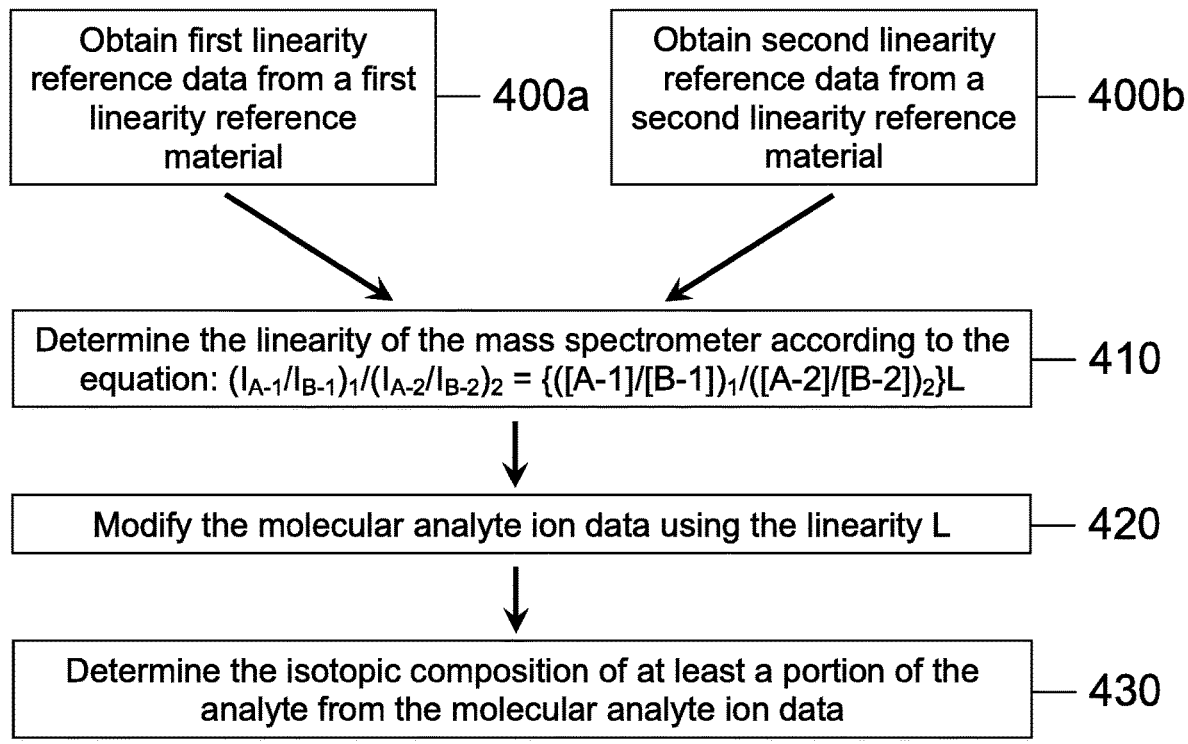
FIG. 35 is a flowchart showing a component of a method for determining the isotopic composition of an analyte in a sample according to an embodiment of the invention.

The instrument "linearity" (L) can be defined as a constant of proportionality between a measured ratio of reference ion intensity ratios for two reference materials (e.g., standards) to a ratio of abundance ratios of the relevant parent isotopologues or isotopomers. For example, as shown in FIG. 35, calibrating the linearity of the second mass spectrometer 10 can include (400a) obtaining first linearity reference data from a first linearity reference material including first linearity reference isotopologues or isotopomers A-1 and B-1 at a first linearity reference concentration ratio $([A\text{-}1]/[B\text{-}1])_1$. The first linearity reference data can be obtained by analyzing the first linearity reference material according to the methods described above with respect to the analyte. The first linearity reference data includes a first linearity reference intensity ratio $(I_{A\text{-}1}/I_{B\text{-}1})_1$ corresponding to the first linearity reference isotopologues or isotopomers A-1 and B-1. The method further includes (400b) obtaining second linearity reference data from a second linearity reference material including second linearity reference isotopologues or isotopomers A-2 and B-2 at a second linearity reference concentration ratio $([A\text{-}2]/[B\text{-}2])_2$. The second linearity reference data can be obtained by analyzing the second linearity reference material according to the methods described above with respect to the analyte. The second linearity reference data includes a second linearity reference intensity ratio $(I_{A\text{-}2}/I_{B\text{-}2})_2$ corresponding to the second linearity reference isotopologues or isotopomers A-2 and B-2 (400b). The method further includes (410) determining the linearity (L) of the second mass spectrometer according to the Equation:

$$(I_{A-1}/I_{B-1})_1/(I_{A-2}/I_{B-2})_2 = \{([A-1]/[B-1])_1/([A-1]/[B-2])_2\}L$$

The method can further include modifying the molecular analyte ion data using the linearity L (420). The isotopic composition of at least a portion of the analyte can then be determined from the modified molecular analyte ion data (430). The linearity of the second mass spectrometer is an empirically measured analytical artifact and is expected to be specific to each instrument, analytical condition (e.g., analyte type, source pressure and instrument tuning condition) and measured ratio of interest. Thus, it can be calibrated by comparison of two or more standards (e.g., reference materials) that differ by a known (or preset) amount in abundance ratios of isotopic species of interest.

Fragmentation Probability

Some embodiments of the invention include measurements of ions that are charged fragments of analyte molecules. As a result, it can be useful to calibrate a relationship between an ion intensity of a fragment of interest (e.g., a molecular analyte fragment ion intensity or $I_{FA}$) to an intensity of corresponding to an ion of the intact molecule from which it is derived (e.g., an intact molecular analyte ion intensity or $I_{A\text{-}molecular}$). This can be achieved by calibration of a constant of proportionality $K_{fragmentation}$ for the fragmentation reaction through analysis of the intensity ratio of the molecular analyte fragment ion to the intact molecular analyte ion. For example, the molecular analyte ions can include the intact molecular analyte ions and the molecular analyte fragment ions. Each of the molecular analyte ions are formed by ionizing an intact molecule of the analyte and each of the molecular analyte fragment ions are formed by dissociating one or more of the intact molecules of the analyte or the intact molecular analyte ions. Additionally, the molecular analyte ion data includes the molecular ion intensity $I_{A\text{-}molecular}$ corresponding to one or more of the intact molecular analyte ions. The molecular analyte ion data also includes the molecular analyte fragment ion intensity $I_{FA}$ corresponding to one or more of the molecular analyte fragment ions.

Figure 36:
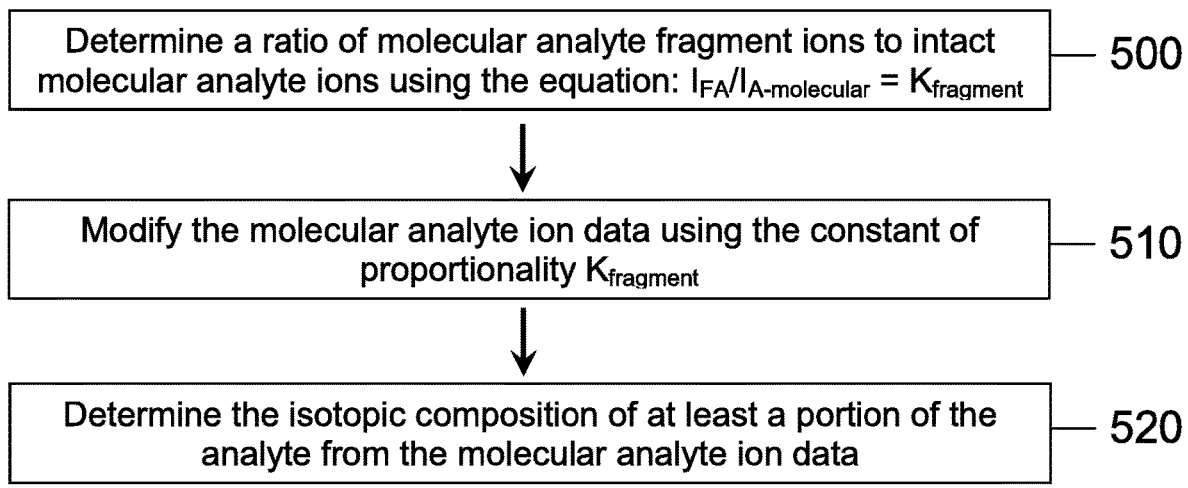
FIG. 36 is a flowchart showing a component of a method for determining the isotopic composition of an analyte in a sample according to an embodiment of the invention.

As shown in FIG. 36, embodiments of the invention include (500) determining a ratio of the molecular analyte fragment ions to the intact molecular analyte ions by calculating a constant of proportionality $K_{fragment}$ according to the Equation:

$$I_{FA}/I_{A\text{-}molecular} = K_{fragment}$$

The method also includes modifying the molecular analyte ion data using the constant of proportionality $K_{fragment}$ (510). The isotopic composition of at least a portion of the analyte can then be determined from the modified molecular analyte ion data (520). The constant of proportionality $K_{fragment}$ is an empirically measured analytical artifact, and is expected to be specific to each instrument, analytical condition (e.g., analyte type, source pressure and instrument tuning condition) and measured ratio of interest.

Adduct Probability

Some embodiments of the invention include measurements of ions that are ions or ionic fragments of the analyte molecules which have gained one or more excess H (or, potentially, other) atoms. As a result, it can be useful to calibrate a relationship between an ion intensity of adduct ions of interest (e.g., an analyte adduct ion intensity or $I_{A'\text{-}adduct}$) to an intensity corresponding to an ion of the un-adducted molecule from which it is derived (e.g., the molecular analyte ion intensity or $I_{A\text{-}molecular}$). This can be achieved by calibration of a constant of proportionality $K_{adduct}$ for the adduction reaction through analysis of the intensity ratio of the molecular analyte adduct ion to the intact molecular analyte ion. For example, the molecular analyte ions can include intact molecular analyte ions and analyte adduct ions. Each of the intact molecular analyte ions are formed by ionizing an intact molecule of the analyte and each of the molecular analyte adduct ions are formed by combining one or more of the intact molecules of the analyte or the analyte ions and a hydrogen atom or an other material, the other material being the same as or different from the analyte molecules or the analyte ions. Additionally, the molecular analyte ion data includes an intact molecular analyte ion intensity $I_{A\text{-}molecular}$ corresponding to one or more of the intact molecular analyte ions and a molecular analyte adduct ion intensity $I_{A'\text{-}adduct}$ corresponding to one or more of the molecular analyte adduct ions.

Figure 37:
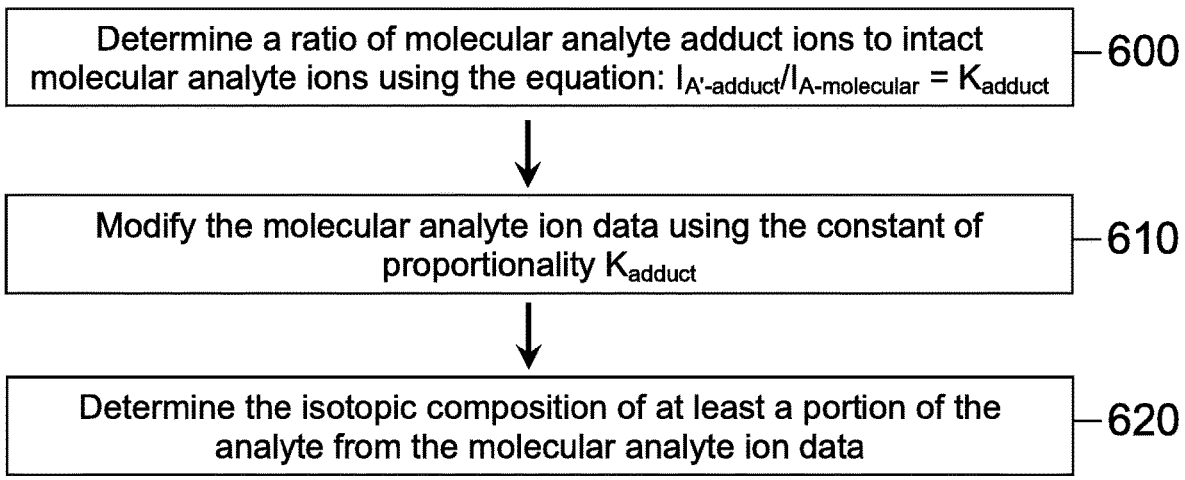
FIG. 37 is a flowchart showing a component of a method for determining the isotopic composition of an analyte in a sample according to an embodiment of the invention.

As shown in FIG. 37, embodiments of the invention include (600) determining a ratio of the molecular analyte adduct ions to the intact molecular analyte ions by calculating a constant of proportionality $K_{adduct}$ according to the Equation:

$$I_{A'\text{-}adduct}/I_{A\text{-}molecular} = K_{adduct}$$

The method further includes modifying the molecular analyte ion data using the constant of proportionality $K_{adduct}$ (610). The isotopic composition of at least a portion of the analyte can then be determined from the modified molecular analyte ion data (620). The constant of proportionality $K_{adduct}$ is an empirically measured analytical artifact, and is expected to be specific to each instrument, analytical condition (e.g., analyte type, source pressure and instrument tuning condition) and measured ratio of interest. The constant of proportionality $K_{adduct}$ is also expected to vary with the partial pressure of water in the ion source, and/or abundances in the ion source of other potential sources of H other than the analyte molecules.

Redistribution or Recombination Probability

Molecular ions can be generated by chains of electron-molecule, electron-ion, ion-ion and ion-molecule reactions that result in fragmentation of a parent species (e.g., an intact analyte molecule) and recombination of the resultant fragments to re-form ions that are indistinguishable in mass from the parent molecule (e.g., the intact analyte molecule or an ion thereof). Such reactions are sufficiently energetic that they effectively drive the sample (e.g., the analyte) toward a random distribution of isotopes among all possible isotopologues. Such effects, sometimes referred to as "scrambling," commonly result in redistribution of isotopes among isotopologues of approximately several percent, relative, of all measured molecular ions (e.g., molecular analyte ions). The foregoing effects can be standardized by comparison of two or more standards (e.g., reference materials) that differ by known (or preset) amounts in their isotopic distributions. In most instances, these effects cannot be standardized through analysis of a single ion beam intensity or ion intensity ratio; rather, one must monitor the change from expected values of the equilibrium constant for an isotope exchange reaction involving a homogeneous reaction among isotopologues of the same molecule.

Figure 38:
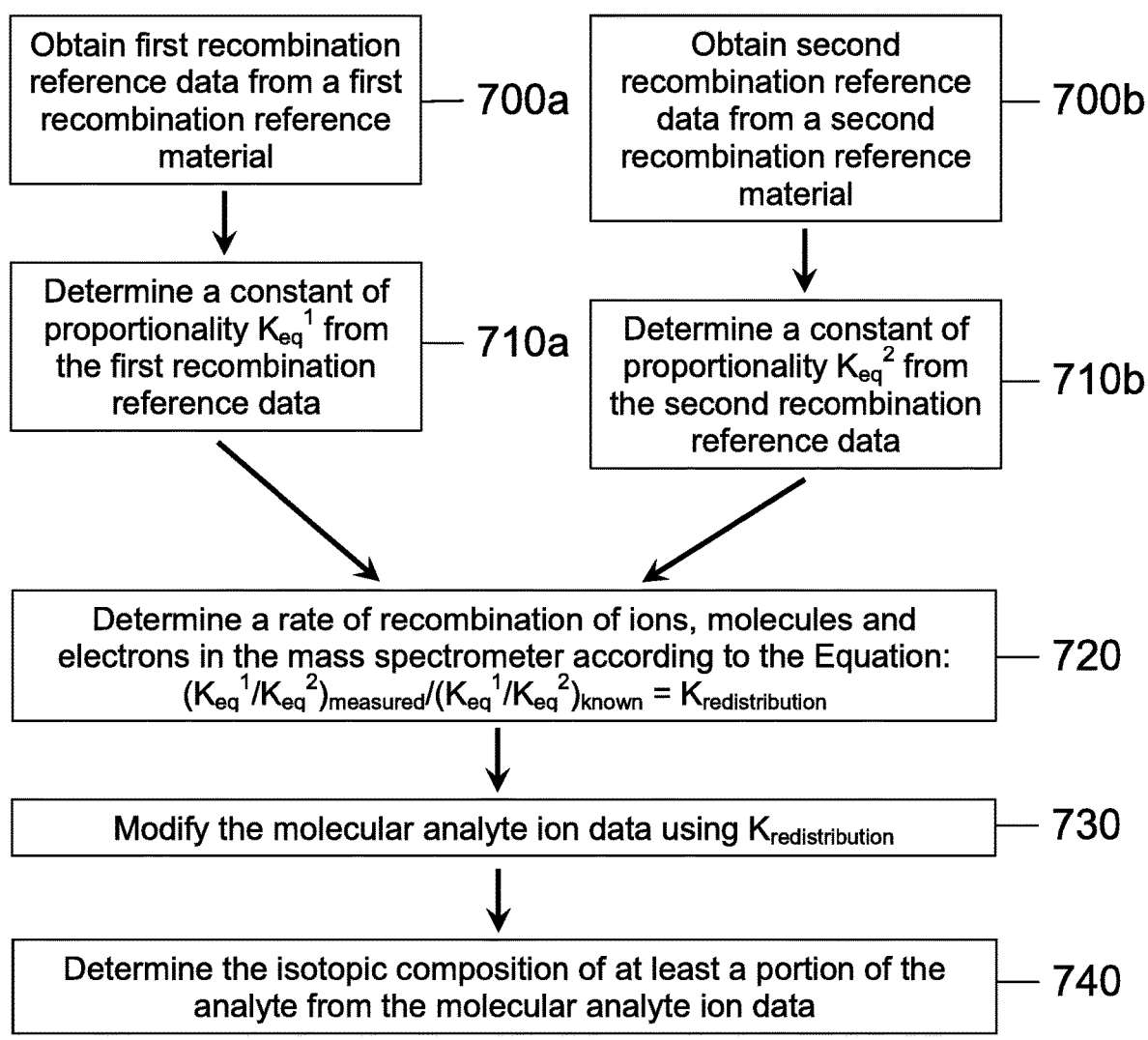
FIG. 38 is a flowchart showing a component of a method for determining the isotopic composition of an analyte in a sample according to an embodiment of the invention.

For example, as shown in FIG. 38, the method according to embodiments of the invention can include (700a) obtaining first recombination reference data from a first recombination reference material including first recombination reference isotopologues or isotopomers A-1 and B-1 and having a preset first recombination reference ratio of the first recombination reference isotopologues or isotopomers A-1 to the first recombination reference isotopologues or isotopomers B-1. The first recombination reference data can be obtained by analyzing the first recombination reference material according to the methods described above with respect to the analyte. The method also includes (710a) determining a constant of proportionality $K_{eq}^1$ from the first recombination reference data. The method further includes (700b) obtaining second recombination reference data from a second recombination reference material including second recombination reference isotopologues or isotopomers A-2 and B-2 and having a preset second recombination reference ratio of the second recombination reference isotopologues or isotopomers A-2 to the second recombination reference isotopologues or isotopomers B-2. The second recombination reference data can be obtained by analyzing the second recombination reference material according to the methods described above with respect to the analyte. The method also further includes (710b) determining a constant of proportionality $K_{eq}^2$ from the second recombination reference data, and (720) determining a rate of recombination of ions, molecules and electrons in the second mass spectrometer according to the Equation:

$$(K_{eq}^1/K_{eq}^2)_{measured}/(K_{eq}^1/K_{eq}^2)_{known} = K_{redistribution}$$

The method also includes modifying the molecular analyte ion data using the constant of proportionality $K_{redistribution}$ (730). The isotopic composition of at least a portion of the analyte can then be determined from the modified molecular analyte ion data (740).

As an example of recombination and redistribution, $K_{eq}$ can be defined to be the equilibrium constant for the following reaction among methane isotopologues:

$$^{13}CH_4 + {}^{12}CH_3D \leftrightarrow {}^{13}CH_3D + {}^{12}CH_4$$

Figure 39:
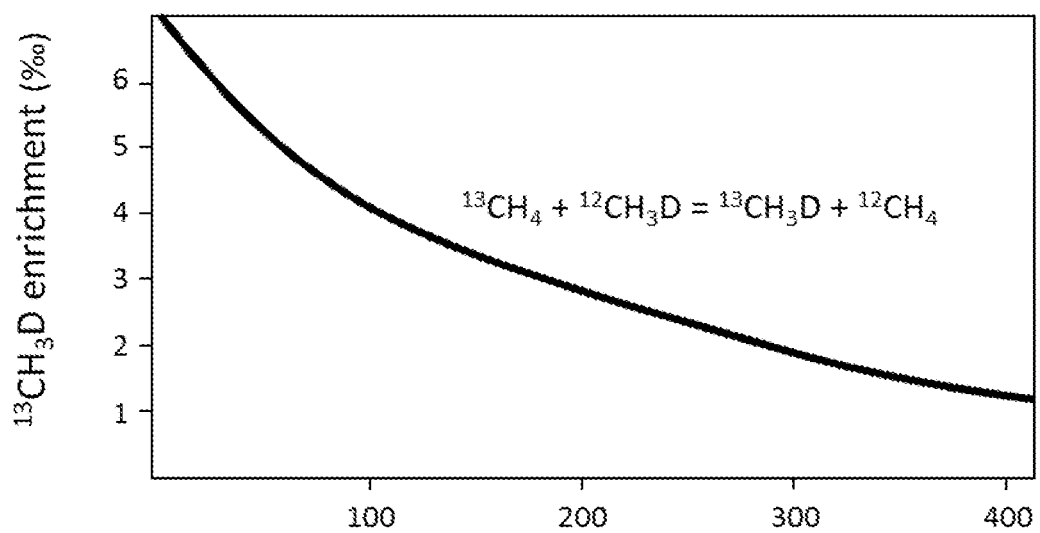
FIG. 39 is a graph illustrating the temperature dependence of isotope exchange reactions involving homogeneous equilibria of methane isotopologues, including multiply substituted isotopologues.

For example, $K_{eq} = [^{13}CH_3D][^{12}CH_4]/[^{13}CH_4][^{12}CH_3D]$, and $K_{eq}$ can be determined as the product of two isotopologue ratios (e.g., $[^{13}CH_3D]/[^{12}CH_3D] \times [^{12}CH_4]/[^{13}CH_4]$). As set forth above, a correction factor for redistribution through "scrambling" (e.g., $K_{redistribution}$) can be calculated through comparison of values of $K_{eq}$ for two known standards (e.g., reference materials), $K_{eq}^1$ and $K_{eq}^2$. FIG. 39 is a graph illustrating the temperature dependence of the reaction $^{13}CH_4 + {}^{12}CH_3D \leftrightarrow {}^{13}CH_3D + {}^{12}CH_4$. As can be seen in FIG. 39, $^{13}CH_3D$ enrichment decreases as the temperature increases.

Migration Probability

Figure 40:
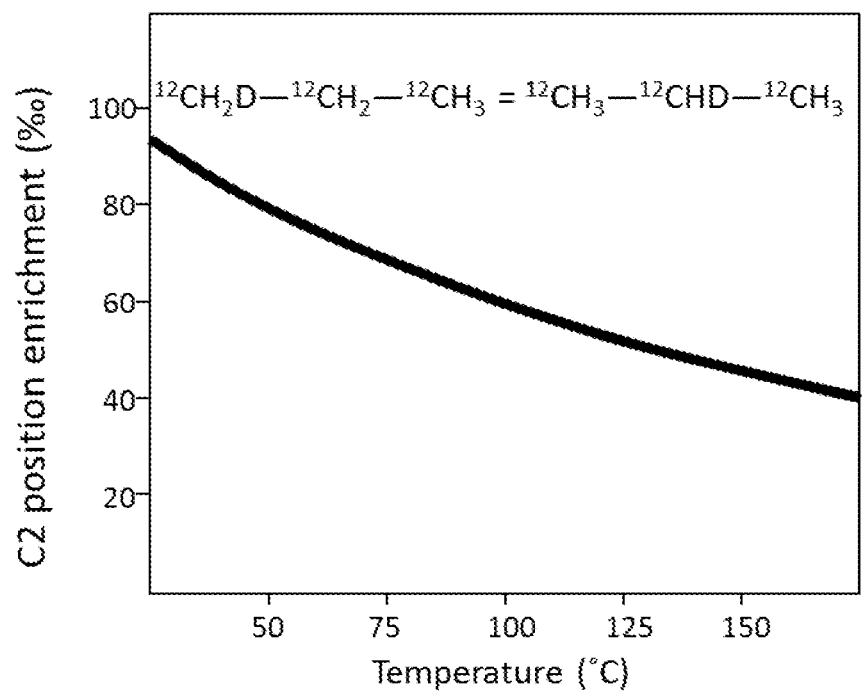
FIG. 40 is a graph illustrating the temperature dependence of an intramolecular exchange process in propane.

Electron impact ionization is capable of driving migration of atoms between positions of an ion (e.g., an intact molecular analyte ion, an analyte fragment ion or a molecular analyte adduct ion). For example, the term "migration" can be used to describe the process by which a hydrogen atom in a methyl ($CH_3$) group of a propane molecule trades positions with a hydrogen atom in the $CH_2$ position of that same molecule. For example, FIG. 40 is a graph illustrating the temperature dependence of such a migration in the equilibration reaction: $^{12}CH_2D-{}^{12}CH_2-{}^{12}CH_3 \leftrightarrow {}^{12}CH_3-{}^{12}CHD-{}^{12}CH_3$. As can be seen in FIG. 40, D enrichment at the C2 position of propane decreases as the temperature increases. Such an effect can be standardized by comparison of two standards (or reference materials) that differ from one another by a known (or preset) amount in the concentrations of an isotope of interest in the two sites being investigated. For example, hydrogen isotope exchange between the two sites ('1' and '2') of a propane molecule through hydrogen migration can be calibrated according to the equation:

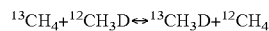

$$([D]_1/[D]_2)_{Measured} = ([D]_1/[D]_2)_{known} \times K_{migration}$$

Figure 41:
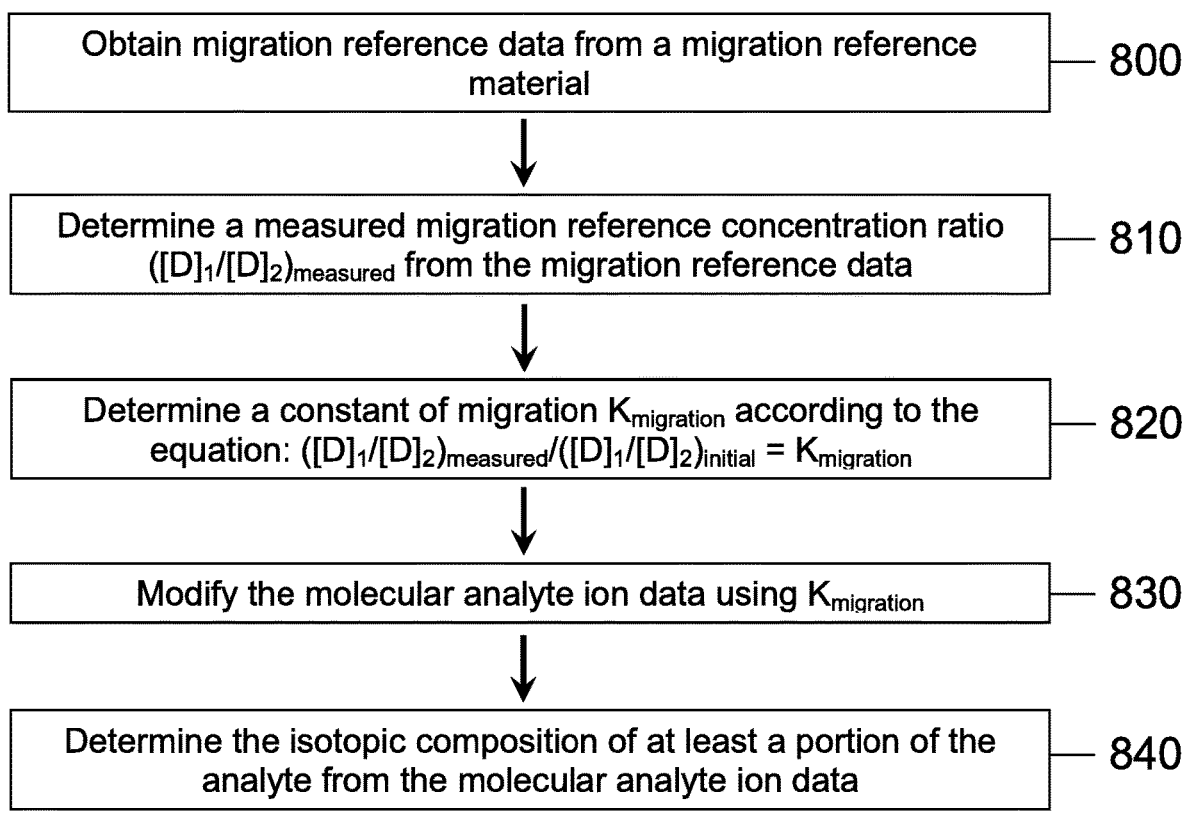
FIG. 41 is a flowchart showing a component of a method for determining the isotopic composition of an analyte in a sample according to an embodiment of the invention.

As shown in FIG. 41, according to embodiments of the invention the method can include (800) obtaining migration reference data from a migration reference material including isotopomers having an initial migration reference concentration ratio $([D]_1/[D]_2)_{initial}$. The migration reference data can be obtained by analyzing the migration reference material according to the methods described above with respect to the analyte. The method also includes (810) determining a measured migration reference concentration ratio $([D]_1/[D]_2)_{measured}$ from the migration reference data. The method further includes (820) determining a constant of migration $K_{migration}$ according to the Equation:

$$([D]_1/[D]_2)_{measured}/([D]_1/[D]_2)_{initial} = K_{migration}$$

The molecular analyte ion data can be modified using the constant of proportionality $K_{migration}$ (830). The isotopic composition of at least a portion of the analyte can then be determined from the modified molecular analyte ion data (840).

The above-described reference materials (e.g., the mass discrimination reference material, the first linearity reference material, the second linearity reference material, the first recombination reference material, the second recombination reference material, and the migration reference material) may each be any suitable material (e.g., any suitable compound) and they may each have a composition that is the same or different as that of the other reference materials or the analyte.

Standardization

In some embodiments, standardization of any or all of the above-described phenomena for unknown samples (e.g., unknown analytes) is independently or concurrently accomplished through "sample-standard bracketing," as described above, such as sequential analysis of a standard (e.g., a reference material), a sample of unknown composition, and a standard (e.g., another reference material that is the same as or different from the first reference material). For example, reference data can be first be obtained by analyzing a reference material according to the methods described above with respect to the analyte. Next analyte data can be obtained by analyzing an analyte data according to the methods described above. Then, additional reference data can be obtained by analyzing a reference material (which can be the same as or different from the reference material above) according to the methods described above with respect to the analyte. After the reference data, analyte data and additional reference data has been obtained, linear interpolation of the values measured for at least one or more of the constants $\square_{IMF}$, L, $K_{fragment}$, $K_{adduct}$, $K_{redistribute}$, or $K_{migration}$ (determined from the reference data and additional reference data according to the methods described above) for the bracketing standards to determine the values of the constants that should be applied to the unknown sample.

Figure 42:
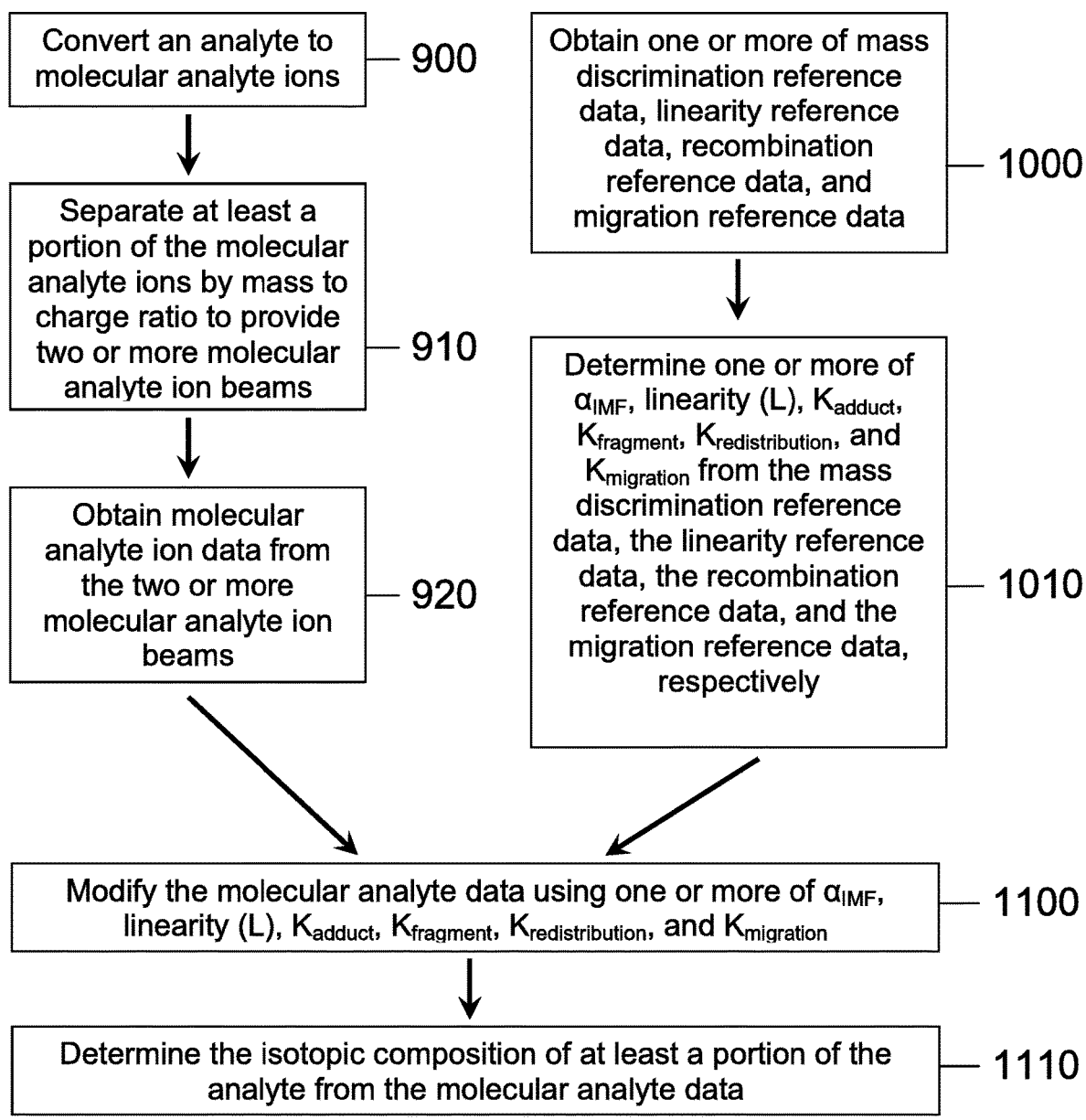
FIG. 42 is a flowchart showing a method for determining the isotopic composition of an analyte in a sample according to an embodiment of the invention.

For example, as shown in FIG. 42, the method according to embodiments of the invention can include (900) converting the analyte to molecular analyte ions using an ion source in a second mass spectrometer. The method also includes (910) separating at least a portion of the molecular analyte ions by mass to charge ratio to provide two or more molecular analyte ion beams. The method further includes (920) obtaining molecular analyte ion data from the two or more molecular analyte ion beams. The molecular analyte ion data can be obtained according to the methods described above. The method also further includes (1000) obtaining one or more of mass discrimination reference data, linearity reference data, recombination reference data, and migration reference data, and (1010) determining one or more of a linearity (L), a constant of proportionality $\alpha_{IMF}$, a constant of proportionality $K_{adduct}$, a constant of proportionality $K_{fragment}$, a constant of proportionality $K_{redistribution}$, and a constant of migration $K_{migration}$, which can be determined according to the methods described above. The method further includes modifying the molecular analyte ion data using one or more of $\alpha_{IMF}$, L, $K_{adduct}$, $K_{fragment}$, $K_{redistribution}$, and $K_{migration}$ (1100). The isotopic composition of at least a portion of the analyte can then be determined from the modified molecular analyte ion data (1110).

The number and frequency of the above-described bracketing measurements can vary with instrument conditions, analyte type and desired accuracy and precision. Based on prior experience with broadly similar instrumentation and measurements, $\rfloor_{IMF}$ can be calibrated on time scales of tens of seconds (e.g., using the dual inlet changeover valve or multiple-injection carrier gas methods common to existing gas source isotope ratio mass spectrometers), values of $K_{fragment}$ and $K_{adduct}$ will be relatively constant over periods of hours to days, and values of L and $K_{redistribute}$ will be constant over periods of days to weeks. There is insufficient prior evidence to predict the variability of $K_{migration}$. The design purpose of having 4 gas reservoirs, each with its own capillary bleed, in the sample introduction system 20 (e.g., the inlet system) is to facilitate convenient comparison of an unknown sample (e.g., a sample including an analyte such as a gas or volatile organic compound introduced through a helium carrier gas) with multiple standards of known isotopic composition.

Statistical Determinations of Isotope Distributions

The methods described above are capable of determining the abundance ratios of isotopologues of molecular species and their derivatives (e.g., fragments thereof, adducts thereof, etc.). However, additional calculations can be used to establish positions of isotopes within these molecular species based on comparisons of respective isotopic compositions of a molecule and one or more of its fragments, or two or more of its fragments. This can be achieved through a combination of principles of sampling statistics with standardization of relevant analytical constants (e.g., $\square_{IMF}$, L, $K_{fragment}$, $K_{adduct}$, $K_{redistribute}$, $K_{migration}$), as described above.

For example, propane ($C_3H_8$) contains two non-equivalent carbon positions: a central ($CH_2$) position (hereafter, position 'A') and two symmetrically equivalent terminal methyl ($CH_3$) positions (hereafter position 'M'). The difference in $^{13}C$ concentration between these two positions can be determined by comparison of the abundance ratios: $[^{13}C^{12}C_2H_8]$ and $[^{13}CH^{12}CH_5]/[^{12}C_2H_5]$, through simultaneous solution of the following family of equations (i.e., equations 1 through 4):

$$[^{13}C^{12}C_2H_8]/[^{12}C_3H_8] = (2[^{13}C]_M[^{12}C]_M[^{12}C]_A + [^{13}C]_A[12C]_M^2)/([^{12}C]_M^2[^{12}C]_A) \quad (1)$$

$$[^{13}C^{12}CH_5]/[^{12}C_2H_5] = ([^{13}C]_M[^{12}C]_A + [^{13}C]_A[12C]_M)/([^{12}C]_M[^{12}C]_A) \quad (2)$$

$$[^{13}C]_M + [^{12}C]_M = 1 \quad (3)$$

$$[^{13}C]_A + [^{12}C]_A = 1 \quad (4)$$

In equations 1 and 2, $[^{13}C]_M$, $[^{13}C]_A$, $[^{12}C]_M$ and $[^{12}C]_A$ refer to the $^{13}C$ and $^{12}C$ concentrations of the methyl (M) and alkyl (A) molecular sites.

Two additional expressions must hold true to account for the full isotopic inventory of both methyl and alkyl sites (i.e., $[^{13}C]_M$, $[^{13}C]_A$, $[12C]_M$, and $[^{12}C]_A$ must satisfy equations 3 and 4).

There are four unknowns ($[^{13}C]_M$, $[^{13}C]_A$, $[^{12}C]_M$ and $[^{12}C]_A$) in the above family of four equations. Thus, one can uniquely solve this family of equations, assuming that $[^{13}C^{12}C_2H_8]/[^{12}C_3H_8]$ and $[^{13}C^{12}CH_5]/[^{12}C_2H_5]$ have been correctly determined through mass spectrometric measurements of the relevant ion ratios (i.e., standardized to determine the relevant analytical constants) and assuming that the $C_2H_5$ fragment derives from the loss of one methyl group of the parent molecule (this last assumption is consistent with prior study of the fragmentation physics of propane, and can be verified on one embodiment of the second mass spectrometer of the present invention through analyses of standards that have been highly enriched in $^{13}C$ in the central and terminal carbon positions). Thus, it is straightforward to convert two measurable ratios of molecular or fragment ions into fully constrained determinations of the proportions of $^{13}C$ contained in two structurally distinct molecular sites. Similar reasoning can be applied to a large number of other instances in which isotopic contents of positions in organic and other molecular structures can be reconstructed from the analysis of molecular and fragment ions.

Ion Correction of Non-Resolved Isobaric Interferences

Some molecular and fragment ion species may be difficult to resolve from nearby isobaric interferences, either due to the high total mass of the species in question or because the species is so low in abundance that it is preferable to perform mass spectrometric analysis with a large entrance slit and correspondingly high transmission but poor mass resolution. In such cases, abundances of unresolved species of interest may be determined by correction based on independent constraints on the proportions of all species contributing to a composite ion peak. $^{12}CH_3D$ methane serves as an illustrative example. The abundance of $^{12}CH_3D$ could be determined without direct mass resolved analysis if one measured the ion intensity ratio: $(I_{13CH4} + I_{12CH3D} + I_{12CH5})/I_{12CH4}$ and subtracted contributions from the two interfering species ($^{13}CH_4$ and $^{12}CH_5$) by separately measuring $^{13}CH_4/^{12}CH_4$ (a relatively easily measured ratio at moderate mass resolution) and $K_{adduct}$ (which can be determined through analyses of standard gases or reference materials, as described above).

EXAMPLES

Three examples of uses of the apparatus and methods according to embodiments of the invention follow. The examples are supported with data generated on a second mass spectrometer according to one embodiment of the invention. The second mass spectrometer used in the examples demonstrated a mass resolution (e.g., resolving power) up to 25,500 using the above described 5%-95% definition of mass resolution. Table 1 shows a comparison of the sensitivity and resolving power (e.g., mass resolution) of a second mass spectrometer according to exemplary embodiments of the invention to a conventional MAT-253 mass spectrometer available from Thermo Fisher Scientific, Inc.

TABLE 1

| | Entrance slit (µm) | Molecules/ion | Resolving Power (5%/95%) |
|---|---|---|---|
| Conventional MAT-253 | 500 | 600 | ~500 |
| Example 1 | 250 | ~1,500 | 1,500-2,000 |
| | 50 | ~7,500 | 7,500-10,000 |
| | 25 | ~15,000 | 10,000-12,000 |

TABLE 1-continued

| Entrance slit (μm) | Molecules/ion | Resolving Power (5%/95%) |
|---|---|---|
| 15 | ~20,000 | 12,000-15,000 |
| 5 | ~60,000 | 20,000-25,000 |

As can be seen in Table 1, the second mass spectrometer according to embodiments of the invention exhibit significantly higher resolving power, but reduced sensitivity as compared to the conventional MAT-253 mass spectrometer available from Thermo Fisher Scientific, Inc. However, most stable isotope ratio measurements are made at ion currents >$10^9$ CPS and, therefore, the relatively lower sensitivity of embodiments of the invention is acceptable, as one can sacrifice a lot of signal and still obtain a precise measurement.

The second mass spectrometer according to embodiments of the invention also demonstrated flat plateaus on hydrocarbon "ziggurat" peaks (e.g., peaks having the shape of a truncated pyramid, such as a pyramid having a flat top) as shown in the mass spectrum of FIG. 33E. The second mass spectrometer according to embodiments of the invention has also demonstrated ~0.1% precision on faraday cup/electron multiplier ratio measurements. The second mass spectrometer according to embodiments of the invention is noteworthy for its flexibility, mass range, ease of use for complex spectra, and it has significantly improved resolving power relative to ICP-MS instruments, which could be the result of: the stability of the Nier-type electron impact (EI) source, the narrow energy distribution of the source, and the improved vacuum in embodiments of the invention.

The apparatus, systems and methods according to embodiments of the invention described herein can be used in various applications. For example, according to embodiments of the invention, a method of identifying a high-potential oil-field includes analyzing an analyte of a sample from a target field using an embodiment of the second mass spectrometer and/or methods described herein to obtain relative proportions of isotopologues in one or more samples, such as methane, ethane or propane. The relative proportions of the isotopologues can be used to calculate equilibrium constants for isotope exchange reactions among the isotopologues (such as the reaction among methane isotopologues described below). Temperatures of gas formation or storage can be inferred by comparing these calculated equilibrium constants to the temperature-dependent values calibrated by theory or experiment. These temperatures can then be compared with known geothermal gradients to infer the depths in the earth of hydrocarbon generation and/or storage, which can then be used to guide drilling for oil and gas exploration.

Example 1

Methane Thermometry

As described above, the temperature of origin of methane or other hydrocarbons is useful for natural gas exploration and study of the environmental chemistry of methane. For example, the temperature of origin of methane constrains the depths and mechanisms of the source rocks from which the methane was obtained, and the temperature of storage informs exploration of the reservoirs where the methane is trapped. The temperatures of equilibration of molecules such as methane can be recorded by the proportions of their rare, heavy isotopes (e.g. $^{13}C$ and D) that form multiply substituted isotopologues (e.g., $^{13}CH_3D$) rather than singly substituted isotopologues (e.g., $^{13}CH_4$ and $^{12}CH_3D$). The proportions of the rare, heavy isotopes of methane are related through exchange reactions, such as:

$$^{12}CH_3D + {}^{13}CH_4 \leftrightarrow {}^{13}CH_3D + {}^{12}CH_4$$

The equilibrium constants for the exchange reactions of methane, such as the one shown above, are a function of temperature, and thus measurements of relative proportions of the four isotopologues involved in the reaction above provides a method of geochemical thermometry (e.g., a method of determining the temperature of origin and/or storage of a sample of methane). Such methods of thermometry have been previously determined for $CO_2$ and carbonate, and the principles of thermodynamics that explain this phenomenon are well known of $H_2$, $O_2$, $N_2$, $CO$, $N_2O$ and a variety of other simple molecular compounds. Similar principles apply to the isotopic abundances of multiply substituted isotopologues of ethane (e.g., $^{13}C_2H_6$) and higher order hydrocarbons.

Figure 43:
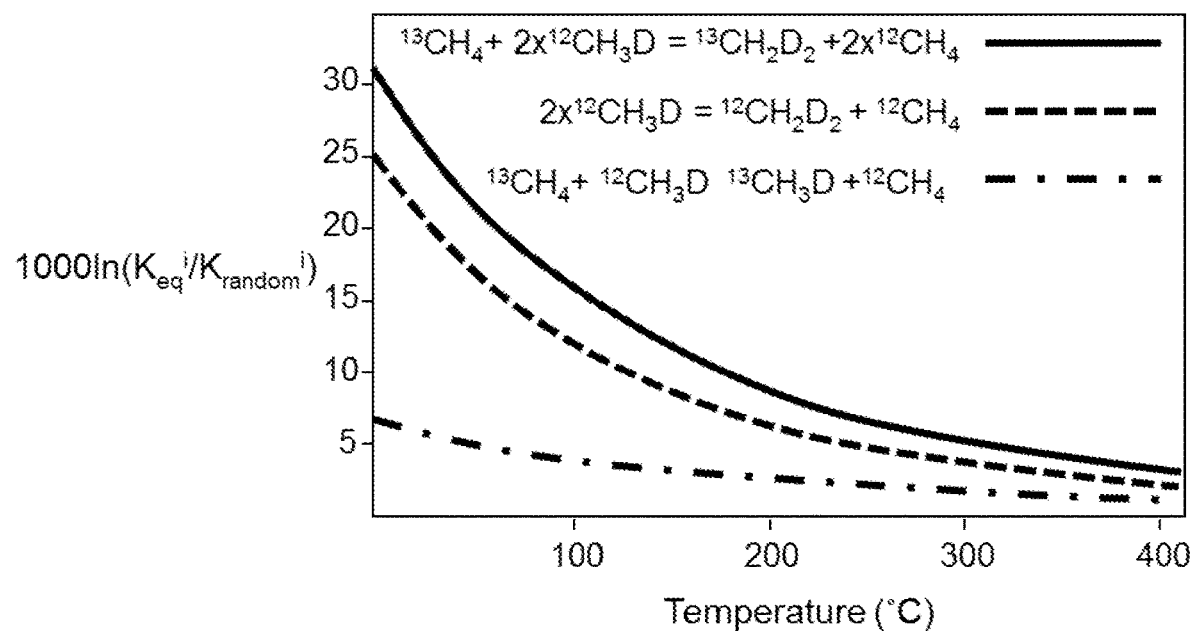
FIG. 43 is a graph illustrating predicted equilibrium constants for isotope exchange reactions involving homogeneous equilibria of methane isotopologues, including multiply substituted isotopologues.

The principles of statistical thermodynamics and the spectroscopy of methane indicate that the equilibrium constant for the above exchange reaction is ~1.005 at 300 K and decreases toward 1 roughly linearly with decreasing value of the quantity ($1/T^2$), as shown in FIG. 43. FIG. 43 includes predicted equilibrium constants for isotope exchange reactions involving homogeneous equilibria of methane isotopologues, including multiply substituted isotopologues. The calculations were based on density functional theory predictions of the vibrational dynamics of methane and its isotopologues and quantum mechanical models of the relevant partition functions. Calculated equilibrium constants were normalized by the value for a random distribution of isotopes among all isotopologues and plotted as per mil (‰) deviations from that random distribution. A sufficiently precise and accurate measurement of the relative abundances of the four isotopologues of methane appearing in the above equation should permit one to determine the temperature of formation of methane. Similar principles lead to predictions regarding a large number of similar homogeneous isotope exchange equilibria among isotopologues of alkanes and other organic and inorganic molecules.

Table 2 below provides the precise masses and expected abundances of the four relevant isotopologues of methane for a sample equilibrated at 300 K and in which 1% of its carbon atoms are $^{13}C$ and 0.015% of its hydrogen atoms are D (i.e., approximately the natural isotopic abundances). The third and fourth columns of Table 2 list the expected (or predicted) ion currents, in both amps and counts per second, for all analyzed species at the detector, assuming an ion source with performance characteristics similar to commercial Nier-type electron impact sources (having typical ionization efficiencies), a gas pressure in the source similar to the operating conditions of common stable isotope ratio mass spectrometers (e.g., ~$10^{-7}$ mbar), and 1% transmission (e.g., a reduction in transmission of a factor of 100, corresponding to the transmission loss associated with use of the smallest source aperture to achieve high mass resolution). A usefully precise temperature estimate requires that the smallest of these ion intensities be measured with precision of ~0.01%.

TABLE 2

| Species | Mass (AMU) | Concentration | Ion current (amps) | Counts per second# |
|---|---|---|---|---|
| $^{12}CH_3D$ | 17.0376 | 5.94E−04 | 1.80E−12 | 1.13E+07 |
| $^{13}CH_4$ | 17.0347 | 9.99E−03 | 3.03E−11 | 1.89E+08 |
| $^{13}CH_3D$ | 18.0409 | 6.00E−06 | 1.82E−14 | 1.14E+05 |
| $^{12}CH_4$ | 16.0313 | 9.89E−01 | 3.00E−09 | 1.88E+10 |

Values in excess of $10^6$ are too high for analysis by electron multiplier; these ion beams are analyzed by faraday cup collection.

Figure 44A:
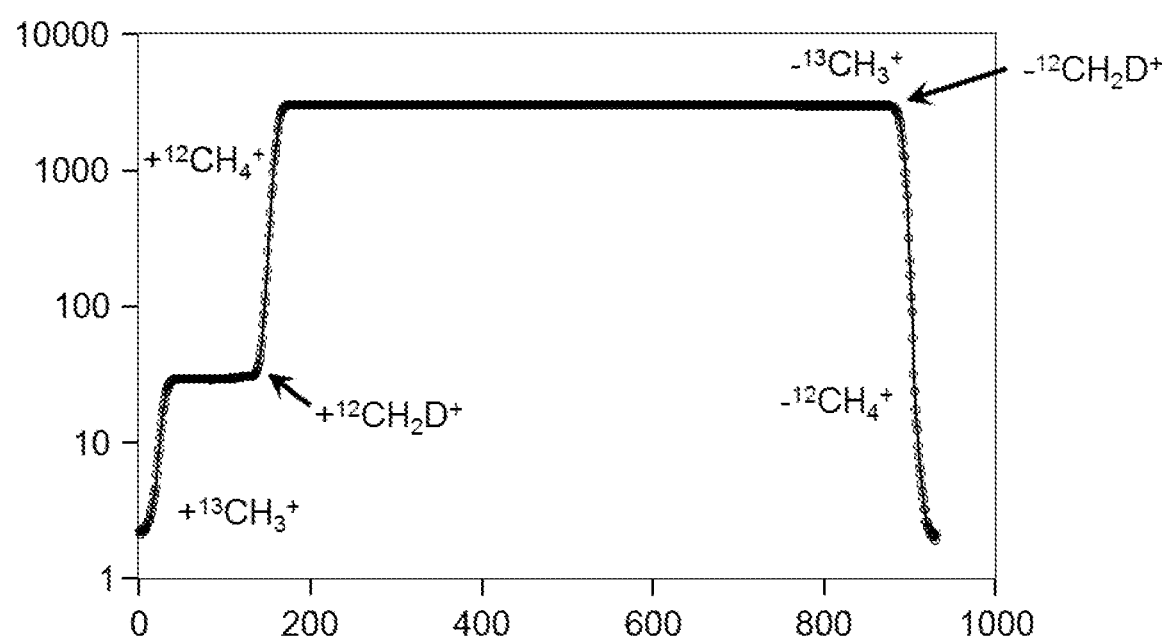
FIG. 44A is a graph illustrating the peak shape generated by scanning the mass 16 AMU analyte ion beam of methane across a single detector according to an embodiment of the invention.

As can be seen in FIG. 44A, which shows a mass spectrum (logarithmic scale) acquired for methane, the second mass spectrometer according to an embodiment of the invention is capable of mass-resolving two representative isotopologues relevant to this measurement ($^{12}CH_4$ from the ion fragment, $^{13}CH_3$; it is not visually obvious, but both species are also discriminated from the minor beam of $^{12}CH_2D$ in this spectrum). The peak shape shown in FIG. 44A was generated by scanning the mass 16 AMU ion beam of methane across a single detector, using a second mass spectrometer according to one embodiment of the invention. The locations at which the $^{13}CH_3^+$, $^{12}CH_2D^+$ and $^{12}CH_4^+$ ion beams enter and then exit the detector are shown in the mass spectrum of FIG. 44A.

Figure 44B:
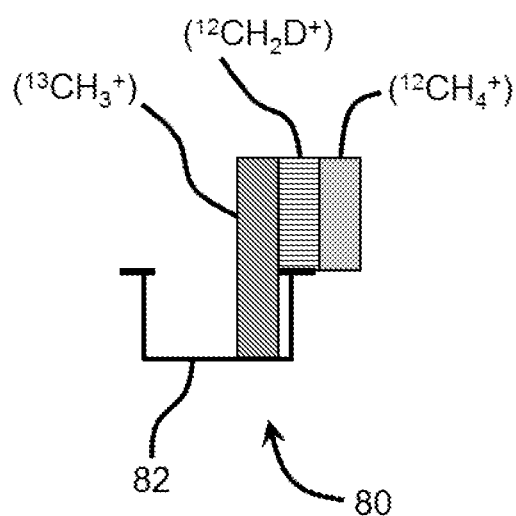
FIGS. 44B-G are partial schematic views showing three molecular ion beams derived from methane being scanned across a single detector.
Figure 44C:
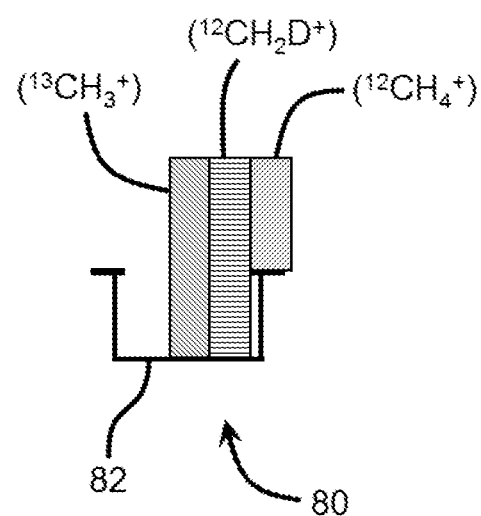
Figure 44D:
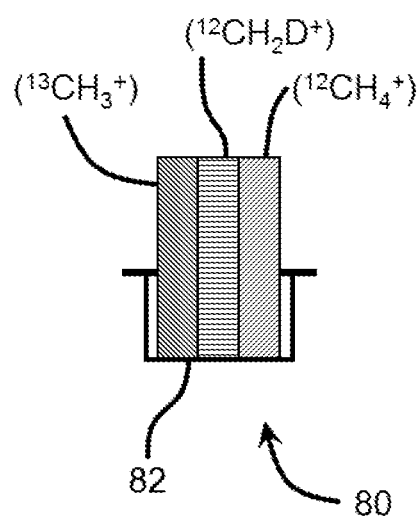
Figure 44E:
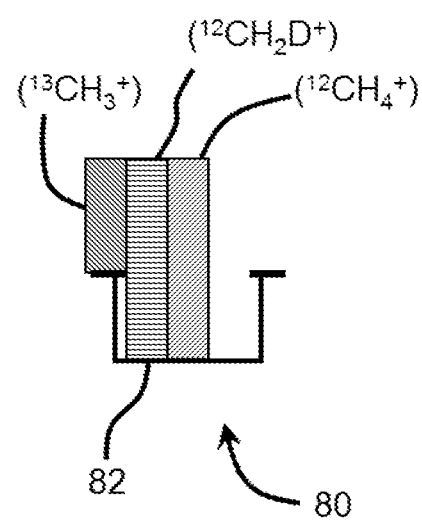
Figure 44F:
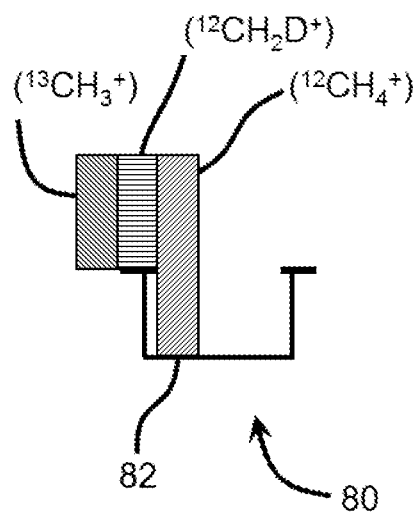
Figure 44G:
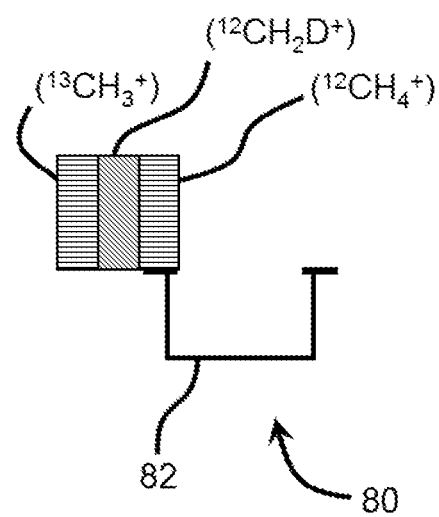

Additionally, FIGS. 44B-G show the $^{13}CH_3^+$, $^{12}CH_2D^+$ and $^{12}CH_4^+$ ion beams entering and then exiting a single detector 82 of a detector array 80. For example, FIG. 44B shows the $^{13}CH_3^+$ ion beam entering the detector. FIG. 44C shows the $^{12}CH_2D^+$ ion beam entering the detector such that both the $^{13}CH_3^+$ and $^{12}CH_2D^+$ ion beams are detected in the single detector concurrently (or simultaneously). Next, FIG. 44D shows the $^{12}CH_4^+$ ion beam entering the detector such that all three of the $^{13}CH_3^+$, $^{12}CH_2D^+$ and $^{12}CH_4^+$ ion beams are detected in the single detector concurrently (or simultaneously). FIG. 44E shows the $^{13}CH_3^+$ ion beam exiting the detector such that the $^{12}CH_2D^+$ and $^{12}CH_4^+$ ion beams are detected in the single detector concurrently (or simultaneously). FIG. 44F shows the $^{12}CH_2D^+$ ion beam exiting the detector such that only the $^{12}CH_4^+$ ion beam is detected in the detector. FIG. 44G shows the $^{12}CH_4^+$ ion beam exiting the detector.

The mass resolution of the peak scan shown in FIG. 44A is about 25,500 (using the 5%-95% definition described above). As can be seen in FIG. 44A, the second mass spectrometer according one embodiment of the invention is capable of resolving $^{13}CH_3$ from $^{12}CH_4$. While it is not immediately clear in FIG. 44A, the minor ion beam $^{12}CH_2D$ is also well-resolved from $^{13}CH_3$ from $^{12}CH_4$. Similar performance is expected for diverse ions of methane, its fragments and adducts having other mass/charge ratios.

Figure 45:
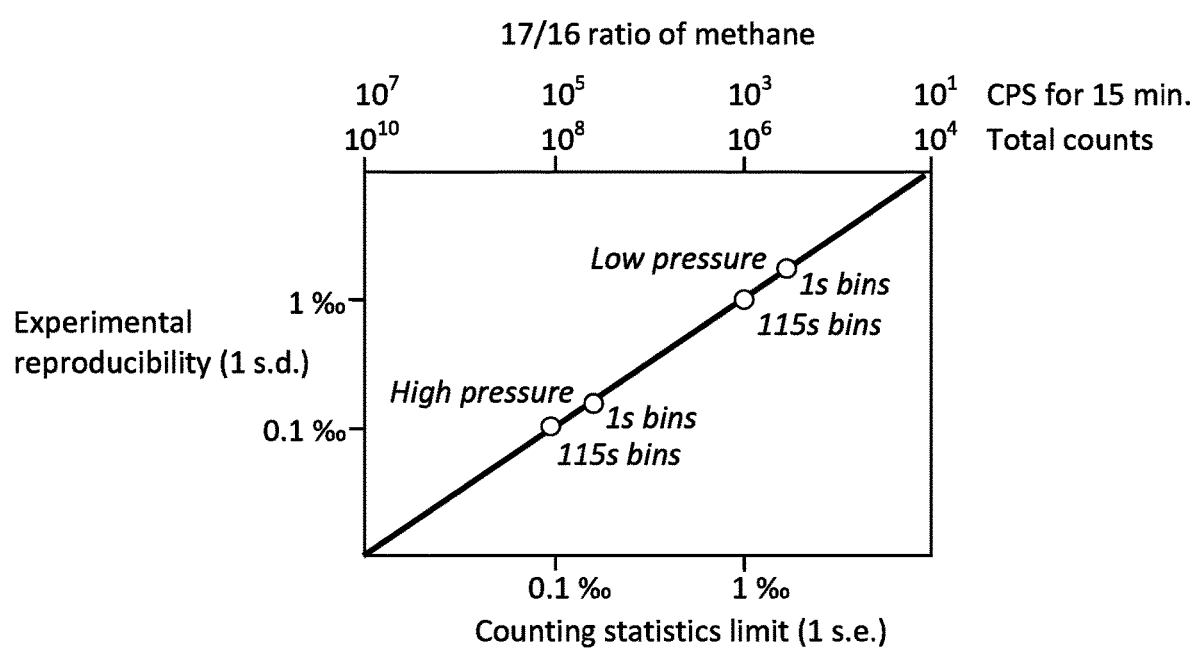
FIG. 45 is a graph illustrating the external precisions of replicate analyses of the mass 17/16 ratio of methane gas according to one embodiment of the invention.

FIG. 45 demonstrates the external precision that can be achieved through sample/standard bracketing in measurements of the ratio: ($^{13}CH_4+^{12}CH_3D+^{12}CH_5$)/$^{12}CH_4$ (i.e., the mass 17/16 ratio) for methane. These measurements were taken using a second mass spectrometer according to one embodiment of the invention. Each point represents the standard deviation (1 s) of measured ratios, where each measurement is the average over a 1 second or 115 second integration. Measurements were made at two different source pressures, to vary the counting rate. All measurements were made using electron multiplier detectors. The horizontal axis is the predicted standard error of each such measurement, based on counting statistics. As can be seen in FIG. 45, the above-described ratio was measured with external precision as good as 0.01 percent, relative, over a wide range of current integration times and signal intensities, indicating that the second mass spectrometer according to an embodiment of the invention is capable of measuring ion intensity ratios with precision sufficient for the example applications described herein.

The mass resolutions and the precision of the above-described isotope ratio measurements are sufficient such that embodiments of the invention can be used to calibrate values of $\square_{IMF}$ and L for the two isotope ratios measured (e.g., [$^{13}CH_3D$]/[$^{12}CH_3D$] and [$^{12}CH_4$]/[$^{13}CH_4$]) and for $K_{redistribution}$ for methane in the ion source. Three standards (e.g., reference materials) having distinct, known (or preset) isotopic compositions can be used to calibrate all three of these analytical constants prior to analysis of an unknown sample (e.g., a sample containing methane as an analyte having unknown isotopic composition). This standardization can be accomplished using embodiments of the invention through the repeated sequential analysis of three standards (e.g., reference materials) and one sample of unknown composition (e.g., an analyte having unknown isotopic composition), by alternately measuring the gas streams emanating from four flexible bellows of the inlet system of the second mass spectrometer. $K_{fragmentation}$ and $K_{migration}$ are not relevant to any of the species analyzed for the above-described analysis of methane; if required to make measurements for analogous applications to molecules more complex than methane, $K_{fragmentation}$ and $K_{migration}$ can be calibrated through study of additional standards.

Measurements similar to those above may also be useful for carbon dioxide ($CO_2$), which has 18 naturally occurring isotopologues ($^{12}C^{16}O_2$, $^{12}C^{18}O_2$, $^{14}C^{18}O^{17}O$, etc.), each of which is unique in its physical and chemical properties and thus constitutes a potential independent tracer of source, reaction mechanism and/or environment of origin. Other methods of mass spectrometric or spectroscopic analysis of $CO_2$ isotopologues are capable of determining relative abundances of only 5 of these species ($^{12}C^{16}O_2$, $^{13}C^{16}O_2$, $^{14}C^{16}O_2$, $^{12}C^{18}O^{16}O$, and $^{12}C^{17}O^{16}O$). Any information encoded in the proportions of the other remaining 13 species is effectively lost by those other measurements.

Example 2

Position-Specific Isotope Composition of n-Alkanes

Another embodiment is directed to the determination of relative abundances of $^{13}C$-bearing isotopologues of the $CH_3^+$ and $C_2H_5^+$ ion fragments generated by ionization of propane. The foregoing data, combined with characterizations of the empirical constants describing fragmentation and recombination reactions in the ion source, can be used to determine the difference in $^{13}C$ content between the terminal and central carbon positions of propane. This difference is predicted to be a function of temperature in thermodynamically equilibrated propane (and thus can be used to establish the temperature of formation, as for the methane analysis described above). In non-equilibrated gases, this difference may illuminate the chemical kinetic mechanisms of natural gas maturation, and thus also aid in the exploration and development of oil and gas deposits.

Naturally occurring n-alkanes (e.g., methane, ethane, propane, etc.) are products of diverse processes, such as thermal degradation of organic matter, hydrothermal reactions of aqueous solutions, and biosynthesis; many are also products of industrial chemical synthesis. The carbon and hydrogen isotope content of the n-alkanes is a function of both the carbon sources from which they were synthesized and the conditions and chemical mechanisms of their synthesis.

Thus, forensic identification and source attribution of organic molecules may be achieved based on the isotopic fingerprints of the organic molecules, including but not restricted to the carbon and hydrogen isotope compositions of n-alkanes. Measurements made with embodiments of the invention include several novel constraints to the isotopic fingerprint of alkanes and thereby facilitate determination of the sources of the alkanes. In embodiments of the invention, some of the novel measurements include: determination of the $^{13}C/^{12}C$ ratios of non-equivalent sites in alkane structures, determination of the D/H ratios of non-equivalent sites in alkane structures, determination of the abundance of $^{13}C$-$^{13}C$ bonds (i.e., $^{13}C$ substitutions in two adjacent sites of the same molecule), and determination of the abundance of $^{13}C$-D bonds in methyl groups from the terminal positions of chain alkane structures (i.e., $^{13}C$ substitutions immediately adjacent to a D substitution for H in the same methyl group).

Determination of the $^{13}C/^{12}C$ ratios of non-equivalent sites in alkane structures can be accomplished by determining the $^{13}C/^{12}C$ ratios of intact molecular analyte ions and of analyte fragment ions, and combining these data using mathematical expressions such as those described above (e.g., statistical determinations of isotope distributions). This approach is applicable to n-alkanes containing 3 or more carbons (i.e., propane and higher order hydrocarbons), and generally requires determination of one independent carbon isotope ratio (i.e., the $^{13}C/^{12}C$ ratio of one analyte molecule or molecular analyte fragment) per non-equivalent carbon site.

Determination of the D/H ratios of non-equivalent sites in alkane structures can be accomplished by determining the D/H ratios of intact molecular analyte ions and of analyte fragment ions, and combining these data using mathematical expressions similar to those described above (e.g., statistical determinations of isotope distributions). This approach is applicable to n-alkanes containing 3 or more carbons (i.e., propane and higher order hydrocarbons), and generally requires determination of one independent hydrogen isotope ratio (i.e., the D/H ratio of one analyte molecule or molecular analyte fragment) per non-equivalent carbon site. Such measurements likely will require calibration of $K_{migration}$ analytical constants for some compounds and analytical conditions.

Determination of the abundance of $^{13}C$-$^{13}C$ bonds (i.e., $^{13}C$ substitutions in two adjacent sites of the same molecule) can be accomplished through principles similar to those described above (e.g., statistical determinations of isotope distributions), but can be constrained by measurements of abundances of doubly-substituted molecular analyte ions (e.g., $^{13}C_2^{12}CH_8$ propane) and their analyte fragments (e.g., $^{13}C_2H_5$ derived from the fragmentation of propane). Such measurements are possible for any species containing two or more adjacent carbon atoms (i.e., ethane and larger n-alkanes).

Determination of the abundance of $^{13}C$-D bonds in methyl groups from the terminal positions of chain alkane structures (i.e., $^{13}C$ substitutions immediately adjacent to a D substitution for H in the same methyl group) can be accomplished through analysis of the $^{13}CH_2D/^{12}CH_3$ ratio of analyte methyl fragment ions (a minor but common species generated by electron impact ionization of alkanes).

The largest molecular analyte or analyte fragment ion mass that can be subjected to these measurements will vary as a function of analytical conditions (e.g., source water pressure, total pressure and tuning conditions), the level of precision desired, the strategy employed in ion collection (e.g., multi-collection or peak scanning), and the method of data processing (e.g., ion correction of non-resolved isobaric interferences). In some instances, the isotopic composition of the full analyte molecule can be easily and precisely determined using previously existing methods, and additional constraints from measurements of analyte fragment ions can be added according to embodiments of the present invention. Table 3 shows anticipated signal strengths for multiply substituted alkanes for a modest source pressure and an entrance slit having a width of about 5 μm.

TABLE 3

| Isotopes | abundance | count rate | time to 0.3% |
|---|---|---|---|
| 1 × $^{13}C$ | 6 · 10$^{-2}$ | 3 pA | 1 s |
| 2 × $^{13}C$ | 4 · 10$^{-3}$ | 1 · 10$^6$ cps | 9 s |
| 3 × $^{13}C$ | 2 · 10$^{-4}$ | 5 · 10$^4$ cps | 200 s |
| 1 × $^{13}C$; 1 × D | 1 · 10$^{-4}$ | 4 · 10$^4$ cps | 230 s |

Embodiments of the present invention provide an increased number of compositional dimensions that can be investigated, which provides the opportunity to dramatically improve the specificity of "finger printing." For example, conventional analysis of n-alkanes yields two isotope ratios: $^{13}C/^{12}C$ and D/H. However, a comprehensive analysis according to embodiments of the present invention would yield: 10 ratios for methane, 128 ratios for ethane, 512 ratios for propane, ~4,000 ratios for n-butane, ~32,000 ratios for n-pentane, and ~10$^8$ ratios for n-octane.

Example 3

Isotopic Anatomy of Glucose

Yet another embodiment of the invention is directed to the analysis of the proportions of $^{13}C$, D and/or $^{18}O$ bearing isotopologues of ion fragments generated by delivering volatile organic compounds, such as derivatized sugars, into the ion source. The foregoing data, combined with characterizations of the empirical constants describing fragmentation and recombination reactions in the ion source, will allow for the characterization of isotopic fingerprints associated with diverse sources of such compounds and thus aid in the forensic studies of diverse organic compounds (functionally, any species that can be derivatized to create a compound that can be delivered to the ion source through a heated gas chromatographic column).

For example, a method for the diagnosis or treatment of a disease includes analyzing an analyte of a sample from a patient using an embodiment of the second mass spectrometer and/or methods described herein to obtain the isotopic composition of at least a portion of the analyte. The method also includes comparing the isotopic composition obtained for the analyte to a database of isotopic compositions. The correlation between the isotopic composition obtained for the analyte and the database of the isotopic compositions can be used to determine a disease diagnosis or disease treatment protocol.

In another embodiment of the invention, a method of analyzing a drug or drug metabolite includes analyzing the drug or drug metabolite in a sample using an embodiment of the second mass spectrometer and/or methods described herein to obtain the isotopic composition of at least a portion of the drug or drug metabolite. The method further includes comparing the isotopic composition obtained for the drug or drug metabolite to a database of isotopic compositions. The correlation between the isotopic composition obtained for the drug or drug metabolite and the database of isotopic compositions can be used to determine a property of the drug or the drug metabolite and is useful in the forensic study of diverse organic compounds.

Metabolic consumption of glucose in living organisms is characterized by isotopic fractionation of the residual glucose pool (e.g., change in isotopic composition of blood glucose as a function of the fraction consumed). Though many of the details of this fractionation are unknown, the principles of chemical physics relevant to chemical separation of isotopes indicate these effects can differ significantly with the conditions of glucose consumption (e.g., temperature) and the mechanism of consumption, possibly including subtle variations in the structures of relevant enzymes and other reactive sites. Thus, characterization of the isotopic anatomy of glucose could serve as a diagnostic tool for characterizing the function of metabolic processes relevant to diabetes and possibly other diseases. Accordingly, aspects of embodiments of the invention are directed toward determining the isotopic signatures of metabolites, including but not limited to the carbon, oxygen and hydrogen isotope compositions of components of the glucose molecule. Similar principles apply to other examples of biomolecules that are subject to metabolic consumption.

Glucose and its derivatives can be transmitted through a gas chromatograph and thus are suitable analytes for embodiments of the present invention. Glucose itself has slow transport times through conventional gas chromatograph columns, suggesting that, in some embodiments, the analysis might be better made on a faster-moving glucose derivative (e.g., a glucose derivative that elutes from a gas chromatograph column faster than glucose). On the other hand, components added to glucose derivatives can contribute substantially to some portions of the mass spectrum, which can complicate interpretation of the isotopic measurements of glucose derivatives. Nonetheless, those of ordinary skill in the art can properly select glucose derivatives that provide suitable measurement characteristics. Regardless, both options (direct analysis of glucose or analysis of a glucose derivative) yield analyzable products on electron impact ionization and so are suitable for analysis according to embodiments of the present invention.

The fragmentation spectrum of glucose under electron impact ionization includes more than 75 analyzable peaks in a conventional, low-resolution mass spectrum; each of these peaks is the result of several analyte ion beams corresponding to species that have the same cardinal mass (e.g., $^{13}C$ and $^{12}CH$, at mass 13 AMU, etc.). Many of these composite peaks occur below mass 60 AMU, and thus should contain one or more component analyte ion beams that can be uniquely mass resolved by the mass spectrometric analyzer according to embodiments of the invention, assuming a mass resolution of 20,000 or more. Others of these ion beams may be more difficult to mass resolve, but are possibly analyzable using methods such as peak scanning and ion correction of non-resolved isobaric interferences, as described above.

Take for example, the analyte ion beams of the glucose mass spectrum including analyte ions having respective masses of 28, 29 and 30 AMU; the corresponding portions of the glucose mass spectrum include large contributions from CO and its hydrogen adducts (e.g., $^{12}C^{16}O$ at mass 28 AMU, $^{12}CO^{16}H$, $^{13}C^{16}O$ and $^{12}C^{17}O$ at 29 AMU, and $^{12}C^{16}OH_2$, $^{13}C^{16}OH$, $^{12}C^{16}OD$, $^{12}C_{18}O$ and $^{13}C^{17}O$ at mass 30). The hydrogen bearing species of CO are easily mass resolvable from the non-hydrogen bearing species, whereas isobaric interferences among the isotopologues of the CO molecule are not easily mass resolvable. Thus, in some embodiments, one can measure the ratios: $([^{13}C^{16}O]+{}^{12}C^{17}O])/[^{12}C^{16}O]$ and $(^{12}C^{18}O+{}^{13}C^{17}O])/[^{12}C^{16}O]$, as all common terrestrial materials share a common relationship between $^{17}O/^{16}O$ ($R^{17}$) and $^{18}O/^{16}O$ ($R^{18}$): $(R^{17}_{sample}/R^{17}_{seawater})=(R^{18}_{sample}/R^{18}_{seawater})^{0.528}$.

Combination of the two measured ratios listed above (e.g., $([^{13}C^{16}O]+{}^{12}C^{17}O]/{}^{12}C^{16}O$ and $(^{12}C^{18}O+{}^{13}C^{17}O]/[^{12}C^{16}O])$ with constraints on $R^{17}$ and $R^{18}$ permits unique solution for the $^{13}C/^{12}C$ ratio and $^{18}O/^{16}O$ ratio of the CO fragment of glucose. This fragment is derived from the C=O double bond group at the terminal (C1) position of the glucose molecule. Possible contributions from fragments and recombination products of other carbon and oxygen positions in the molecule are possible; the proportions of these contributions can be determined through analysis of synthetic isotopically labeled standards (this is effectively a case where standardization can be achieved through constraints on both $K_{migration}$ and $K_{redistribution}$). This example illustrates two pieces of information (e.g., $^{13}C$ and $^{18}O$ content of CO) that can be obtained from one of the known fragment ion peaks of glucose, and illustrates just a small fraction of all of the analyzable species.

According to another embodiment of the invention, a method for determining a prior temperature of a sample includes analyzing an analyte of the sample using an embodiment of the second mass spectrometer described herein to obtain molecular analyte ion data. The method further includes analyzing the molecular analyte ion data to obtain the isotopic composition of at least a portion of the analyte. For example, the method can include determining the isotopic composition of at least a portion of an analyte in the sample according to one of the methods described herein. The method also includes comparing the isotopic composition obtained for the analyte to a database of isotopic compositions. The method further includes determining the prior temperature of the sample based on the correlation between the isotopic composition obtained for the analyte and the database of isotopic compositions.

According to another embodiment of the invention, a method of determining an amount of an anthropogenic contribution to an atmospheric concentration of an atmospheric gas includes analyzing an analyte of a sample using an embodiment of the second mass spectrometer described herein to obtain molecular analyte ion data. The method further includes analyzing the molecular analyte ion data to obtain the isotopic composition of at least a portion of the analyte. For example, the method can include determining the isotopic composition of at least a portion of an analyte in the sample according to one of the methods described herein. The method further includes comparing the isotopic composition obtained for the analyte to a database of isotopic compositions. The method also includes determining the amount of the anthropogenic contribution to the atmospheric concentration of the atmospheric gas based on the correlation between the isotopic composition obtained for the analyte and the database of the isotopic compositions. In some embodiments, the analyte is one or more of methane, carbon dioxide, sulfates, hydrocarbons, noble gases, and simple volatile molecular species such as $H_2$, $O_2$, $N_2$, NO, and $N_2O$.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof. Throughout the text and claims, use of the word "about" reflects the penumbra of variation associated with measurement, significant figures, and interchangeability, all as understood by a person having ordinary skill in the art to which this invention pertains. Additionally, throughout this disclosure and the accompanying claims, it is understood that even those ranges that may not use the term "about" to describe the high and low values are also implicitly modified by that term, unless otherwise specified.

What is claimed is:

1. A method for determining the isotopic composition of an analyte in a sample, the method comprising:
using a first mass spectrometer comprising a single-collector and having a mass-resolution of about 30,000 or greater to measure ratios of ion beams at each cardinal mass of the analyte to produce first molecular analyte ion data;
using a second mass spectrometer comprising a multi-collector to measure relative abundances of closely-adjacent ions at different cardinal masses of the analyte to produce second molecular analyte ion data;
utilizing the first molecular analyte ion data to identify proportions of isotopologues that contribute to signal intensity at each cardinal mass measured with the second mass spectrometer; and
utilizing the proportions of the isotopologues that contribute to the signal intensity at each cardinal mass to compensate for unresolved detected molecular analyte species and calculate an abundance of one or more isotopic species of interest measured with the second mass spectrometer.

2. The method of claim 1, wherein the analyte is a high molecular mass compound.

3. The method of claim 1, wherein the analyte is further analyzed using the first mass spectrometer.

4. The method of claim 3, wherein the first mass spectrometer has a mass-resolution of up to 80,000 to 100,000.

5. The method of claim 3, wherein the first mass spectrometer comprises:
a first ion travel path;
a first introduction device configured to select between a reference material and a first portion of the analyte and introduce the selected one of the reference material or the first portion of the analyte to a first ion source, the first ion source having a first entrance slit, the first entrance slit having a first width, the first ion source configured to convert the reference material or the first portion of the analyte to first molecular analyte ions and to guide the first molecular analyte ions along the first ion travel path, each of the first molecular analyte ions having a momentum;
a first momentum filter positioned downstream from the first ion source and configured to receive the first molecular analyte ions, the first momentum filter having a first radius of curvature along the first ion travel path, the first momentum filter configured to filter out second molecular analyte ions from the first molecular analyte ions according to their momenta, each of the second molecular analyte ions having an energy level;
a first energy filter positioned downstream from the first momentum filter and configured to receive the second molecular analyte ions, the first energy filter having a second radius of curvature along the first ion travel path, the first energy filter configured to filter out third molecular analyte ions from the second molecular analyte ions according to their energy levels; and
a detector positioned downstream of the first energy filter and configured to receive the third molecular analyte ions,
wherein the width of the first entrance slit and the first and second radii of curvature are selected to provide a first mass resolution at the detector of about 30,000 or greater.

6. The method of claim 5, wherein the detector comprises the single-collector and the single-collector is configured to detect third molecular analyte ions.

7. The method of claim 5, wherein the first introduction device is configured to receive the first portion of the analyte as a gas phase analyte.

8. The method of claim 5, wherein:
the analyte is a gas phase analyte and the first introduction device comprises a first inlet coupled to a sample reservoir configured to accommodate the gas phase analyte, the reference material is a gas phase reference material and the first introduction device comprises a second inlet coupled to a reference reservoir configured to accommodate the gas phase reference material,
the sample reservoir is configured to accommodate the gas phase analyte at a first pressure,
the reference reservoir is configured to accommodate the gas phase reference material at a second pressure, and
the first and second pressures are the same.

9. The method of claim 5, wherein the first introduction device is configured to receive the first portion of the analyte entrained in a flow of inert gas.

10. The method of claim 5, wherein the first momentum filter is configured to produce a magnetic field, the first energy filter is configured to produce an electric field, and the mass spectrometer is configured to vary masses of the third molecular analyte ions detected at the detector by maintaining a strength of the magnetic field of the first momentum filter at a set value and varying a strength of the electric field of the first energy filter.

11. The method of claim 5, wherein:
the first momentum filter is configured to produce a magnetic field,
the first energy filter is configured to produce an electric field,
the mass spectrometer is configured to vary a first set of masses of the third molecular analyte ions detected at the detector by maintaining a first strength of the magnetic field of the first momentum filter at a first set value and varying a strength of the electric field of the first energy filter, and
the mass spectrometer is configured to vary a second set of masses of the third molecular analyte ions detected at the detector by maintaining a second strength of the magnetic field of the first momentum filter at a second set value and varying a strength of the electric field of the first energy filter.

12. The method of claim 1, wherein the second mass spectrometer is a gas source, double focusing, high resolution multi-collector instrument.

13. The method of claim 1, wherein the second mass spectrometer comprises an inlet system of a gas source isotopic ratio mass spectrometer and an analyser and detector array.

14. The method of claim 1, wherein the second mass spectrometer is a dual-inlet, multi-collector instrument.

15. The method of claim 1, wherein the second mass spectrometer is capable of measuring ions having masses up to 300 amu.

* * * * *